United States Patent
Plebanek et al.

(10) Patent No.: US 10,413,565 B2
(45) Date of Patent: Sep. 17, 2019

(54) NANOSTRUCTURES FOR MODULATING INTERCELLULAR COMMUNICATION AND USES THEREOF

(71) Applicant: Northwestern University, Evanston, IL (US)

(72) Inventors: Michael P. Plebanek, Chicago, IL (US); C. Shad Thaxton, Chicago, IL (US); Raja Kannan Mutharasan, Chicago, IL (US); Nicholas L. Angeloni, Chicago, IL (US); Kaylin M. McMahon, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/339,500

(22) Filed: Oct. 31, 2016

(65) Prior Publication Data

US 2017/0087094 A1    Mar. 30, 2017

Related U.S. Application Data

(63) Continuation-in-part of application No. PCT/US2015/028494, filed on Apr. 30, 2015.

(60) Provisional application No. 62/300,349, filed on Feb. 26, 2016, provisional application No. 62/087,734, filed on Dec. 4, 2014, provisional application No. 61/986,360, filed on Apr. 30, 2014.

(51) Int. Cl.
*A61K 31/713* (2006.01)
*A61K 47/69* (2017.01)
*A61K 47/64* (2017.01)

(52) U.S. Cl.
CPC ........ *A61K 31/713* (2013.01); *A61K 47/6425* (2017.08); *A61K 47/6917* (2017.08)

(58) Field of Classification Search
CPC .............. A61K 31/713; A61K 47/6425; A61K 47/6917
See application file for complete search history.

(56) References Cited

U.S. PATENT DOCUMENTS

| | | |
|---|---|---|
| 5,814,666 A | 9/1998 | Green et al. |
| 7,018,841 B1 | 3/2006 | Ueda et al. |
| 8,252,756 B2 | 8/2012 | Mirkin et al. |
| 8,323,686 B2 | 12/2012 | Mirkin et al. |
| 8,507,200 B2 | 8/2013 | Mirkin et al. |
| 8,999,947 B2 | 4/2015 | Mirkin et al. |
| 9,506,056 B2 | 11/2016 | Mirkin et al. |
| 9,532,948 B2 | 1/2017 | Mirkin et al. |
| 9,693,957 B2 | 7/2017 | Lin et al. |
| 2004/0038891 A1 | 2/2004 | Bisgaier et al. |
| 2005/0106713 A1 | 5/2005 | Phan et al. |
| 2006/0029655 A1 | 2/2006 | Barenholz |
| 2007/0298257 A1 | 12/2007 | Ludwig et al. |
| 2011/0052680 A1 | 3/2011 | Hendrickson |
| 2011/0021334 A1 | 9/2011 | Maier et al. |
| 2011/0268750 A1 | 11/2011 | Mamoun et al. |
| 2011/0305734 A1 | 12/2011 | Edelson et al. |
| 2012/0024701 A1 | 2/2012 | Montagnier et al. |
| 2012/0149843 A1 | 6/2012 | Chien et al. |
| 2012/0282186 A1 | 11/2012 | Mirkin et al. |
| 2013/0034599 A1* | 2/2013 | Thaxton ................ A61K 9/127 424/450 |
| 2013/0089614 A1 | 4/2013 | Zhang et al. |
| 2013/0123333 A1 | 5/2013 | Mirkin et al. |
| 2013/0164740 A1 | 6/2013 | Wu et al. |
| 2013/0196951 A1 | 8/2013 | Schoenfisch et al. |
| 2013/0288253 A1 | 10/2013 | Mirkin et al. |
| 2014/0038901 A1 | 2/2014 | Lyden et al. |
| 2014/0065425 A1 | 3/2014 | Bogdanov |
| 2014/0294927 A1 | 10/2014 | Thaxton et al. |
| 2015/0064255 A1 | 3/2015 | Thaxton et al. |
| 2015/0111790 A1 | 4/2015 | Ategeka et al. |
| 2015/0259680 A1 | 9/2015 | Mirkin et al. |
| 2016/0194642 A1 | 7/2016 | Gryaznov et al. |
| 2016/0274134 A1 | 9/2016 | Mutharasan et al. |
| 2016/0310425 A1 | 10/2016 | Mirkin et al. |
| 2017/0137809 A1 | 5/2017 | Mirkin et al. |

FOREIGN PATENT DOCUMENTS

| | | |
|---|---|---|
| CN | 102165061 A | 8/2011 |
| EP | 1 889 911 A2 | 2/2008 |
| JP | 2011-507807 | 3/2011 |
| JP | 2011-518826 | 6/2011 |

(Continued)

OTHER PUBLICATIONS

Vlassov, et al., Exosomes: current knowledge of their composition, biological functions, and diagnostic and therapeutic potentials. Biochim. Biophys. Acta 1820, 940-948 (2012).*
Twiddy, et al., Knockdown of scavenger receptor class B type I reduces prostate specific antigen secretion and viability of prostate cancer cells, Prostate. Jun. 15, 2012;72(9):955-65, Abstract.*
Acton, S. et al. Identification of scavenger receptor SR-as a high density lipoprotein receptor. Science 271, 518-520 (1996).
Anastasiadou, E. & Slack, F.J. Cancer. Malicious exosomes. Science 346, 1459-1460 (2014).
Atshaves, B.P. et al. SCP-2/SCP-x gene ablation alters lipid raft domains in primary cultured mouse hepatocytes. *J Lipid Res* 48, 2193-2211 (2007).
Challagundla, K. B. et al. Exosome-mediated transfer of microRNAs within the tumor microenvironment and neuroblastoma resistance to chemotherapy. *J. Natl. Cancer I.* 107 (2015).
Damiano, M. G. et al. Templated high density lipoprotein nanoparticles as potential therapies and for molecular delivery. *Adv. Drug Deliver. Rev.* 65, 649-662 (2013).

(Continued)

*Primary Examiner* — H. Sarah Park
(74) *Attorney, Agent, or Firm* — Wolf, Greenfield & Sacks, P.C.

(57) ABSTRACT

Nanostructures, compositions and methods for treating vesicle-related or exosome-related conditions are provided. In some cases, the nanostructures and/or compositions may be used to treat cancers, neurological disorders, rheumatologic disorders, viral disorders or other diseases or conditions at least in part by regulating vesicle uptake. Methods of analyzing, imaging and modulating vesicles and cellular vesicles processes are also provided.

7 Claims, 50 Drawing Sheets

(56) References Cited

FOREIGN PATENT DOCUMENTS

| WO | WO 1995/034289 A1 | 12/1995 |
|---|---|---|
| WO | WO 1998/004740 A1 | 2/1998 |
| WO | WO 2001/003709 A1 | 1/2001 |
| WO | WO 2006/128121 A2 | 11/2006 |
| WO | WO 2008/014979 A2 | 2/2008 |
| WO | WO 2009/012786 A2 | 1/2009 |
| WO | WO 2009/073984 A1 | 6/2009 |
| WO | WO 2009/131931 A1 | 10/2009 |
| WO | WO 2010/091293 A1 | 8/2010 |
| WO | WO 2010/120420 | 10/2010 |
| WO | WO 2011/072133 A1 | 6/2011 |
| WO | WO 2011/113054 A2 | 9/2011 |
| WO | WO 2012/097177 | 7/2012 |
| WO | WO 2014/052188 A1 | 4/2014 |
| WO | WO 2014/169264 A2 | 10/2014 |
| WO | WO 2015/013673 | 1/2015 |
| WO | WO 2015/013675 | 1/2015 |
| WO | WO 2015/153975 A1 | 10/2015 |
| WO | WO 2015/187966 A1 | 12/2015 |
| WO | WO 2016/057549 A1 | 4/2016 |
| WO | WO 2017/011662 A1 | 1/2017 |
| WO | WO 2017/035278 A1 | 3/2017 |
| WO | WO 2017/193087 A1 | 11/2017 |
| WO | WO 2018/053368 A1 | 3/2018 |

OTHER PUBLICATIONS

Del Pozo, M.A. et al. Phospho-caveolin-1 mediates integrin-regulated membrane domain internalization. Nat Cell Biol. 7 (9), 901-8 (2005).
Ekstrom, E.J. et al. WNT5A induces release of exosomes containing pro-angiogenic and immunosuppressive factors from malignant melanoma cells. *Molecular cancer* 13, 88 (2014).
Feng, D., et al. Cellular internalization of exosomes occurs through phagocytosis. *Traffic* 11, 675-687 (2010).
Filipazzi, P. et al. Recent advances on the role of tumor exosomes in immunosuppression and disease progression. *Seminars in cancer biology* 22, 342-349 (2012).
Gabitova, L. et al. Molecular Pathways: Sterols and Receptor Signaling in Cancer. Clin Cancer Res, 20 (1), 28-34 (2014).
Gantman, A. et al. High glucose stimulates macrophage SR-BI expression and induces a switch in its activity from cholesterol efflux to cholesterol influx. *Biochemical and biophysical research communications* 391, 523-528 (2010).
Ghajar, C.M. et al. The perivascular niche regulates breast tumour dormancy. Nat Cell Biol, 15 (7), 807-+ (2013).
Hergenreider, E. et al Atheroprotective communication between endothelial cells and smooth muscle cells through miRNAs. Nat Cell Biol, 14 (3), 249-+ (2012).
Hesterberg, Tim, et al. Bootstrap methods and permutation tests (2010).
Hood, J.L. et al. Paracrine induction of endothelium by tumor exosomes. *Laboratory investigation; a journal of technical methods and pathology* 89, 1317-1328 (2009).
Hood, J.L. et al. Exosomes released by melanoma cells prepare sentinel lymph nodes for tumor metastasis. *Cancer research* 71, 3792-3801 (2011).
Huang, R. et al. Apolipoprotein A-I structural organization in high-density lipoproteins isolated from human plasma. *Nature structural & molecular biology* 2011, 18, (4), 416-22.
Jaqaman, K. et al. Robust single-particle tracking in live-cell time-lapse sequences. *Nat Methods* 5, 695-702 (2008).
Johnsen, K. B. et al. A comprehensive overview of exosomes as drug delivery vehicles—endogenous nanocarriers for targeted cancer therapy. *Biochim. Biophys. Acta* 1846, 75-87 (2014).
Jung, T. et al. CD44v6 dependence of premetastatic niche preparation by exosomes. *Neoplasia* 11, 1093-1105 (2009).
Katakowski, M. et al. Exosomes from marrow stromal cells expressing miR-146b inhibit glioma growth. *Cancer Lett.* 335, 201-204 (2013).
Kharaziha, P. et al. Molecular profiling of prostate cancer derived exosomes may reveal a predictive signature for response to docetaxel. *Oncotarget* 6, 21740-21754 (2015).
Lajoie, P. et al. Regulation of raft-dependent endocytosis. J Cell Mol Med; 11 (4), 644-53 (2007).
Lingwood, D. & Simons, K. Lipid Rafts As a Membrane-Organizing Principle. *Science* 327, 46-50 (2010).
Lavie, M. et al. Identification of conserved residues in hepatitis C virus envelope glycoprotein E2 that modulate virus dependence on CD81 and SRB1 entry factors. *J. Virol.* 88, 10584-10597 (2014).
Lazar, I. et al. Proteome characterization of melanoma exosomes reveals a specific signature for metastatic cell lines. *Pigment Cell Melanoma Res.* 28, 464-475 (2015).
Luthi, A. J. et al. Nanotechnology for synthetic high-density lipoproteins. *Trends Mol. Med.* 16, 553-560 (2010).
Luthi, A.J. et al. Tailoring of biomimetic high-density lipoprotein nanostructures changes cholesterol binding and efflux. *ACS nano* 6, 276-285 (2012).
Luthi, A.J. et al. Robust passive and active efflux of cellular cholesterol to a designer functional mimic of high-density lipoprotein. *J Lipid Res* (2015).
Lydic, T. A. et al. Rapid and comprehensive 'shotgun' lipidome profiling of colorectal cancer cell derived exosomes. Methods, doi:10.1016/j.ymeth.2015.04.014 (2015).
Martins, V.R. et al. Tumor-cell-derived microvesicles as carriers of molecular information in cancer. *Curr Opin Oncol* 25, 66-75 (2013).
Marton, A. et al. Melanoma cell-derived exosomes alter macrophage and dendritic cell functions in vitro. *Immunol Lett* 148, 34-38 (2012).
Matveev, S. et al. Co-expression of scavenger receptor-BI and caveolin-1 is associated with enhanced selective cholesteryl ester uptake in THP-1 macrophages. *J Lipid Res* 40, 1647-1654 (1999).
McMahon, K.M. et al. Biomimetic high density lipoprotein nanoparticles for nucleic acid delivery. *Nano letters* 11, 1208-1214 (2011).
McMahon, K.M. & Thaxton, C.S. High-density lipoproteins for the systemic delivery of short interfering RNA. *Expert opinion on drug delivery* 11, 231-247 (2014).
Melo, S. A. et al. Glypican-1 identifies cancer exosomes and detects early pancreatic cancer. *Nature* 523, 177-182 (2015).
Mu, W. et al. Host Matrix Modulation by Tumor Exosomes Promotes Motility and Invasiveness. Neoplasia, 15 (8), 875-887 (2013).
Neculai, D. et al. Structure of LIMP-2 provides functional insights with implications for SR-BI and CD36. *Nature* 504, 172-176 (2013).
Nieland, T.J. et al. Discovery of chemical inhibitors of the selective transfer of lipids mediated by the HDL receptor SR-BI. *Proceedings of the National Academy of Sciences of the United States of America* 99, 15422-15427 (2002).
Nolan, J. P. Flow Cytometry of Extracellular Vesicles: Potential, Pitfalls, and Prospects. *Curr. Protoc. Cytom.* 73, 13.14.1-13.14.16 (2015).
Nomura, R. et al. Tyrosine-phosphorylated Caveolin-1: Immunolocalization and Molecular Charatzeration. Molecular biology of the cell, 10 (4), 975-86 (1999).
Norata, G.D. et al. HDL3 Induces Cyclooxygenase-2 Expression and Prostacyclin Release in Human Endothelial Cells Via a p38 MAPK/CRE-Dependent Pathway: Effects on COX-2/PGI-Synthases Coupling. Arteriosclerosis thrombosis and vascular biology, 24 (5), 871-7 (2004).
Peinado, H. et al. The secreted factors responsible for pre-metastatic niche formation: old sayings and new thoughts. *Seminars in cancer biology* 21, 139-146 (2011).
Peinado, H. et al. Melanoma exosomes educate bone marrow progenitor cells toward a pro-metastatic phenotype through MET. *Nature medicine* 18, 883-891 (2012).
Perez-Hernandez, D. et al. The intracellular interactome of tetraspanin-enriched microdomains reveals their function as sorting machineries toward exosomes. *J. Biol. Chem.* 288, 11649-11661 (2013).
Pike, L.J., Lipid rafts: bring order to chaos. J Lipid Res 44, 655-667 (2003).
Plebanek, M. P. et al. Nanoparticle Targeting and Cholesterol Flux Through Scavenger Receptor Type B-1 Inhibits Cellular Exosome Uptake. *Sci. Rep.* 5, 15724, (2015).

(56) References Cited

OTHER PUBLICATIONS

Putz, U. et al. The Tumor Suppressor PTEN Is Exported in Exosomes and Has Phosphatase Activity in Recipient Cells. *Sci Signal* 5(2012).
Rader, D. J. et al. The role of reverse cholesterol transport in animals and humans and relationship to atherosclerosis. *J Lipid Res* 2009, 50 Suppl, S189-94.
Rajendran, L. et al. Alzheimer's disease beta-amyloid peptides are released in association with exosomes. *Proceedings of the National Academy of Sciences of the United States of America* 103, 11172-11177 (2006).
Ramakrishnaiah, V. et al. Exosome-mediated transmission of hepatitis C virus between human hepatoma Huh7.5 cells. *Proceedings of the National Academy of Sciences of the United States of America* 110, 13109-13113 (2013).
Rana, S. & Zoller, M. Exosome target cell selection and the importance of exosomal tetraspanins: a hypothesis. *Biochem. Soc. T.* 39, 559-562 (2011).
Rana, S. et al., M. Toward tailored exosomes: the exosomal tetraspanin web contributes to target cell selection. *Int. J. Biochem. Cell B.* 44, 1574-1584 (2012).
Rocha-Perugini, V. et al. The association of CD81 with tetraspanin-enriched microdomains is not essential for Hepatitis C virus entry. *BMC Microbiol.* 9, 111 (2009).
Rothblat, G.H. et al. Cell cholesterol efflux: integration of old and new observations provides new insights. J Lipid Res 40 (5), 781-796 (1999).
Shahzad, M. M. et al. Targeted Delivery of Small Interfering RNA Using Reconstituted High-Density Lipoprotein Nanoparticles. Neoplasia, 13 (4), 309-19 (2011).
Simons, K. & Gerl, M.J. Revitalizing membrane rafts: new tools and insights. *Nat Rev Mal Cell Bio* 11, 688-699 (2010).
Svensson, K.J. et al. Exosome uptake depends on ERK1/2-heat shock protein 27 signaling and lipid Raft-mediated endocytosis negatively regulated by caveolin-1. *The Journal of biological chemistry* 288, 17713-17724 (2013).
Thaxton, C.S. et al. Templated spherical high density lipoprotein nanoparticles. *Journal of the American Chemical Society* 131, 1384-1385 (2009).
Thery, C. et al. Isolation and characterization of exosomes from cell culture supernatants and biological fluids. *Current protocols in cell biology /editorial board*, Juan S. Bonifacino et al. Chapter 3, Unit 3 22 (2006).
Tripathy, S. et al. High Density Lipoprotein Nanoparticles Deliver RNAi to Endothelial Cells to Inhibit Angiogenesis. *Part. Syst. Char.* 31, 1141-1150 (2014).
Umemoto, T. et al. Apolipoprotein AI and high-density lipoprotein have anti-inflammatory effects on adipocytes via cholesterol transporters: ATP-binding cassette A-1, ATP-binding cassette G-1, and scavenger receptor B-1. *Circulation research* 112, 1345-1354 (2013).
Urban, S. et al. Scavenger receptor BI transfers major lipoprotein-associated phospholipids into the cells. *J. Biol. Chem.* 275, 33409-33415 (2000).
Valadi, H. et al. Exosome-mediated transfer of mRNAs and microRNAs is a novel mechanism of genetic exchange between cells. *Nat Cell Biol* 9, 654-659 (2007).
Van Eck, M. et al. Scavenger receptor BI and ATP-binding cassette transporter A1 in reverse cholesterol transport and atherosclerosis. *Curr Opin Lipidol* 16, 307-315 (2005).
Vlassov, A. V., et al. Exosomes: current knowledge of their composition, biological functions, and diagnostic and therapeutic potentials. *Biochim. Biophys. Acta* 1820, 940-948 (2012).
Xiang, X. et al. Induction of myeloid-derived suppressor cells by tumor exosomes. *International journal of cancer. Journal international du cancer* 124, 2621-2633 (2009).
Yang, S.O. et al. Biomimetic, synthetic HDL nanostructures for lymphoma. *Proceedings of the National Academy of Sciences of the United States of America* 110, 2511-2516 (2013).
Yu, X. et al. The regulation of exosome secretion: a novel function of the p53 protein. *Cancer research* 66, 4795-4801 (2006).
Yu, S. et al. Tumor-derived exosomes in cancer progression and treatment failure. *Oncotarget* (2015).
Zhang, J. et al. Lipoprotein binding preference of CD36 is altered by filipin treatment. *Lipids in health and disease* 7, 23 (2008).
Zitvogel, L. et al. Eradication of established murine tumors using a novel cell-free vaccine: dendritic cell-derived exosomes. *Nat. Med.* 4, 594-600 (1998).
Zoller, M. Tetraspanins: push and pull in suppressing and promoting metastasis. *Nature reviews. Cancer* 9, 40-55 (2009).
Asthana et al., Mannosylated chitosan nanoparticles for delivery of antisense oligonucleotides for macrophage targeting. Biomed Res Int. 2014;2014:526391. doi: 10.1155/2014/526391. Epub Jun. 26, 2014.
Dave et al., Programmable assembly of DNA-functionalized liposomes by DNA. ACS Nano. Feb. 22, 2011;5(2):1304-12. doi: 10.1021/nn1030093. Epub Jan. 4, 2011.
Gissot et al., Nucleoside, nucleotide and oligonucleotide based amphiphiles: a successful marriage of nucleic acids with lipids. Org. Biomol. Chem. 2008;6:1324-33.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Khmelinskaia et al., Effect of anchor positioning on binding and diffusion of elongated 3D DNA nanostructures on lipid membranes. J. Phys. D: Appl. Phys. Apr. 13, 2016:49(19):194001.
Mozos et al., The expression of the endoplasmic reticulum stress sensor BiP/GRP78 predicts response to chemotherapy and determines the efficacy of proteasome inhibitors in diffuse large b-cell lymphoma. Am J Pathol. Nov. 2011;179(5):2601-10. doi:10.1016/j.ajpath.2011.07.031. Epub Sep. 9, 2011.
Nam et al., Nanoparticle-based bio-bar codes for the ultrasensitive detection of proteins. Science. Sep. 26, 2003;301(5641):1884-6.
Palekar et al., Nanoparticle-based biosensors for the detection of lecithin: cholesterol acyltransferase activity. The FASEB J. Apr. 2017;31(1). Abstract.
Patwa et al., Hybrid lipid oligonucleotide conjugates: synthesis, self-assemblies and biomedical applications. Chem Soc Rev. 2011;40:5844-54.
Pokholenko et al., Lipid oligonucleotide conjugates as responsive nanomaterials for drug delivery. J of Materials Chemistry B. 2013;5329-34.
Qin et al., Significantly improved analytical sensitivity of lateral flow immunoassays by using thermal contrast. Angew Chem Int Ed Engl. Apr. 27, 2012;51(18):4358-61. doi:10.1002/anie.201200997. Epub Mar. 23, 2012.
Shukoor et al., CpG-DNA loaded multifunctional MnO nanoshuttles for TLR9-specific cellular cargo delivery, selective immune-activation and MRI. J. Mater. Chem., 2012,22, 8826-8834.
Thompson et al., Smart lipids for programmable nanomaterials. Nano Lett. Jul. 14, 2010;10(7):2690-3. doi: 10.1021/nl101640k.
Yin et al., Supramolecular self-assembled nanoparticles mediate oral delivery of therapeutic TNF-α siRNA against systemic inflammation. Angew Chem Int Ed Engl. May 27, 2013;52(22):5757-61. doi: 10.1002/anie.201209991. Epub Apr. 22, 2013.
Zhang et al., Informational liposomes: Complexes derived from cholesteryl-conjugated oligonucleotides and liposomes. Tetrahedron Letters. 1996. 37(35):6243-6.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas. 1118425109. Epub Jul. 6, 2012.
Aurasense Therapeutics, NIH grant. Topically-delivered Target Gene Suppression of Immune Activation in Psoriasis—David Giljohann. Accessed on Aug. 2, 2017 from http://grantome.com/grant/NIH/R41-AR066438-01. Accessible online on Feb. 21, 2016 as verified through Wayback Machine.
Boudreault et al., Nanoscale tools to selectively destroy cancer cells. Chem Commun. May 14, 2008;(18):2118-20. doi: 10.1039/b800528a. Epub Apr. 7, 2008.
Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.

(56) References Cited

OTHER PUBLICATIONS

Palekar et al., Nanoparticle-based biosensors for the detection of lecithin: cholesterol acyltransferase activity. The FASEB J. Apr. 2017;31(1).

Polizzi et al., Water-soluble nitric oxide-releasing gold nanoparticles. Langmuir. Apr. 24, 2007;23(9):4938-43. Epub Mar. 22, 2007.

Pollard, A guide to simple and informative binding assays. Mol Biol Cell. Dec. 2010;21(23):4061-7. doi: 10.1091/mbc.E10-08-0683.

Rothrock et al., Synthesis of nitric oxide-releasing gold nanoparticles. J Am Chem Soc. Jul. 6, 2005;127(26):9362-3.

Saraiva et al., Nanocarriers for nitric oxide delivery. J Drug Deliv. 2011;2011:936438. doi: 10.1155/2011/936438. Epub Aug. 22, 2011.

Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.

[No Author Listed] United States Securities and Exchange Commission Form 8-K Current Report, Date of Report (Date of earliest event reported): Sep. 26, 2017, Exicure, Inc. Dated: Oct. 2, 2017 by David Giljohann Accessed from the internet (Oct. 11, 2018) at https://www.sec.gov/Archives/edgar/data/1698530/000119312517301064/d461080d8k.htm.

Briley et al., In Nanomaterials for Biomedicine; American Chemical Society. 2012;1119:1-20.

Li et al., Oligonucleotide-conjugated nanoparticles for targeted drug delivery via scavenger receptors class A: An in vitro assessment for proof-of-concept. Int J Pharm. Oct. 30, 2017;532(1):647-655. doi: 10.1016/j.ijpharm.2017.08.074. Epub Aug. 18, 2017.

Pearson et al., Polynucleotide Binding to Macrophage Scavenger Receptors Depends on the Formation of Base-quartet-stabilized Four-stranded Helices. JBC, VOi. 268, No. 5, Issue of Feb. 15. pp. 3546-3554, 1993 (Year: 1993).

SITA et al., Dual bioluminescence and near-infrared fluorescence monitoring to evaluate spherical nucleic acid nanoconjugate activity in vivo. Proc Natl Acad Sci U S A. Apr. 18, 2017;114(16):4129-4134. doi: 10.1073/pnas.1702736114. Epub Apr. 3, 2017.

* cited by examiner

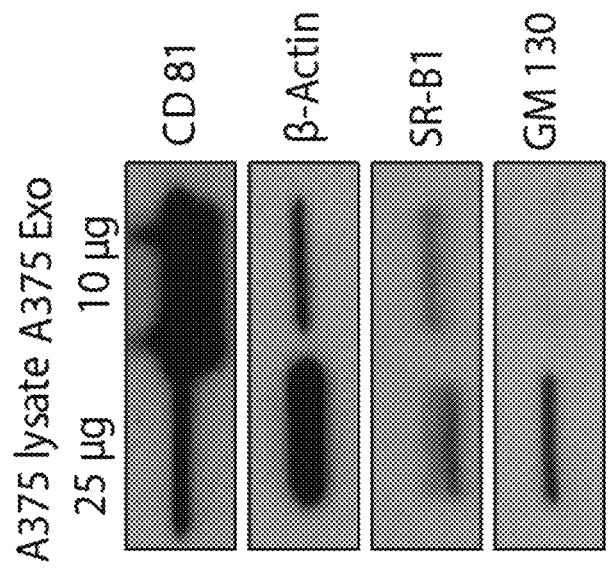
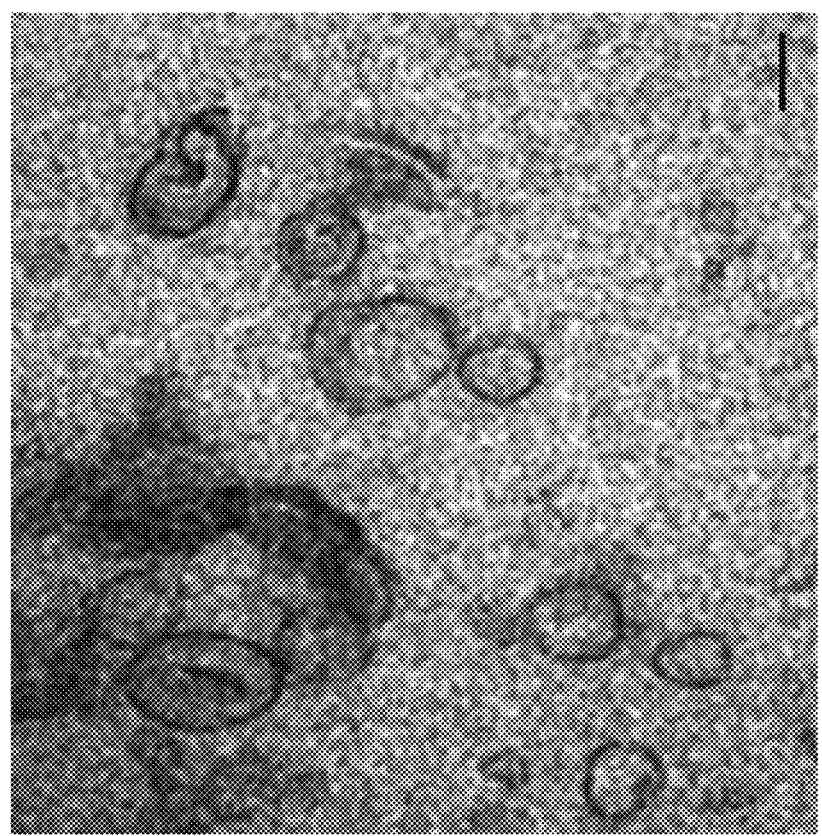
FIGURE 1C
FIGURE 1A

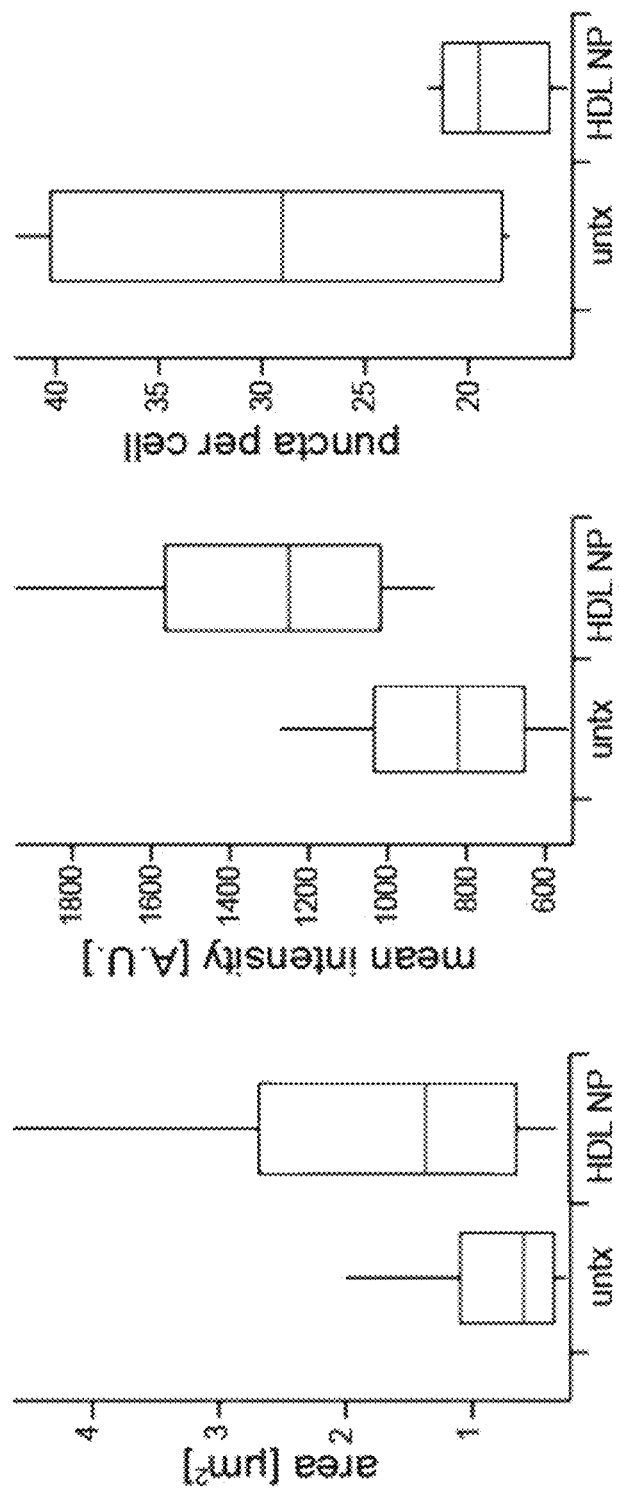

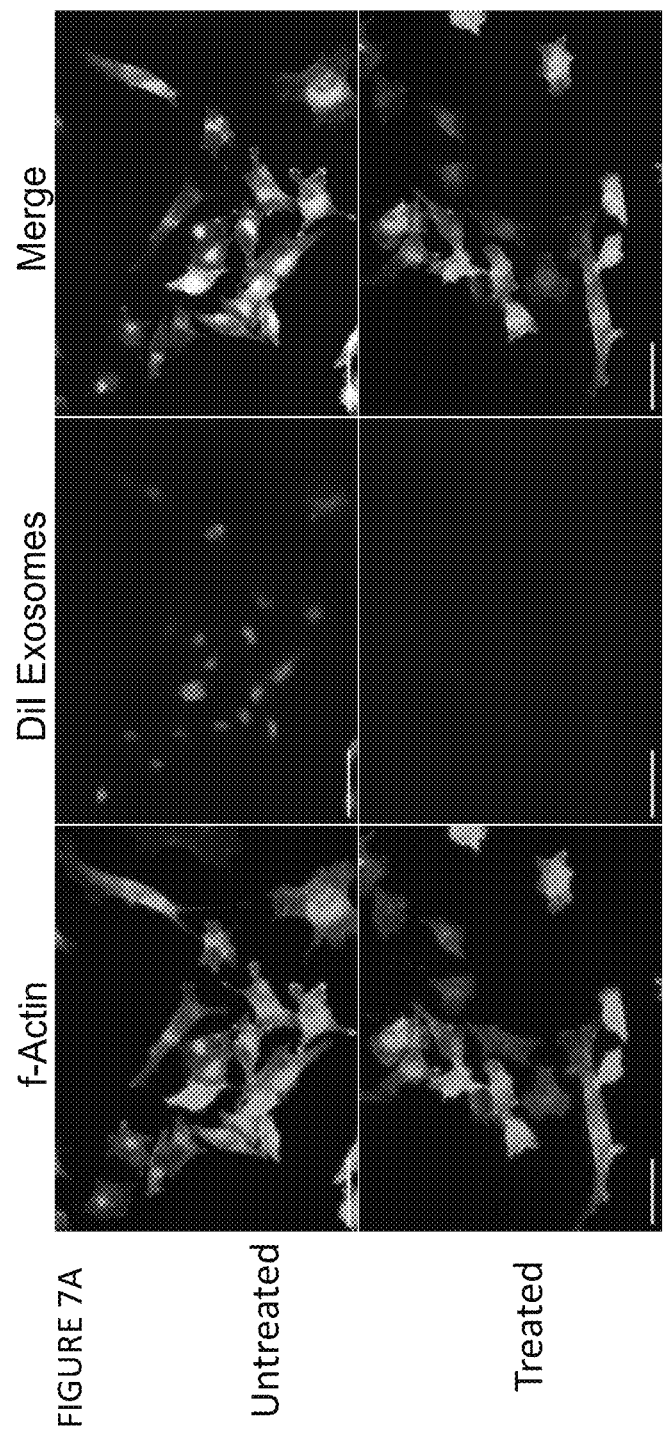

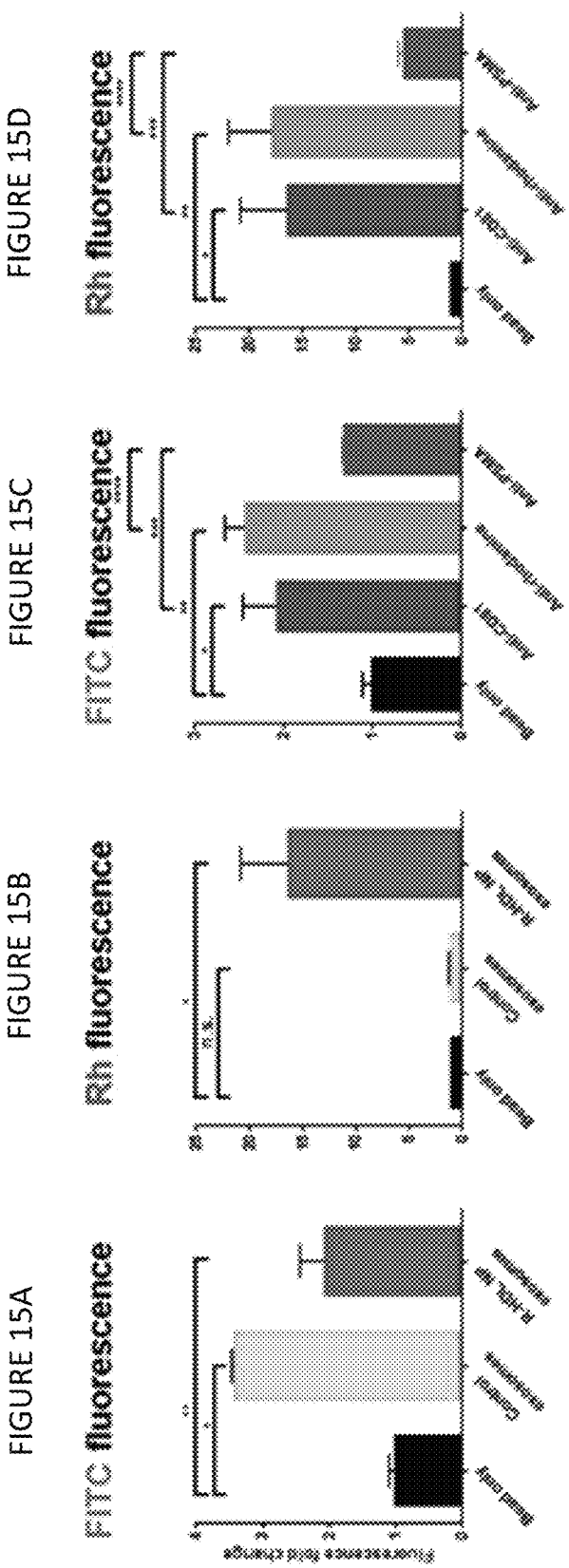

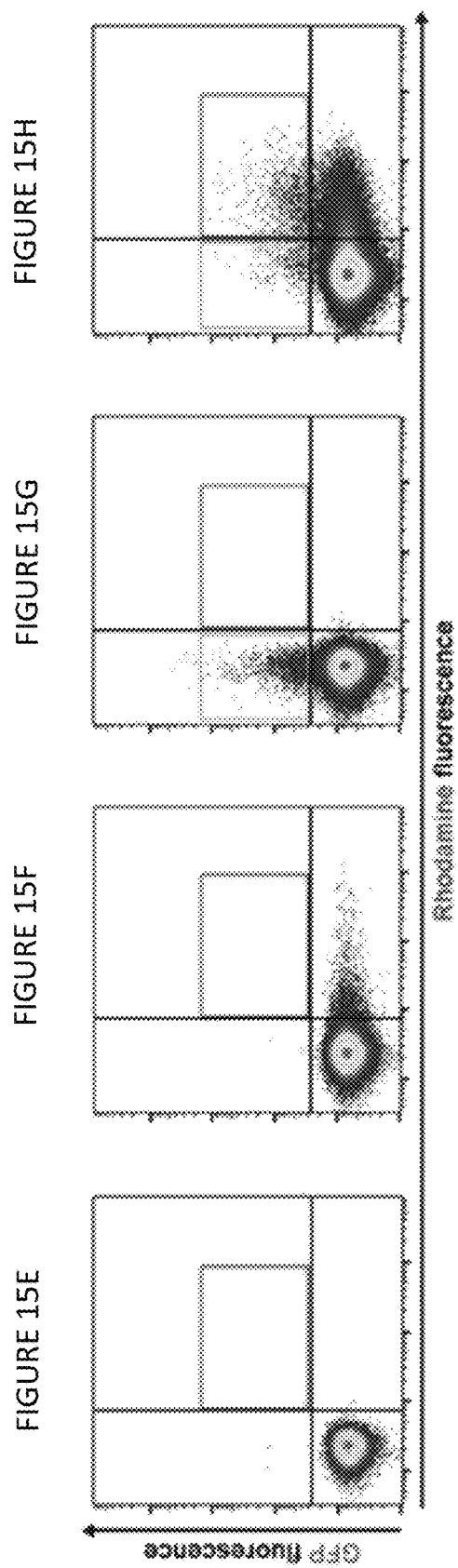

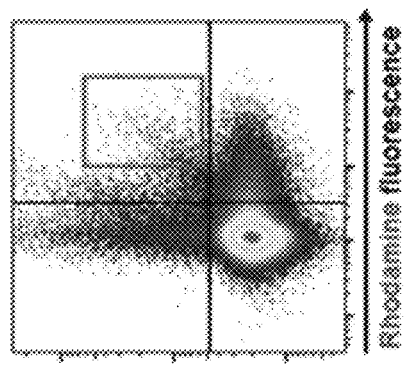
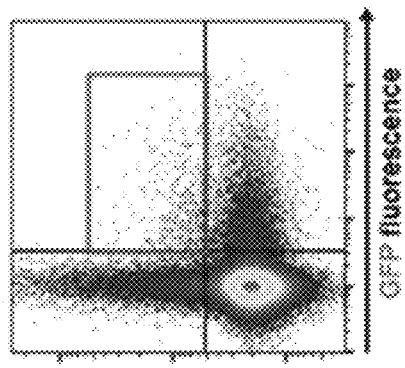
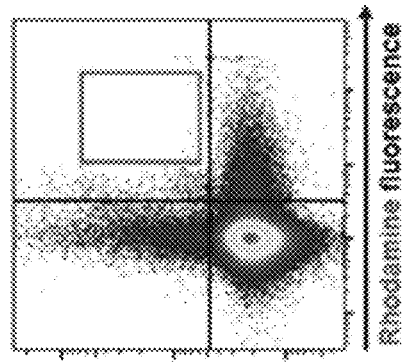
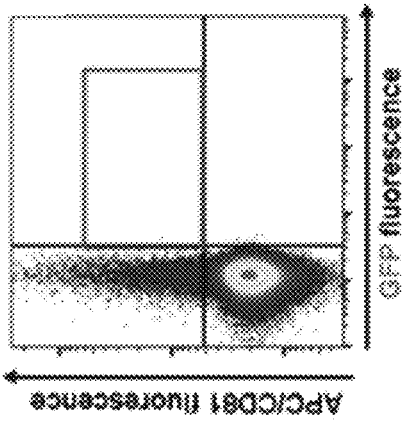

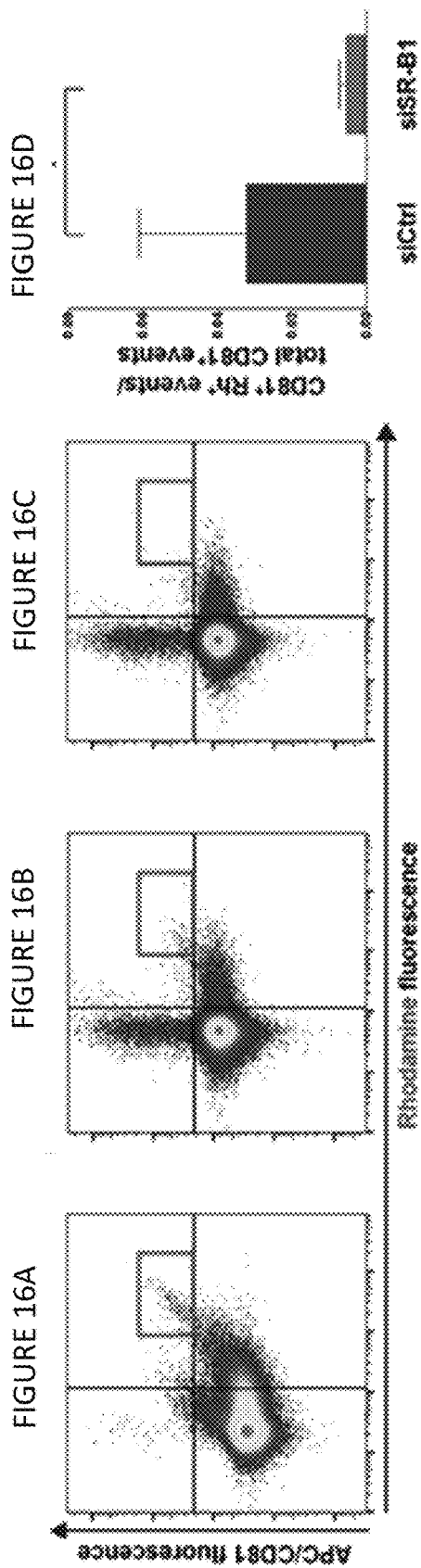

FIGURE 19E
FIGURE 19F
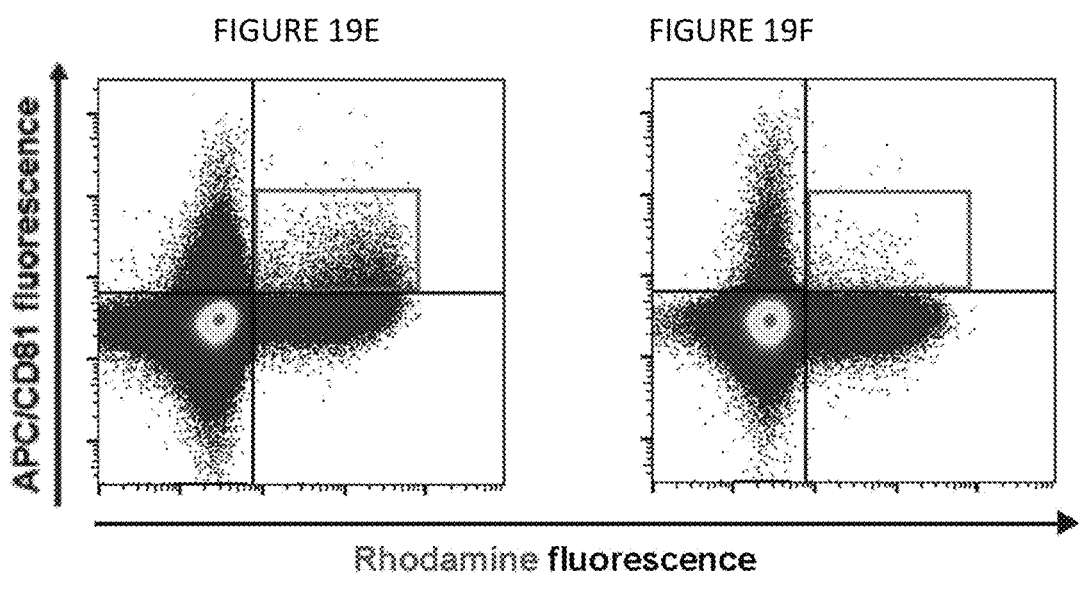
FIGURE 19G
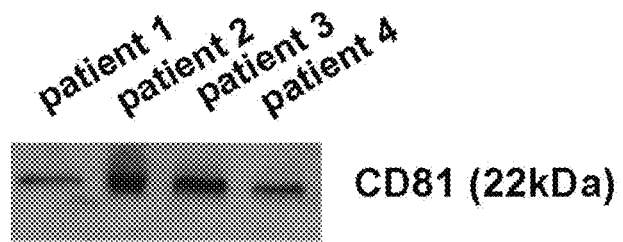
CD81 (22kDa)

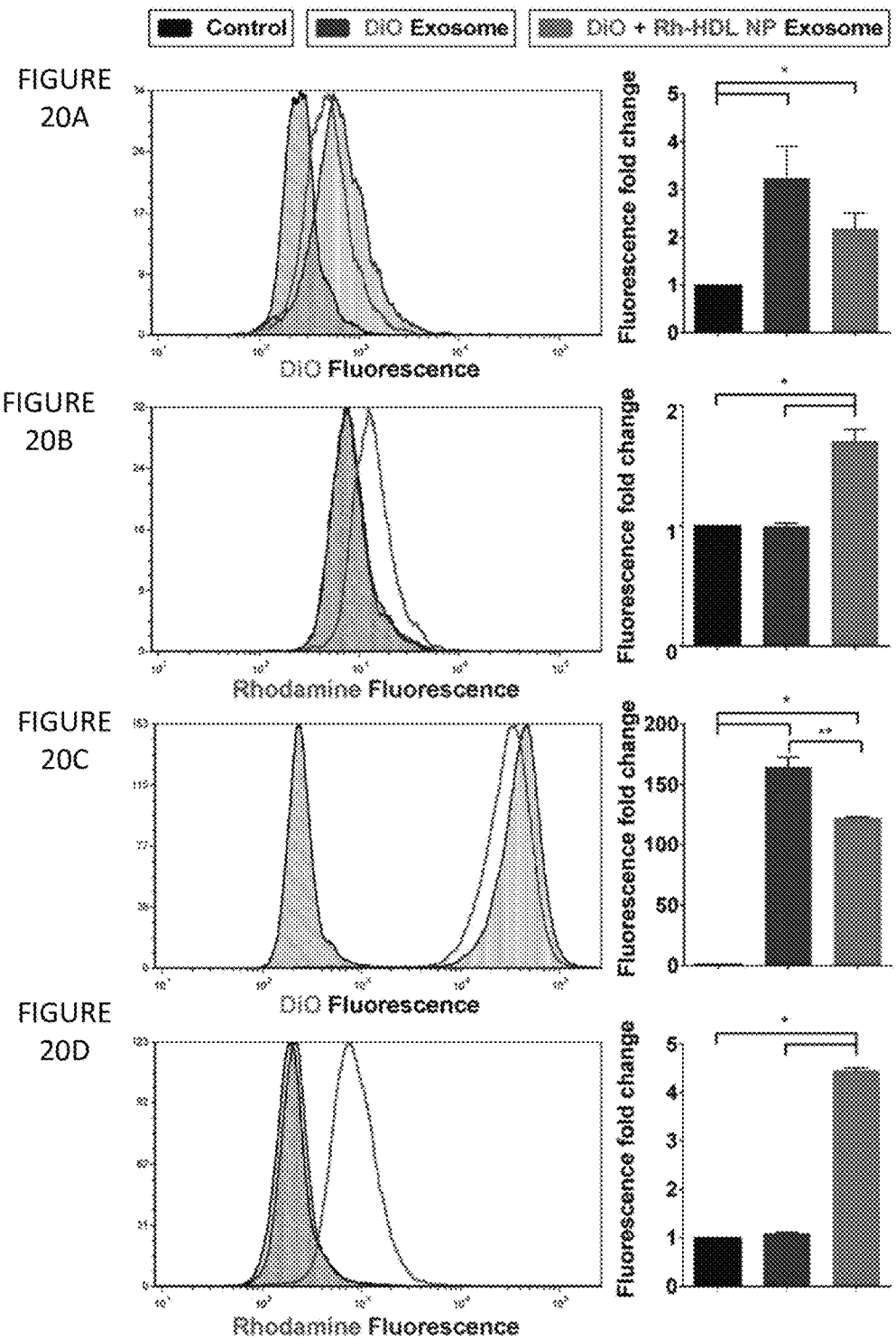

HDL NP

Rh-HDL NP

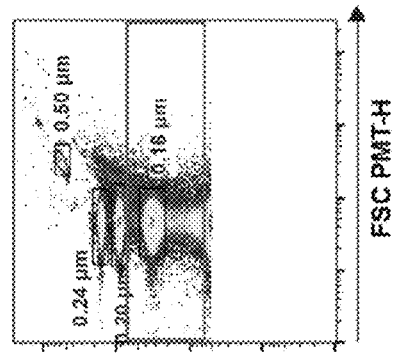
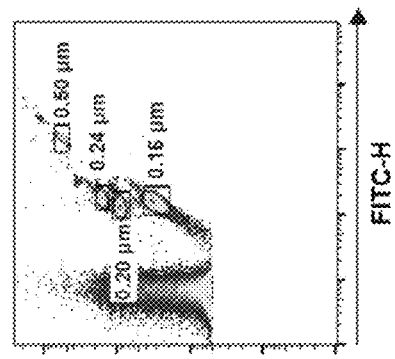
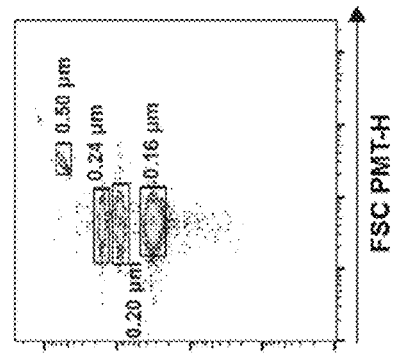
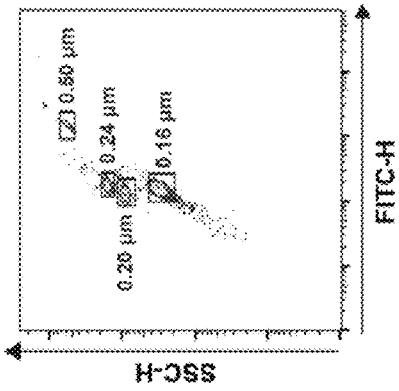

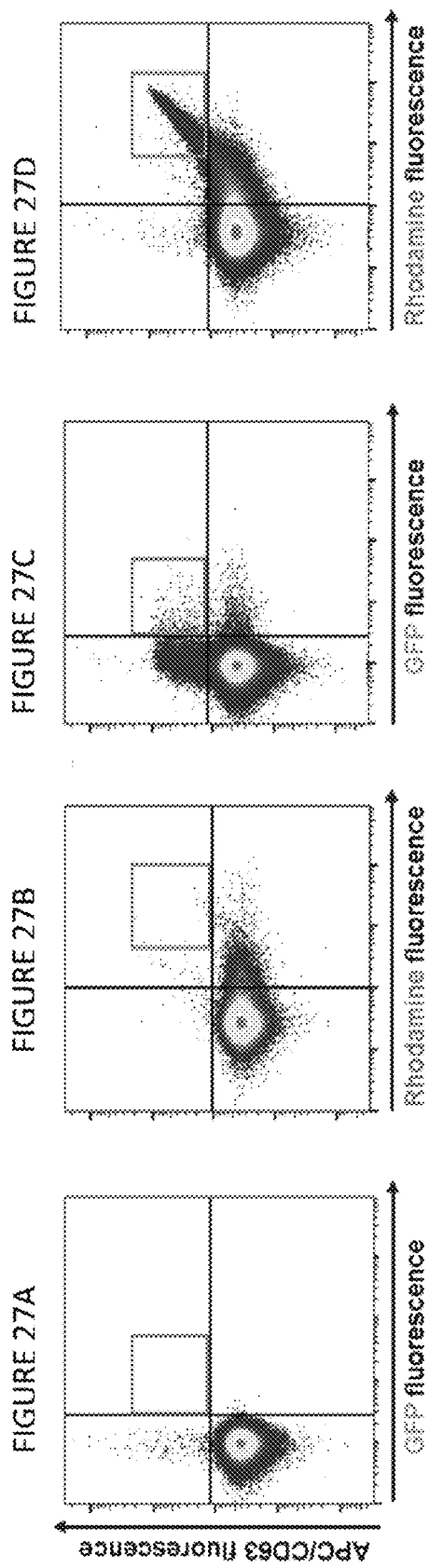

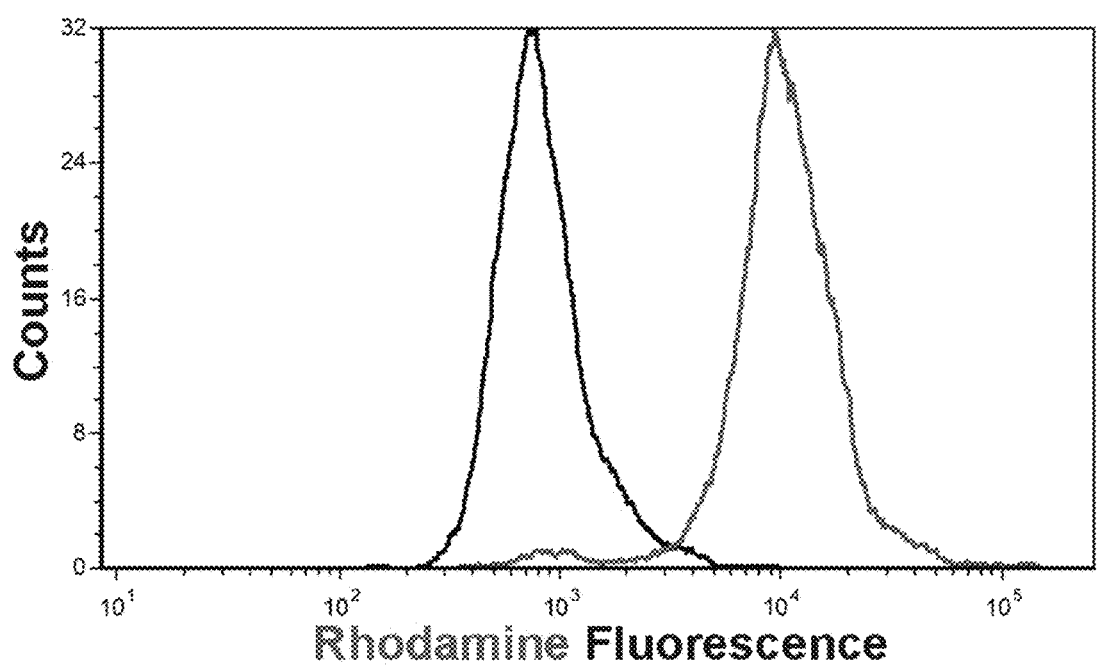

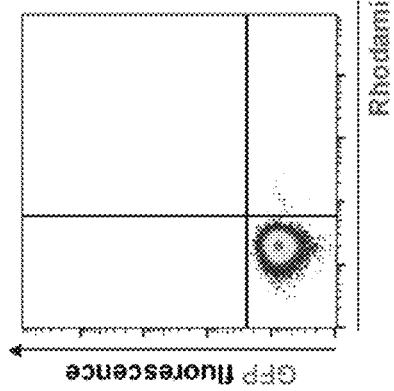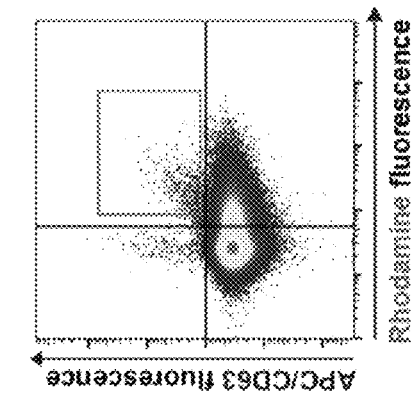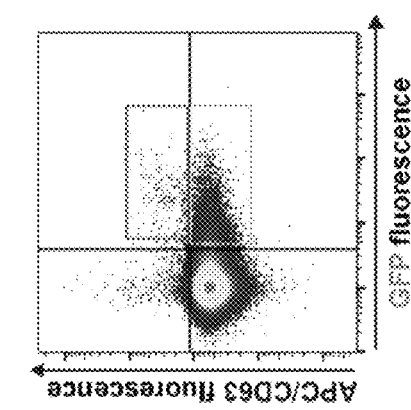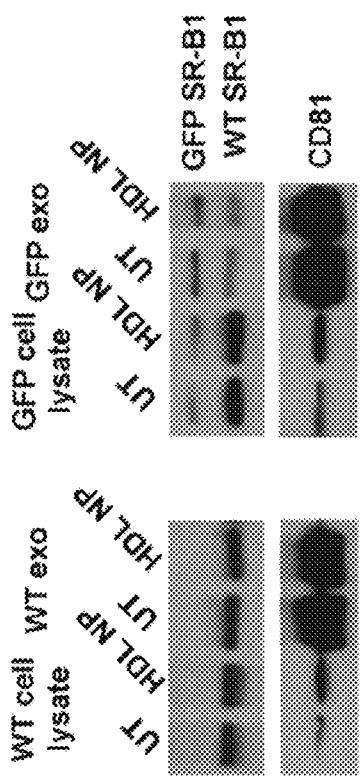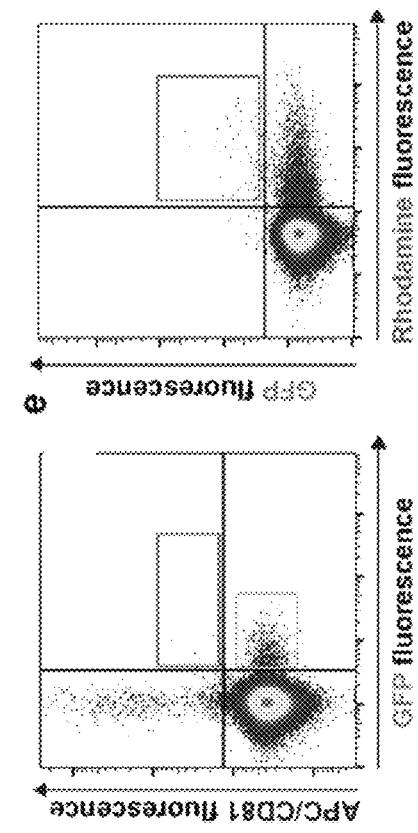
FIGURE 29A
FIGURE 29B
FIGURE 29C
FIGURE 29D
FIGURE 29E
FIGURE 29F
FIGURE 29G

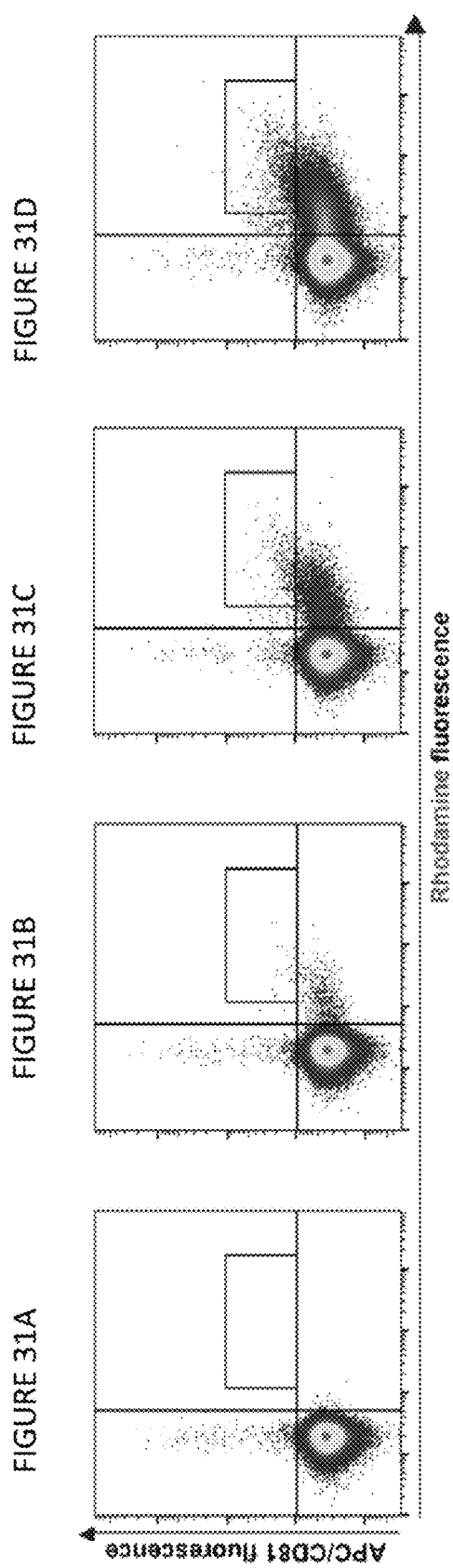

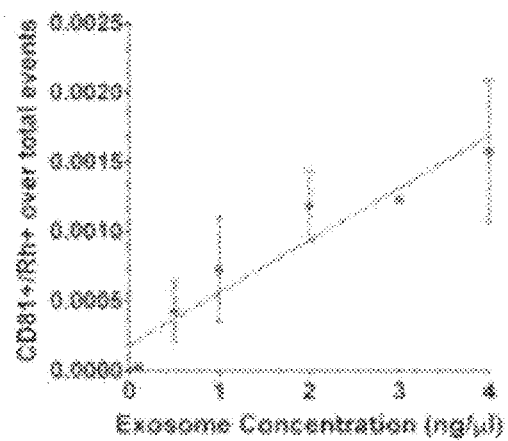
FIGURE 31E
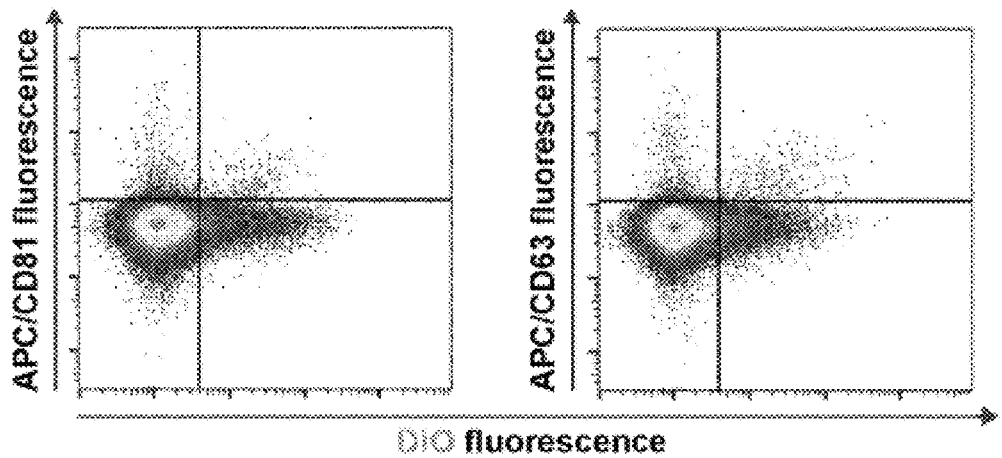
FIGURE 32A
FIGURE 32B

NANOSTRUCTURES FOR MODULATING INTERCELLULAR COMMUNICATION AND USES THEREOF

CROSS-REFERENCE TO RELATED APPLICATIONS

The benefit is claimed of International Application No. PCT/US2015/028494, filed 30 Apr. 2015, and U.S. Provisional Application Nos. 62/300,349, filed 26 Feb. 2016, 62/087,734, filed 4 Dec. 2014, and 61/986,360, filed 30 Apr. 2014, the disclosures of which are incorporated by reference in their entireties.

STATEMENT OF GOVERNMENT SUPPORT

This invention was made with government support under R01 CA167041 and CA060553 awarded by the National Institutes of Health and FA9550-13-1-0192 awarded by the Air Force Office of Scientific Research (AFOSR). The government has certain rights in the invention.

FIELD OF INVENTION

The present invention generally relates to nanostructures and compositions for modulating or monitoring intercellular communication via vesicles and uses thereof.

BACKGROUND

One of the major mediators of intercellular communication is exosomes [Martins et al., 2013]. Exosomes are 30-100 nm nanovesicles responsible for the transport of a myriad of molecular cargo including protein, lipids, mRNA and miRNA [Valadi et al., 2007]. Exosome signaling is linked to a number of pathologies including cancer [Martins et al., 2013; Jung et al., 2009], neurological disorders [Rajendran et al., 2006], and cardiovascular disease [Hergenreider et al., 2012]. For example, local and distal communication between tumor and supporting cells is critical for tumor progression [Peinado et al., 2012; Ghajar et al., 2013].

Because of their role in disease progression and inherent targeting properties there is significant interest in exosome production, detection, and manipulation of their molecular content [Katakowski et al. 2013; Rana et al. 2012]. For example, isolated cells have been engineered to overexpress certain potentially therapeutic cargoes that can be packaged into secreted exosomes whereupon the exosomes are then systemically delivered as a therapeutic [Johnsen et al. 2014]. In addition, dendritic cells have been shown to process antigens ex vivo that are then presented on the surface of secreted exosomes, which can then be isolated and systemically delivered to stimulate favorable anti-tumor immune responses [Zitvogel et al. 1998]. Also, exosomes can first be isolated, and then tailored to incorporate certain therapeutic or enhanced targeting molecules using a number of techniques [Johnsen et al. 2014]. However, these methods have significant limitations for in vivo applications and variability with regard to cargo loading [Johnsen et al. 2014].

The cell membrane has a critical role in intercellular communication because the cell membrane is the interface between individual cells and their external environment. A number of critical cellular events, including signal transduction, membrane compartmentalization and endosomal trafficking, are coordinated in lipid rafts. Lipid rafts are complex membrane domain structures that are characterized by an excess of cholesterol, sphingolipids, and proteins [Lingwood et al. 2010; Simons et al. 2010]. Scavenger receptor type B-1 (SR-B1) is one of the many receptors that are expressed in lipid rafts [Umemoto et al. 2013]. Because of this, tumor progression is often associated with an increased expression of SR-B1 aiding in the procurement of cholesterol needed for maintaining cell membrane integrity and other cellular processes [Gabitova et al. 2014]. Beyond cholesterol metabolism, modulating lipid raft cholesterol content inhibits downstream second messenger signaling events such as ERK 1/2 signaling which have been reported as critical for exosome uptake. As a result, nanostructures that can change the cell membrane by associating with lipid rafts or binding receptors in the cell membrane, such as SR-B1, may be useful for therapeutic, diagnostic, or research purposes.

Synthetic nanostructures have been shown to be useful for therapeutic, diagnostic, and research purposes. For example, nanostructures having a corona of nucleic acids extending radially from the center have been shown to be useful for inhibiting gene expression (as described in International Patent Publication No. WO/2006/6138145 entitled "Nucleic acid functionalized nanoparticles for therapeutic applications," filed 8 Jun. 2006), nanostructures having a detectable marker have be shown to be useful for detecting intracellular targets in living cells (as described in International Patent Publication No. WO/2008/098248 entitled "Particles for detecting intracellular targets," filed 11 Feb. 2008), and nanostructures having the size, shape, surface chemical composition, and cholesterol binding properties of natural, mature spherical HDL have been shown to be useful for sequestering cholesterol for the treatment of diseases or conditions involving abnormal lipid levels or cholesterol metabolism (as described in International Patent Publication No. WO/2009/131704 entitled, "Nanostructures suitable for sequestering cholesterol and other molecules," filed 24 Apr. 2009 and International Patent Publication No. WO/2013/126776 entitled, "Nanostructures for treating cancers and other conditions," filed 22 Feb. 2013), all publications incorporated herein by reference in its entirety for all purposes. Although International Patent Publication No. WO/2009/131704 describes the use of nanostructures for treating cancers generally and International Patent Publication No. WO/2013/126776 describes the use of nanostructure for treating cancer cells having an SR-B1 receptor, neither publication describes the use of nanostructures to modulate or monitor intercellular communication. Although it was known that SR-B1 could bind synthetic nanostructures and that the binding of the nanostructures may lead to apoptosis of certain cell types, e.g. lymphoma, it was not known that SR-B1 binding of a nanostructure in a viable cell would exhibit modulated intercellular communication. It was unexpected, therefore, that nanostructures such as those described herein could be used for the treatment, diagnosis, or research of vesicle-mediated diseases, as the role of these particles in modulating vesicle uptake or release was not envisioned.

To improve upon current methods, there exists a need for in the art for nanostructures useful for the treatment and diagnosis of vesicle-mediated diseases and conditions and for research in intercellular communication processes generally. Inhibiting intercellular communication may be effective for slowing or halting vesicle-mediated diseases. Moreover, nanostructures that can associate with vesicles may be able to be specifically delivered to specific sites for therapeutic, diagnostic, or research purposes.

SUMMARY OF THE INVENTION

The present invention generally relates to nanostructures and compositions for modulating intercellular communication processes for research, diagnostic and/or therapeutic purposes. One aspect of the invention is a synthetic nanostructure vesicle complex comprising a vesicle, the vesicle having a surface-bound receptor, and a synthetic nanostructure, wherein the synthetic nanostructure is bound to the surface-bound receptor. In some embodiments, the synthetic nanostructure comprises a nanostructure core, a shell, the shell comprising a lipid layer surrounding and attached to the nanostructure core, and a protein associated with the shell. In certain embodiments, the synthetic nanostructure further comprises a diagnostic agent. In particular embodiments, the diagnostic agent is a tracer lipid. In particular embodiments, the tracer lipid comprises a chromophore, a biotin subunit, or both a chromophore and a biotin subunit. In some embodiments, the synthetic nanostructure further comprises a therapeutic agent. In certain embodiments, the therapeutic agent is a nucleic acid, antiviral agent, antineurological agent, or antirheumatologic agent. In some embodiments, the vesicle is an exosome, a virus, an apoptotic body, a synthetic lipid particle, a bacteria, or a fungus. In some embodiments, the surface-bound receptor is SR-B1.

Another aspect of the invention is a method for preparing the synthetic nanostructure vesicle complex, the method comprising contacting a cell or a vesicle with a synthetic nanostructure to prepare a synthetic nanostructure vesicle complex, the complex comprising a vesicle, the vesicle having a surface-bound receptor, and the synthetic nanostructure, wherein the synthetic nanostructure is bound to the surface-bound receptor. In some embodiments, the cell is contacted with the synthetic nanostructure, the surface-bound receptor is bound on the surface of the cell, the cell synthetic nanostructure is taken up by the cell, and the cell secrets the complex. In other embodiments, the vesicle is contacted with the synthetic nanostructure and the surface-bound receptor is bound on the surface of the vesicle. In some embodiments, the cell or the vesicle is contacted with the synthetic nanostructure ex vivo or in vitro. In other embodiments, the cell or the vesicle is contacted with the synthetic nanostructure in vivo. In some embodiments, the method further comprising administering a therapeutically effective amount of the synthetic nanostructure to a patient having a vesicle-mediated disorder. In certain embodiments, the vesicle-mediate disorder is a cancer, a viral infection, a neurological disorder, a rheumatic disease, an immunological disorder, inflammation, antigen presentation, a blood disorder, or a bacterial infection. In some embodiments, the synthetic nanostructure comprises a therapeutic agent. In some embodiments, the method further comprising isolating the complex, detecting the complex, or both isolating the complex and detecting the complex. In some embodiments, the complex is isolated by centrifugation at less than 90,000×g. In some embodiments, the synthetic nanostructure comprises a diagnostic agent.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

FIG. 1A shows characterization of A375 melanoma exosomes: size, morphology and molecular markers. Specifically, FIG. 1A shows a transmission electron micrograph (TEM) of A375 exosomes isolated by differential ultracentrifugation. The isolated exosomes display typical cup-shaped morphology (scale bar=50 nm).

FIG. 1B shows a dynamic light scattering graph displaying the expected exosome size (20-100 nm hydrodynamic diameter).

FIG. 1C shows characterization of A375 melanoma exosomes: size, morphology and molecular markers. Specifically, FIG. 1C shows a western blot demonstrating the enrichment of CD81, a member of the tetraspanin family and exosomal marker [Zoller 2009], in exosome fraction. Additionally, western blotting reveals the absence of the Golgi marker protein 130 (GM 130) demonstrating that prepared exosomes are devoid of components of cellular organelles. Finally, the western blot shows SR-B1 presence in the A375 cell lysate and in exosomes.

FIG. 2A shows pie charts show the content of free cholesterol and cholesteryl ester to hHDL and HDL NPs before (left) and after (right) cholesterol efflux assay in A375 melanoma cells.

FIG. 2B shows $^3$H-cholesterol efflux from A375 cells to HDL NPs (500 nM, final) or hHDL (500 nM, final) measured with and without BLT-1 treatment (1 µM).

FIG. 2C shows cells fractionated using Focus™ Global Fractionation (G Biosciences). Western blot shows SR-B1 enrichment in lipid rafts, presence in exosomes, and absence in the cytoplasmic cell fraction.

FIG. 2D shows A375 cells expressing a GFP-SR-B1 fusion protein stained with an Alexafluor-647 conjugated CTx-B (red) to label and image lipid rafts.

FIG. 2E shows A375 melanoma cell lipid rafts stained with an Alexafluor-488 conjugated CTx-B after treatment with 20 nM DiD-labeled HDL NPs.

FIG. 2F shows A375 melanoma cells expressing a GFP-SR-B1 fusion protein were treated with DiD labeled HDL NPs (20 nM).

Figure 4:
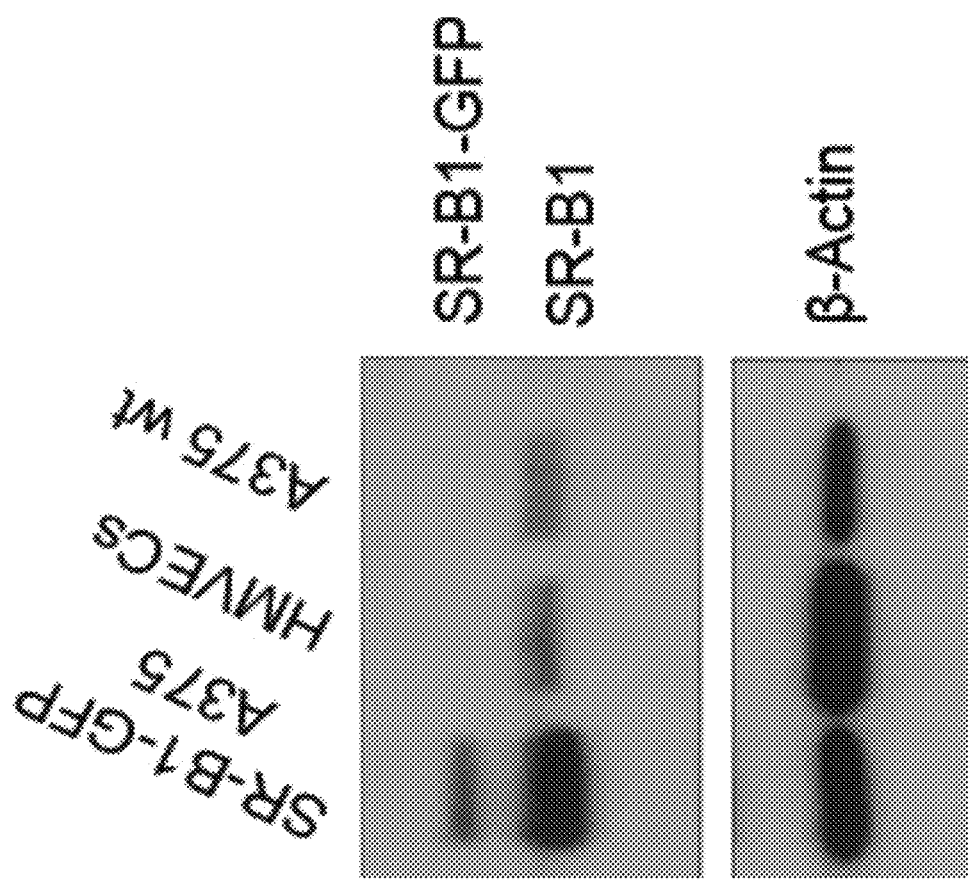

FIG. 4 shows expression of SR-B1 and GFP-SR-B1 in A375 cells and HMVECs. Western blot shows for SR-B1 in both A375 cells and HMVECs using an anti-SR-B1 monoclonal antibody. Note: GFP-SR-B1 fusion protein, characterized by increased molecular weight in A375 cells transfected with appropriate construct (lane 1).

Figure 5A:
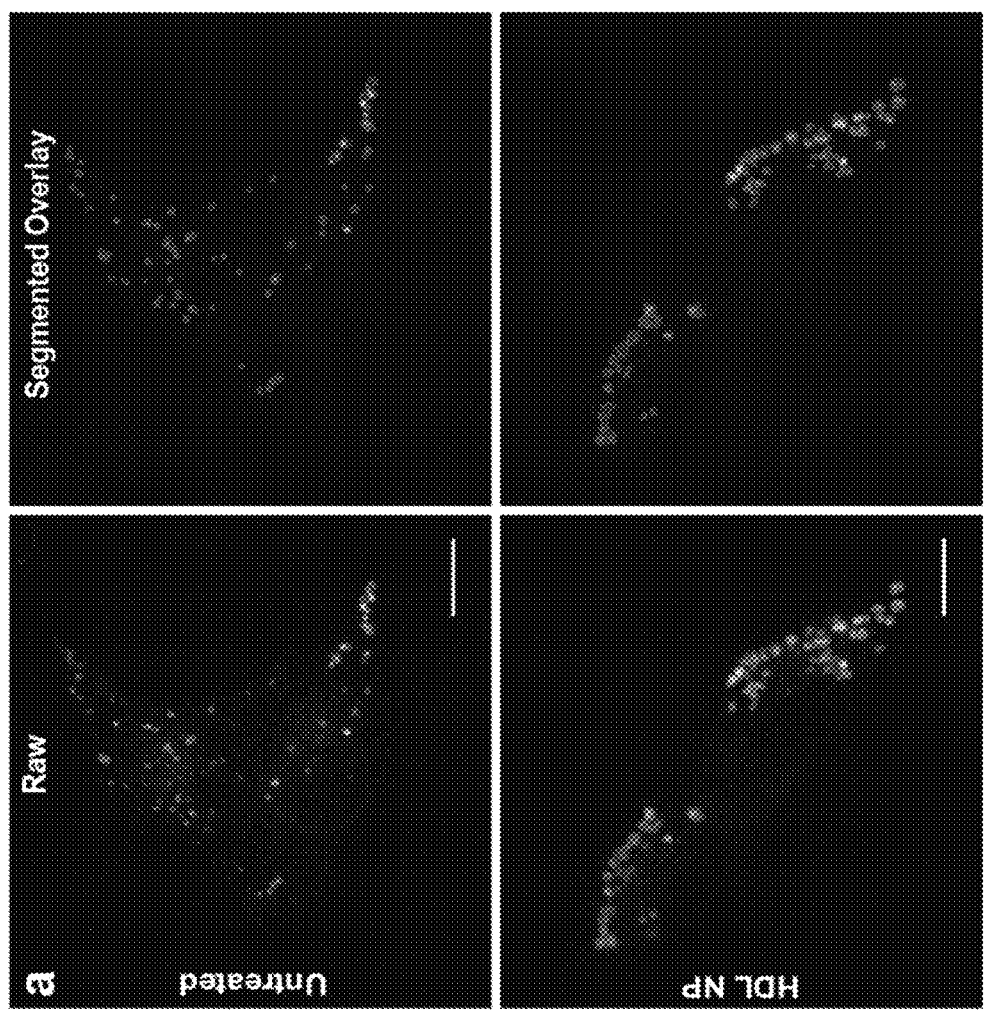

FIG. 5A shows clustering of SR-B1 following HDL NP treatment. Time-lapse images of A375 melanoma cells expressing GFP-SR-B1 were taken in the presence (HDL NP) and absence (i.e. untreated, labeled in the figure as "untx") of HDL NPs (30 nM) 24 hours after treatment. Specifically, FIG. 5A shows representative confocal images of GFP-SR-B1 expressing cells under indicated experimental conditions. Raw images (left) were segmented using a wavelet-based method (see Materials and Methods) to define and measure GFP-SR-B1-positive domains. Outlines of detected clusters are superimposed over the original raw to demonstrate the robustness of segmentation approach used for automatic detection and tracking of the GFP-SR-B1 containing domains (right; scale bar=10 μm). For each condition, six time-lapse movies (2 minute duration, 1 s lapse) were acquired with n≥15 cells/condition.

FIG. 5B shows clustering of SR-B1 following HDL NP treatment. Time-lapse images of A375 melanoma cells expressing GFP-SR-B1 were taken in the presence (HDL NP) and absence (i.e. untreated, labeled in the figure as "untx") of HDL NPs (30 nM) 24 hours after treatment. Specifically, FIG. 5B shows the distribution of areas for all domains present in the first image of each series (* p≤0.05 via permutation t-test) presented as box plots. Median, the 25th and 75th percentile are shown. Whiskers extend between the 10th and the 90th percentile.

FIG. 5C shows clustering of SR-B1 following HDL NP treatment. Time-lapse images of A375 melanoma cells expressing GFP-SR-B1 were taken in the presence (HDL NP) and absence (i.e. untreated, labeled in the figure as "untx") of HDL NPs (30 nM) 24 hours after treatment. Specifically, FIG. 5C shows the average domain brightness per domain: increased brightness in the presence of HDL NPs suggests elevated SR-B1 concentration per area (* p<0.05 via permutation t-test).

FIG. 5D shows clustering of SR-B1 following HDL NP treatment. Time-lapse images of A375 melanoma cells expressing GFP-SR-B1 were taken in the presence (HDL NP) and absence (i.e. untreated, labeled in the figure as "untx") of HDL NPs (30 nM) 24 hours after treatment. Specifically, FIG. 5D shows the average number of GFP-SR-B1 domains per cell for the indicated conditions. Note significantly reduced number of GFP-SR-B1 containing domains per cell as upon HDL NP treatment. (***P<0.00005 via permutation t-test).

Figure 6A:
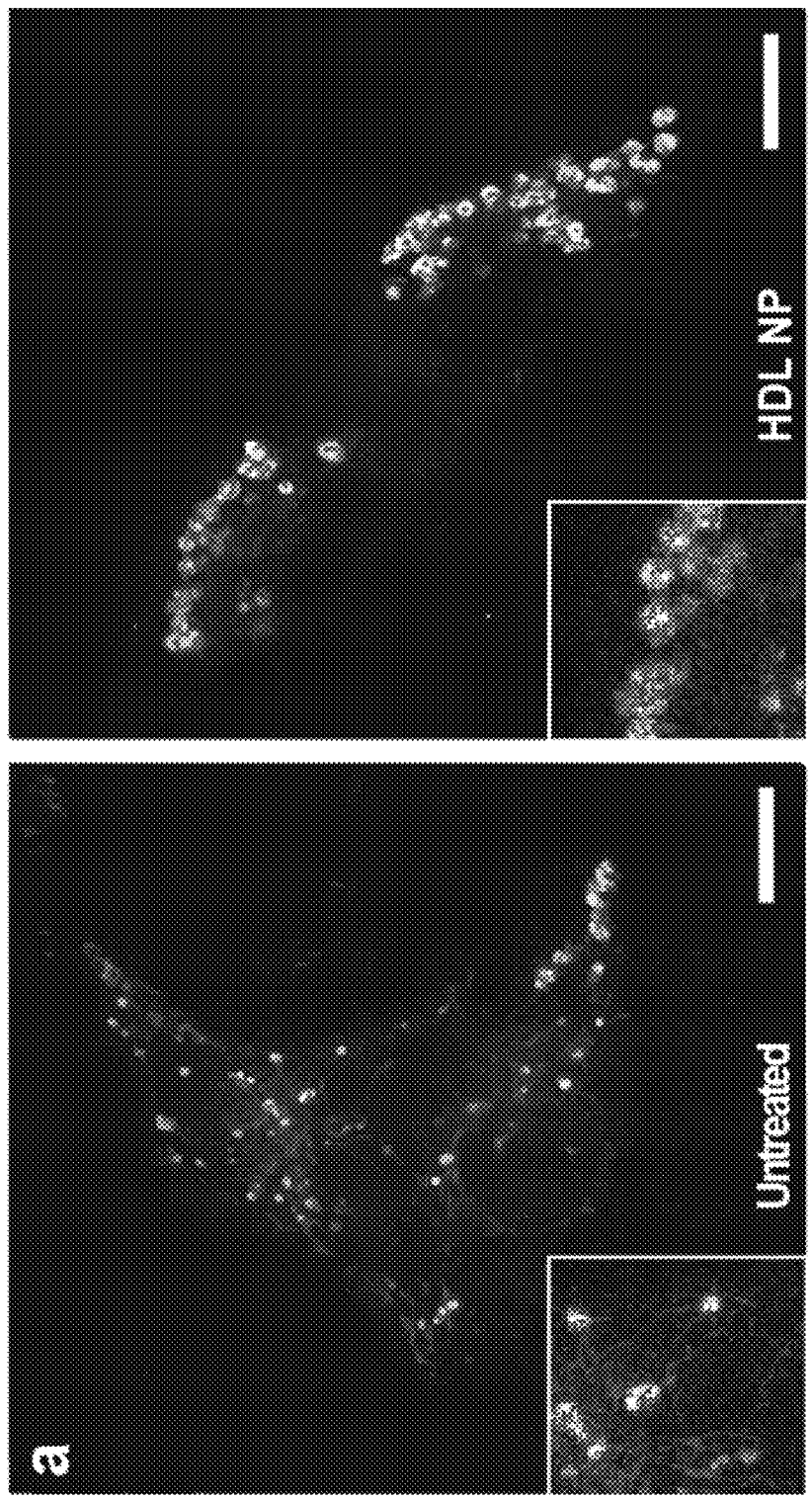

FIG. 6A shows HDL NPs lead to reduced mobility and dispersion of SR-B1 containing domains. Time-lapse confocal imaging (is intervals) was used to visualize the dynamics of SR-B1 containing domains. Individual domains were detected and tracked as described below. Specifically, FIG. 6A shows motion tracks from the entire duration of imaging overlaid on a single snapshot from the series (untreated cells, left, or HDL NP treatment, right). Insets provide higher magnification images of selected areas with multiple tracks (scale bar=10 μm).

Figures 6B, 6C:
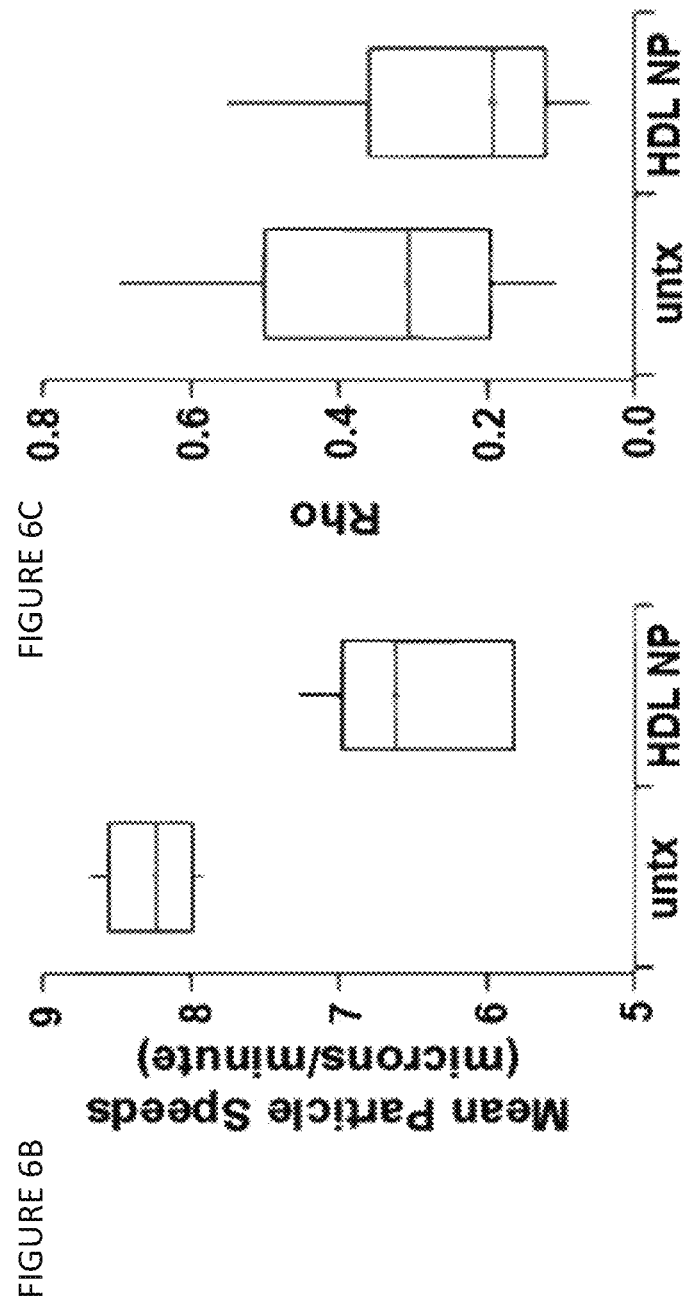

FIG. 6B shows HDL NPs lead to reduced mobility and dispersion of SR-B1 containing domains. Time-lapse confocal imaging (is intervals) was used to visualize the dynamics of SR-B1 containing domains. Individual domains were detected and tracked as described below. Specifically, FIG. 6B shows the average speeds per puncta for each condition (***P<0.00005 via permutation t-test).

FIG. 6C shows HDL NPs lead to reduced mobility and dispersion of SR-B1 containing domains. Time-lapse confocal imaging (is intervals) was used to visualize the dynamics of SR-B1 containing domains. Individual domains were detected and tracked as described below. Specifically, FIG. 6C shows the ratio of net displacement (the straight-line distance from the starting point to the end point) to total track length traveled for each GFP-SR-B1 containing domain (rho). Values near 1 indicate directed motion.

FIG. 7A shows HDL NPs block the uptake of exosomes by A375 melanoma cells treated with 1 μg/mL of DiI-labeled exosomes. Specifically, FIG. 7A shows exosome uptake visualized using fluorescence microscopy after treatment with HDL NP (25 nM, 24 hrs). Actin cytoskeleton was stained using a FITC-phalloidin conjugate and the nuclei were stained with DAPI. The exosome uptake by untreated cells serves as a negative control.

Figure 7C:
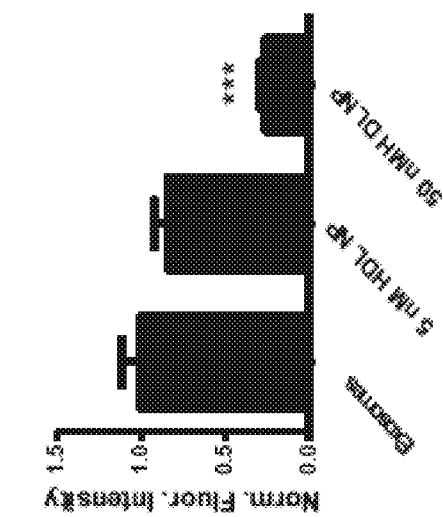
Figure 7B:
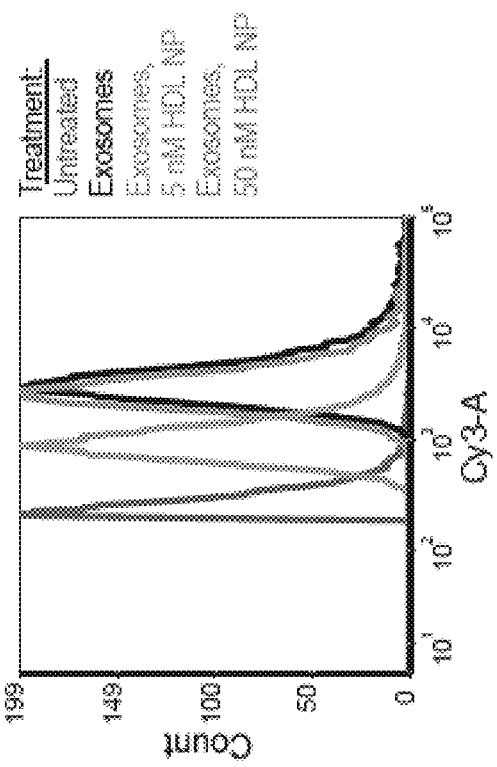

FIG. 7B shows HDL NPs block the uptake of exosomes by A375 melanoma cells treated with 1 μg/mL of DiI-labeled exosomes. Specifically, FIG. 7B shows DiI-labeled exosome uptake by A375 cells with and without HDL NP treatment (5 and 50 nM HDL NP, 24 hrs) was analyzed using flow cytometry. Cells that were not exposed to DiI labeled exosomes were used as a negative control.

FIG. 7C shows HDL NPs block the uptake of exosomes by A375 melanoma cells treated with 1 μg/mL of DiI-labeled exosomes. Specifically, FIG. 7C shows the average fluorescence intensity of A375 cells analyzed by flow cytometry in b, plotted as a bar graph.

Figure 7E:
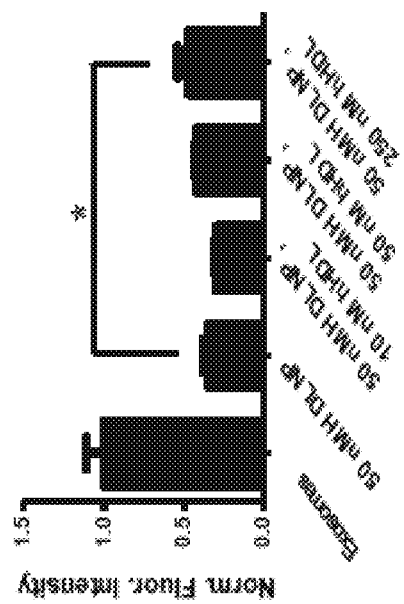
Figure 7D:
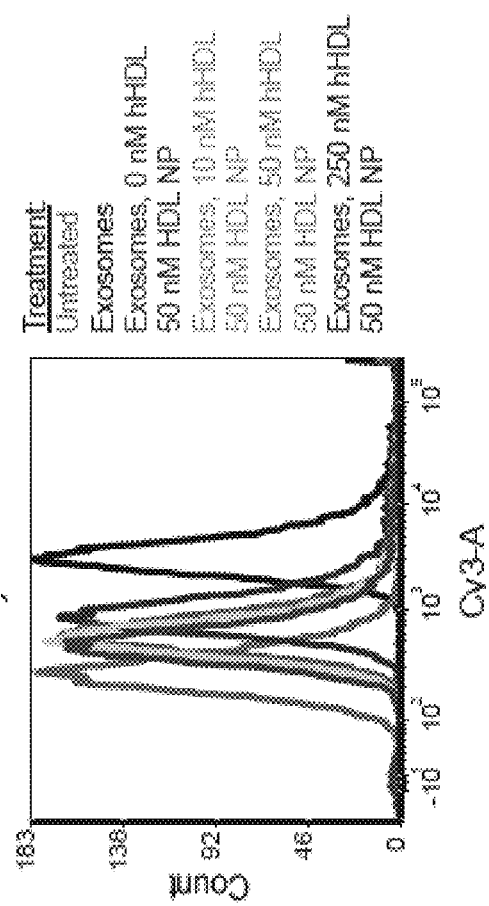

FIG. 7D shows partial rescue of exosome uptake by HDL NPs treatment of A375 cells (50 nM) using hHDL treatment (10, 50, 250 nM).

FIG. 7E shows a box plot of the average fluorescence intensity of A375 cells measured by flow cytometry in FIG. 7D.

Figure 7G:
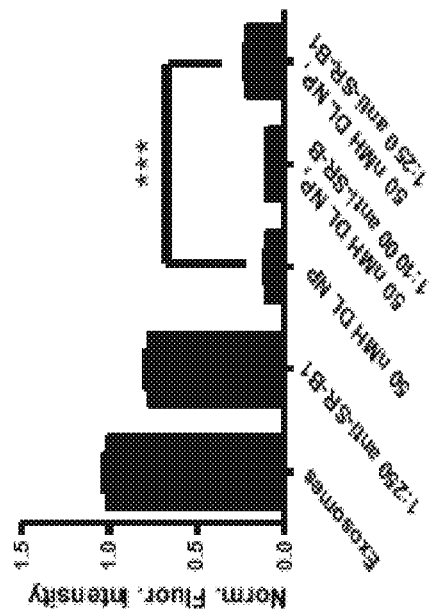
Figure 7F:
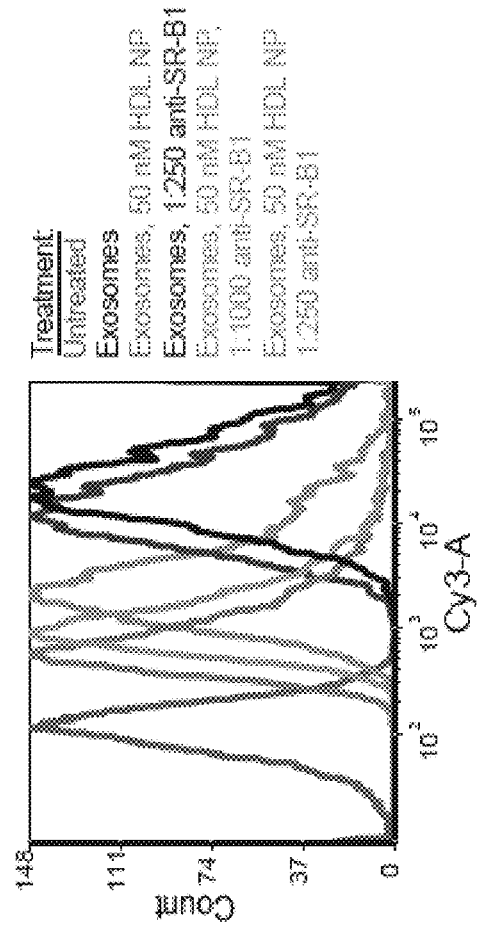

FIG. 7F shows dose dependent recovery of exosome uptake in A375 cells treated with HDL NPs (50 nM, 24 hrs) by anti-SR-B1 antibody.

FIG. 7G shows the average fluorescence intensity of A375 cells analyzed by flow cytometry in FIG. 7E.

Figure 8A:
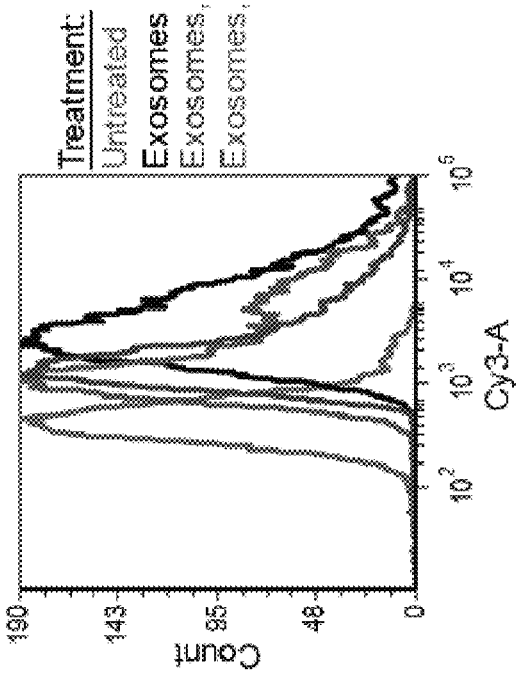

FIG. 8A shows HDL NP treatment inhibits exosome uptake in A375 melanoma cells expressing GFP-SR-B1. A375 cells expressing GFP-SR-B1 were treated with exosomes in the presence of 0, 5, and 50 nM HDL NPs. As was observed for the wild-type (untransfected) A375 cells, exosomes and HDL NP treatment reduces exosome uptake A375 cells expressing GFP-SR-B1. Specifically, FIG. 8A shows flow cytometry analysis of exosome uptake after A375 cell pre-treatment with HDL NP.

Figure 8B:
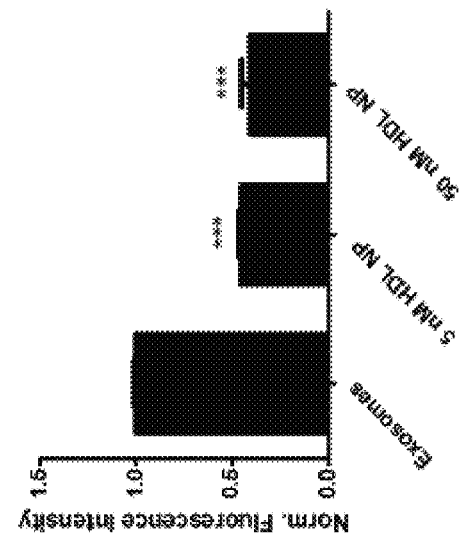

FIG. 8B shows HDL NP treatment inhibits exosome uptake in A375 melanoma cells expressing GFP-SR-B1. A375 cells expressing GFP-SR-B1 were treated with exosomes in the presence of 0, 5, and 50 nM HDL NPs. As was observed for the wild-type (untransfected) A375 cells, exosomes and HDL NP treatment reduces exosome uptake A375 cells expressing GFP-SR-B1. Specifically, FIG. 8B shows the average fluorescence intensity of cells analyzed by flow cytometry. (*** represents P<0.001 as compared to exosome only condition).

Figures 9A, 9B:
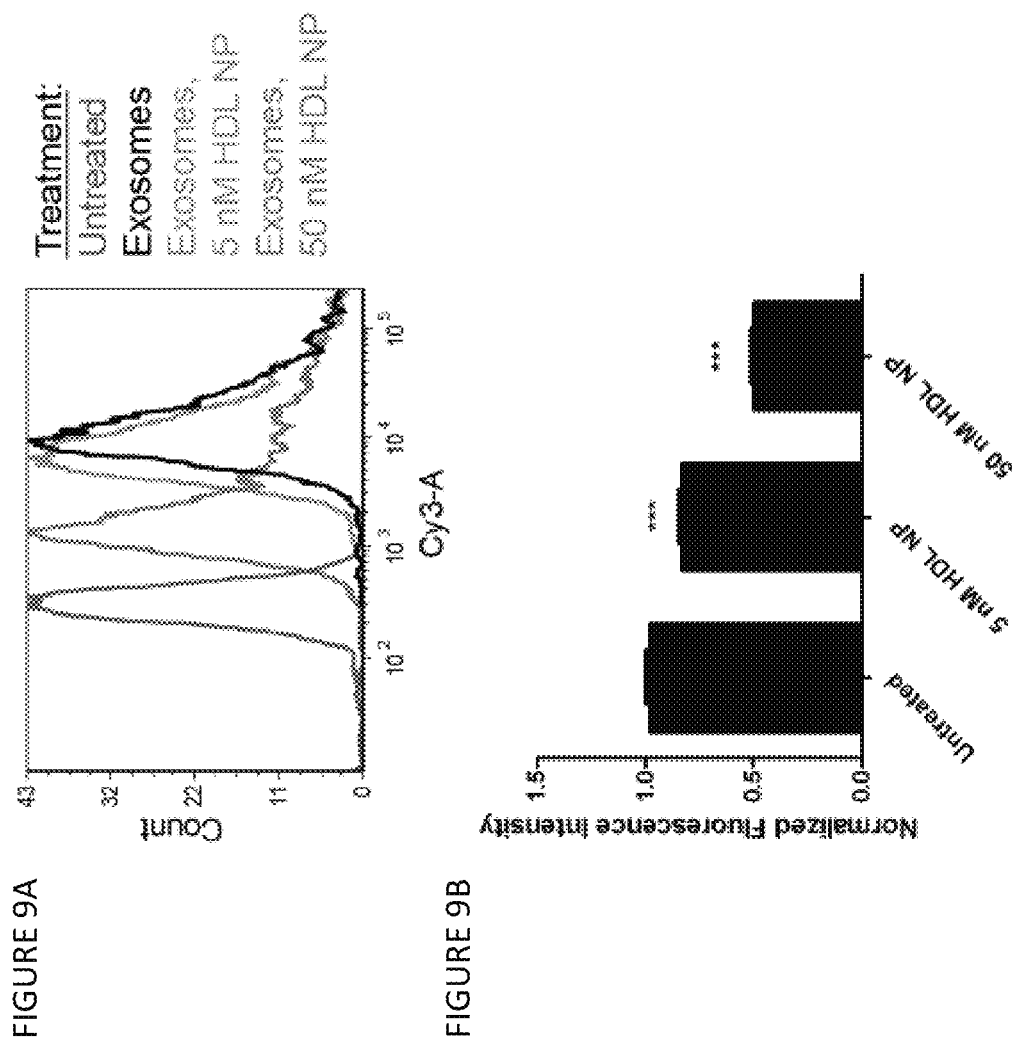

FIG. 9A shows the inhibition of exosome uptake after treatment with HDL NP is not due to extracellular interaction of exosomes and HDL NP. A375 melanoma cells were pre-treated for 12 hours with HDL NP 5 and 50 nM. Excess HDL NPs were then washed 2 times in PBS. Specifically, FIG. 9A shows flow cytometry analysis of exosome uptake after A375 cell pre-treatment with HDL NP.

FIG. 9B shows the inhibition of exosome uptake after treatment with HDL NP is not due to extracellular interaction of exosomes and HDL NP. A375 melanoma cells were pre-treated for 12 hours with HDL NP 5 and 50 nM. Excess HDL NPs were then washed 2 times in PBS. Specifically, FIG. 9B shows the average fluorescence intensity of cells analyzed by flow cytometry. (*** represents P<0.001 as compared to exosome only condition).

Figures 10A, 10B:
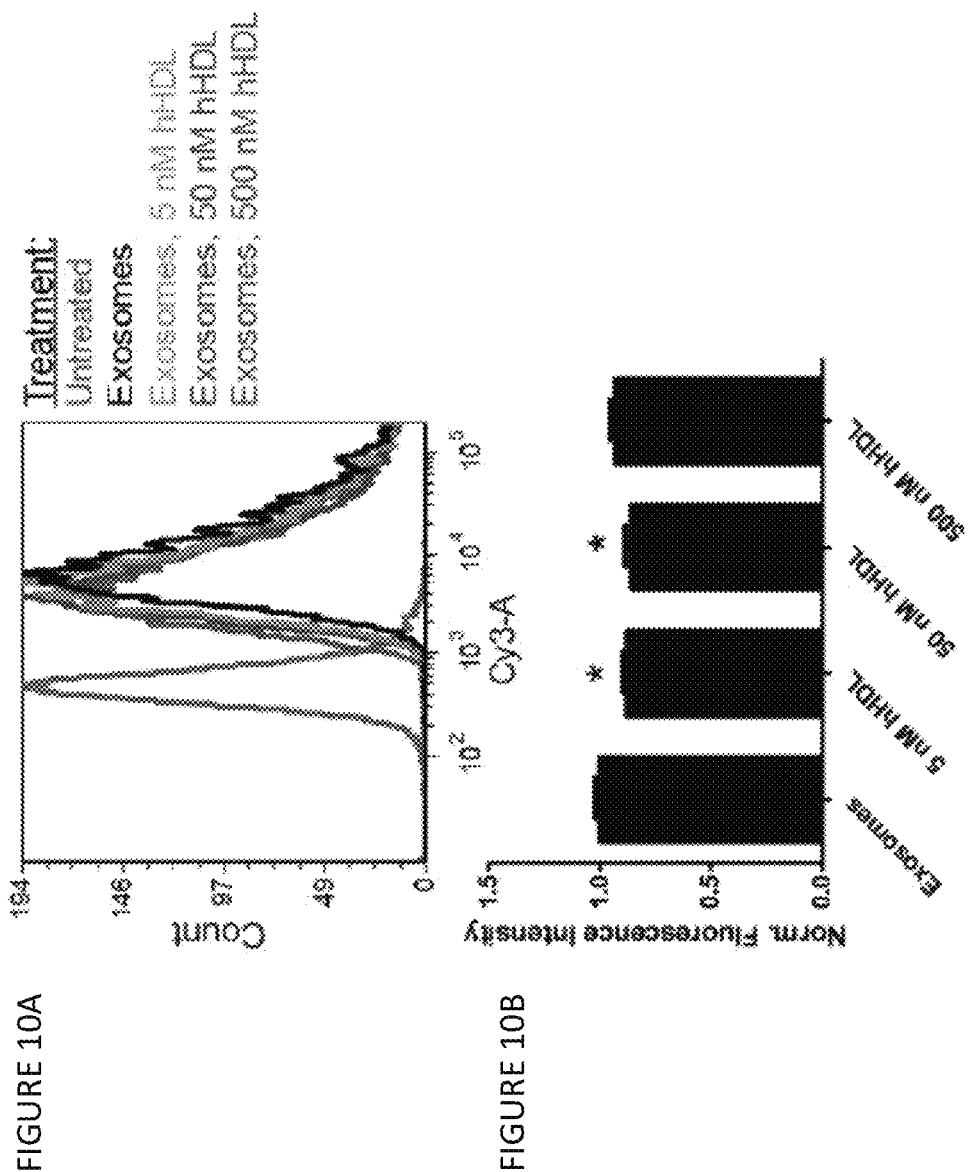

FIG. 10A shows hHDL has only a modest effect on exosome uptake by A375 cells. Exosomes were labeled using DiI and their uptake by A375 cells in the presence of 0, 5, 50, 500 nM hHDL was measured using flow cytometry. In contrast to HDL NP treatment, there the reduction in exosome uptake does not exceed 15%, even at 500 nM hHDL. Specifically, FIG. 10A cytometry analysis of exosome uptake.

FIG. 10B shows hHDL has only a modest effect on exosome uptake by A375 cells. Exosomes were labeled using DiI and their uptake by A375 cells in the presence of 0, 5, 50, 500 nM hHDL was measured using flow cytometry. In contrast to HDL NP treatment, there the reduction in exosome uptake does not exceed 15%, even at 500 nM hHDL. Specifically, FIG. 10B shows the average fluorescence intensity of cells analyzed by flow cytometry. (* represents P<0.05 as compared to exosome only condition).

Figure 11B:
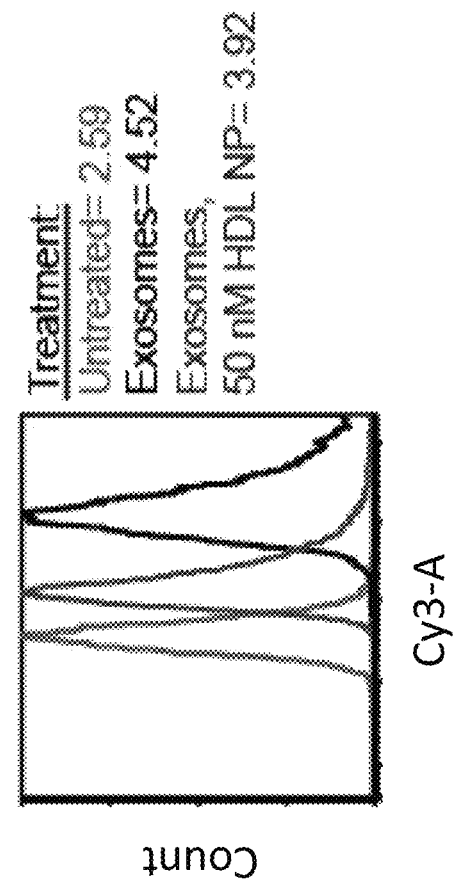
Figure 11A:
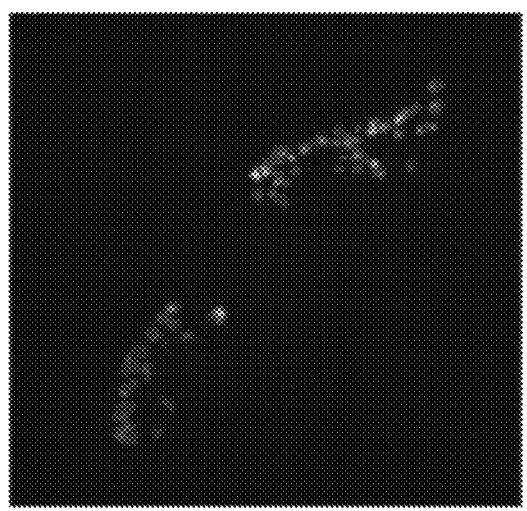

FIG. 11A shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with 50 nM HDL NPs. A representative fluorescence images is shown.

FIG. 11B shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with 50 nM HDL NPs. The mean fluorescent intensity values (log scale) are included next to each histogram.

Figure 11D:
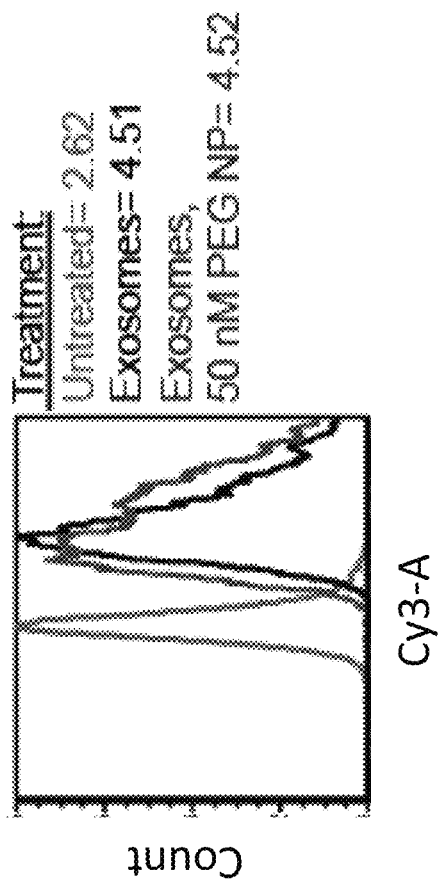
Figure 11C:
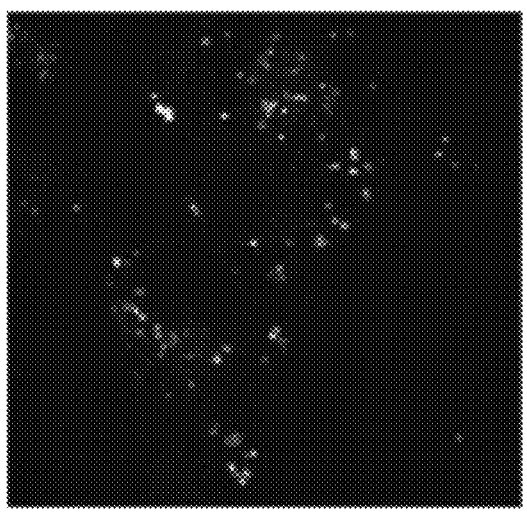

FIG. 11C shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with 50 nM PEG-NPs. A representative fluorescence images is shown.

FIG. 11D shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with 50 nM PEG-NPs. The mean fluorescent intensity values (log scale) are included next to each histogram.

Figure 11F:
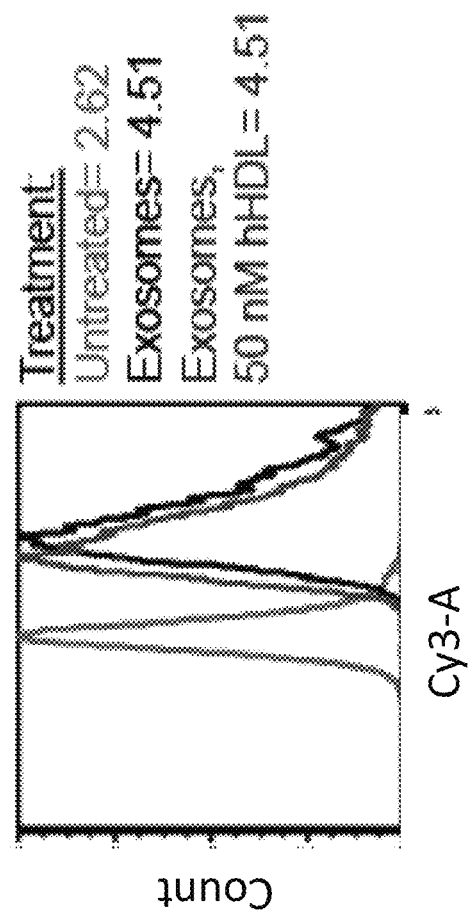
Figure 11E:
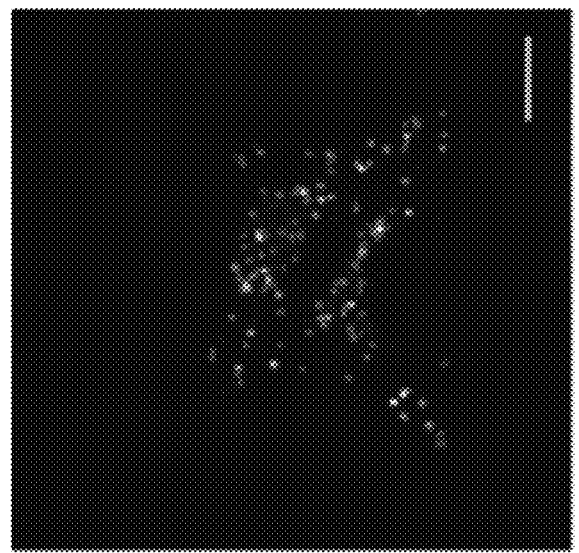

FIG. 11E shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with 50 nM hHDL. A representative fluorescence images is shown.

FIG. 11F shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with 50 nM hHDL. The mean fluorescent intensity values (log scale) are included next to each histogram.

Figure 11H:
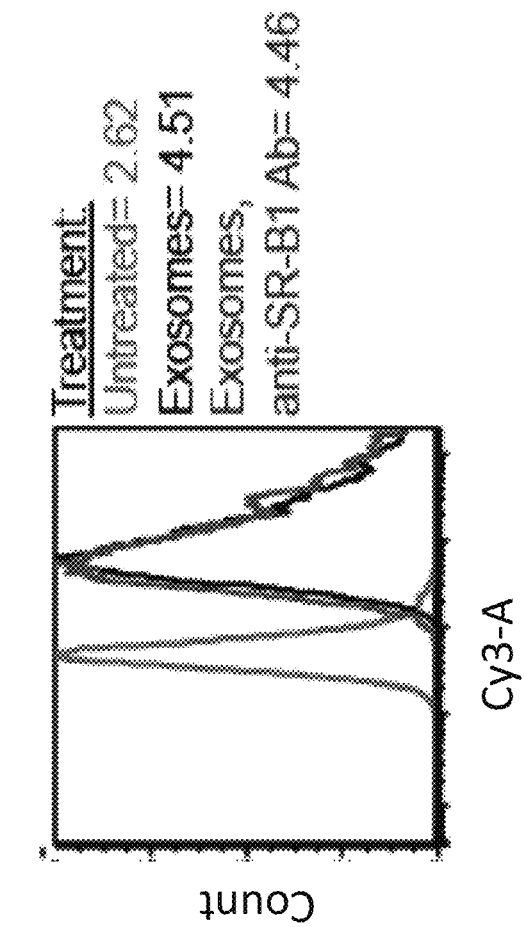
Figure 11G:
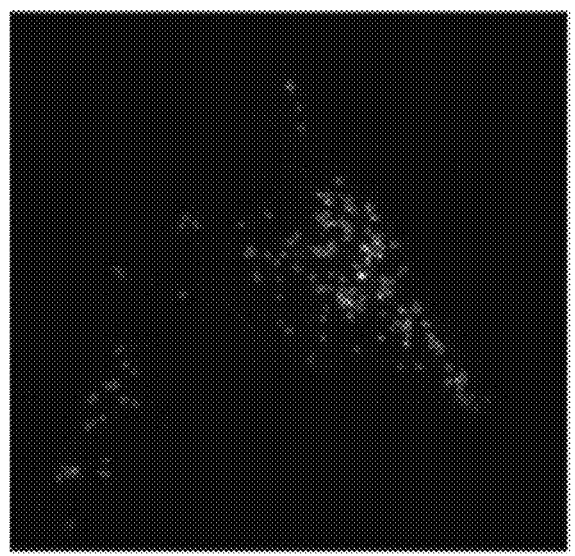

FIG. 11G shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with SR-B1 neutralizing antibody. A representative fluorescence images is shown.

FIG. 11H shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with SR-B1 neutralizing antibody. The mean fluorescent intensity values (log scale) are included next to each histogram.

Figure 11J:
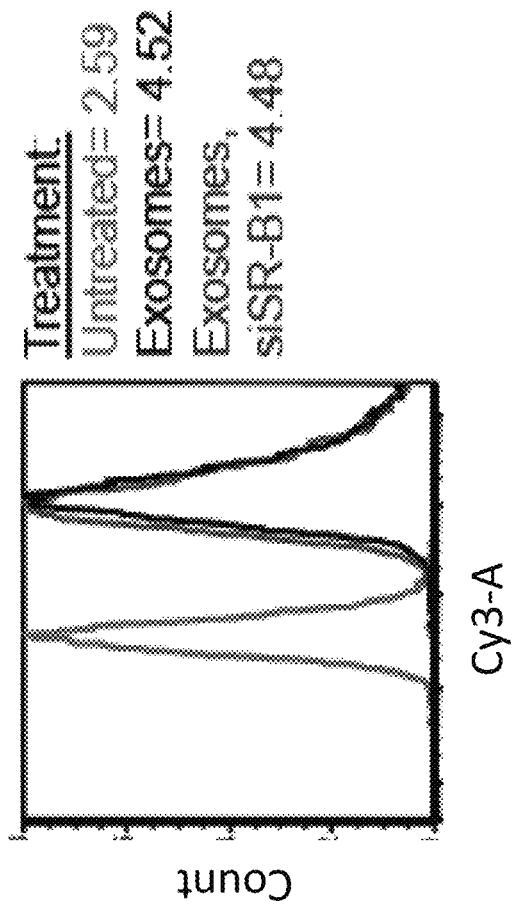
Figure 11I:
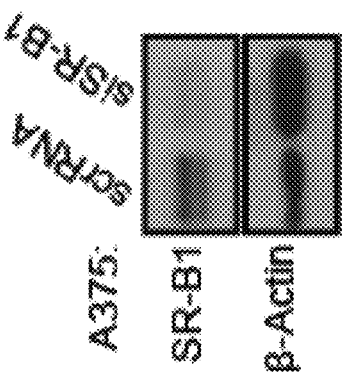

FIG. 11I shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with siRNA targeting SR-B1 expression (siSR-B1). Western blot confirm SR-B1 knockdown.

FIG. 11J shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with siRNA targeting SR-B1 expression (siSR-B1). The mean fluorescent intensity values (log scale) are included next to each histogram.

Figure 11L:
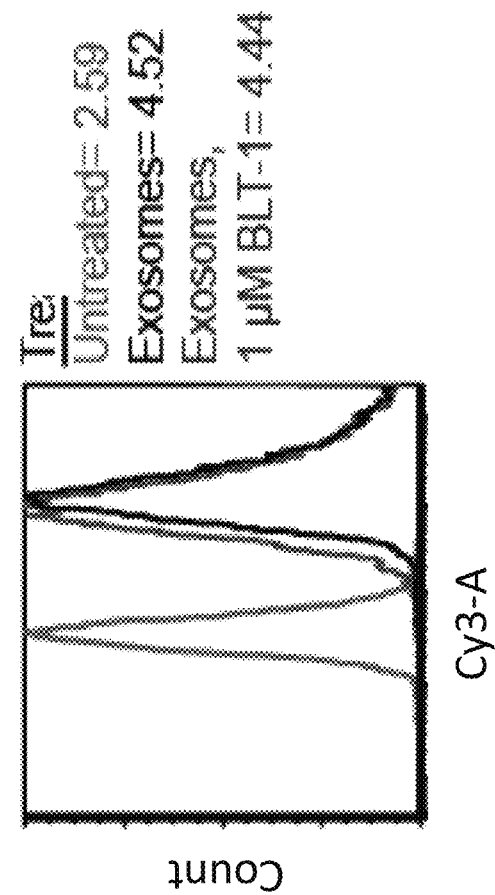
Figure 11K:
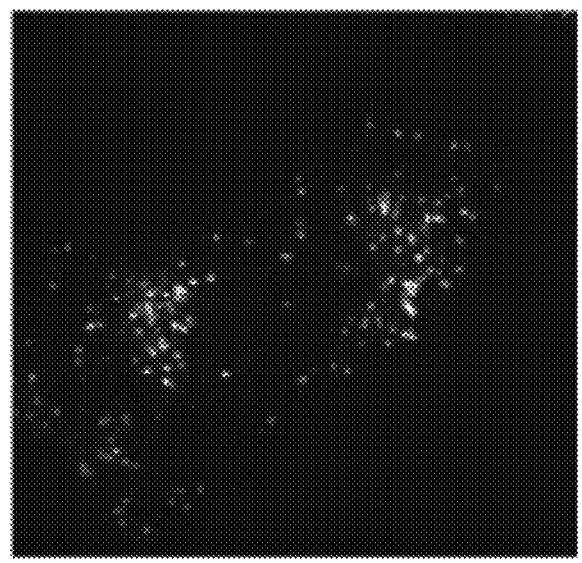

FIG. 11K shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with 1 µM BLT-1. A representative fluorescence images is shown.

Figure 11N:
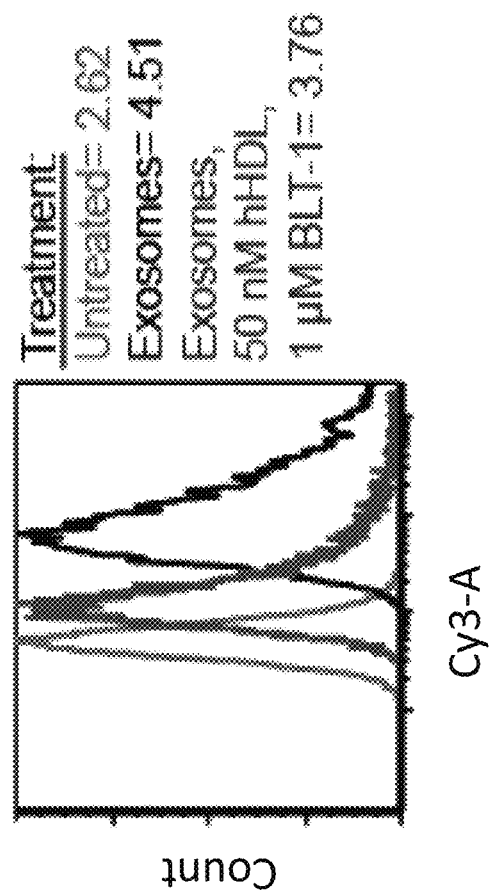
Figure 11M:
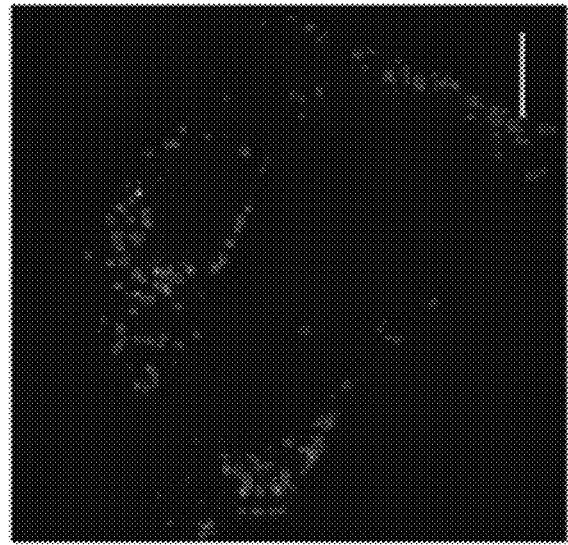

FIG. 11L shows targeting SR-B1 to induce receptor clustering and inhibit exosome uptake. A375 melanoma cells were analyzed for exosome uptake by flow cytometry and clustering of GFP-SR-B1 containing domains was measured using fluorescent microscopy after 24 hrs treatment with the following agents:

FIG. 11M shows the combined treatment of A375 cells with hHDL (50 nM) and BLT-1 (1 µM). A representative fluorescence images is shown.

FIG. 11N shows the combined treatment of A375 cells with hHDL (50 nM) and BLT-1 (1 µM). The mean fluorescent intensity values (log scale) are included next to each histogram.

Figure 11O:
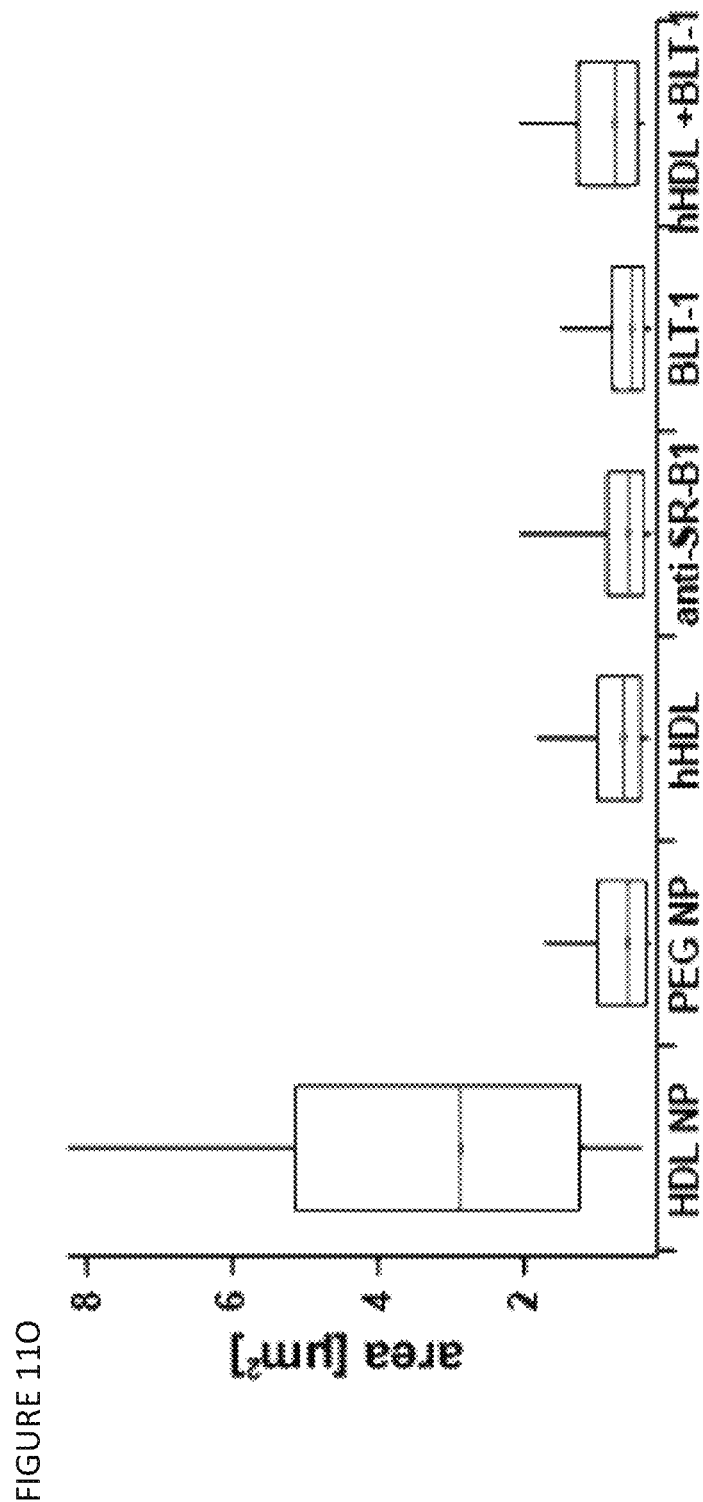

FIG. 11O shows the box plot shows average size of the GFP-SR-B1 positive clusters per experimental condition.

Figures 12A, 12B:
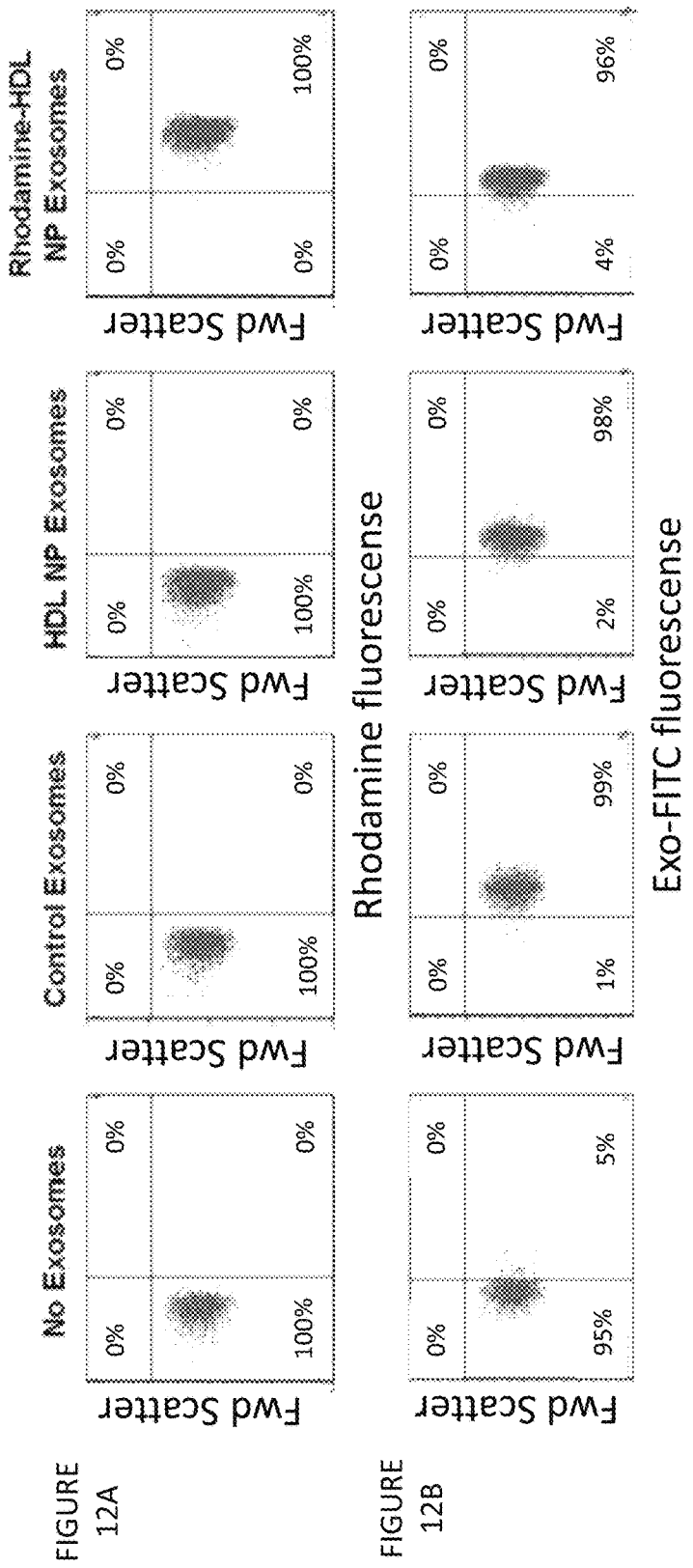

FIG. 12A shows that Rhodamine lipid is present in exosomes treated with Rhodamine HDL NPs.

FIG. 12B shows that Rhodamine lipid is present in exosomes treated with Rhodamine HDL NPs.

Figure 13:
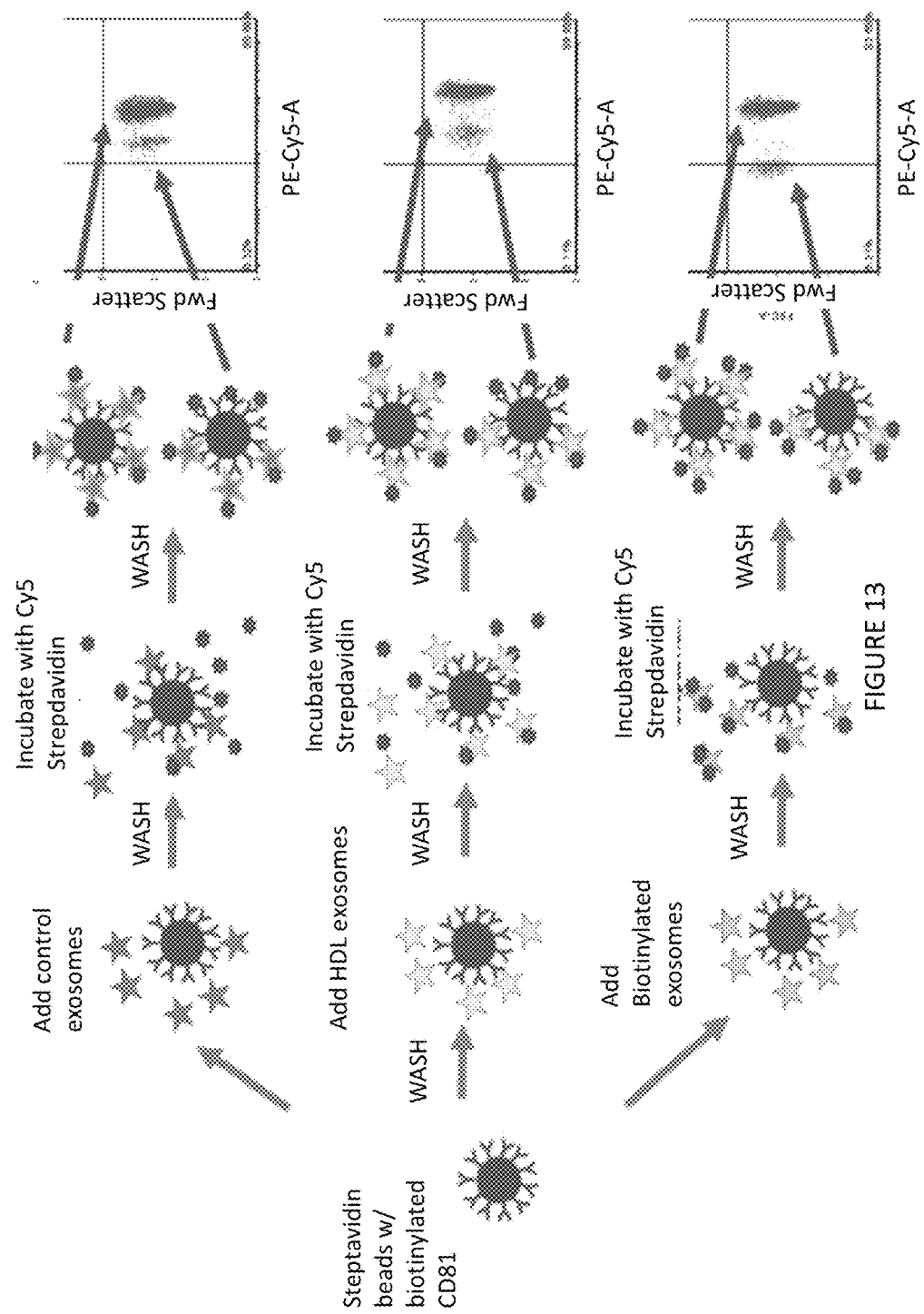

FIG. 13 shows a scheme for identifying biotin presence on membrane of exosomes.

Figure 14B:
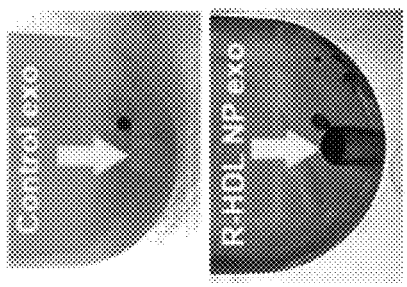
Figure 14A:
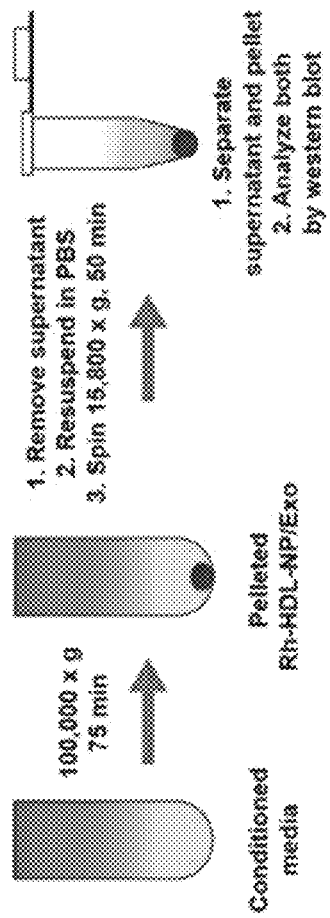

FIG. 14A shows SR-B1 expression in CWR22Rv1 cells and exosomes and Rh-HDL NP association. Specifically, FIG. 14A shows a scheme demonstrating isolation method for exosomes from untreated and Rh-HDL NP treated cells.

FIG. 14B shows SR-B1 expression in CWR22Rv1 cells and exosomes and Rh-HDL NP association. Specifically, FIG. 14B shows an exosome pellet following ultracentrifugation of conditioned media from untreated cells (upper) and cells treated with Rh-HDL NPs (lower).

Figure 14D:
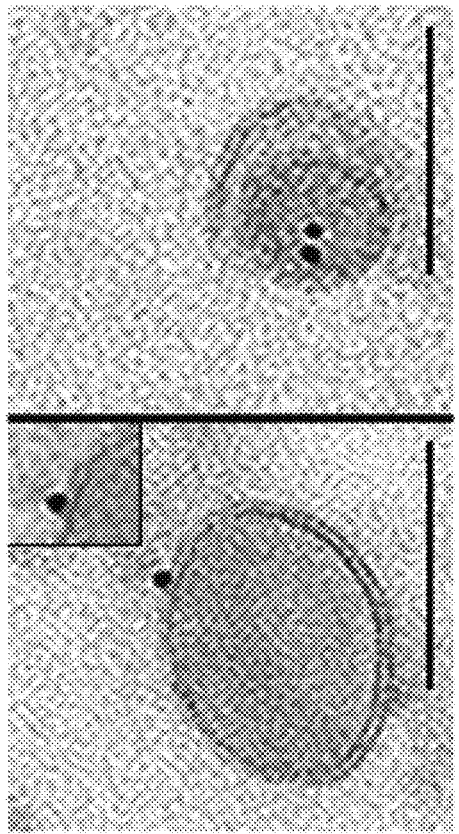
Figure 14C:
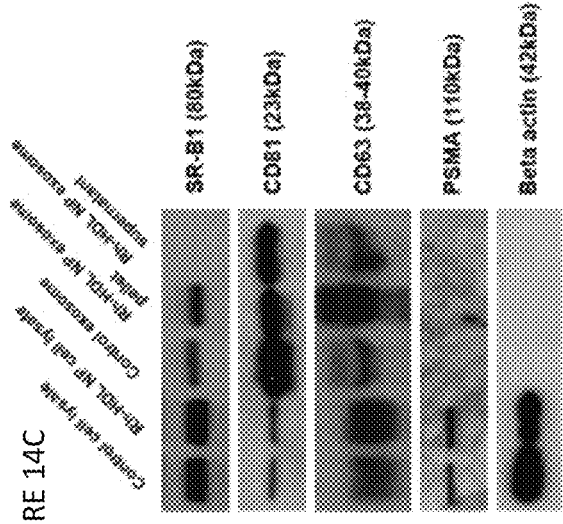

FIG. 14C shows SR-B1 expression in CWR22Rv1 cells and exosomes and Rh-HDL NP association. Specifically, FIG. 14C shows a western blot of cell lysates and exosomes from untreated and Rh-HDL NP treated CWR22Rv1 cells.

FIG. 14D shows SR-B1 expression in CWR22Rv1 cells and exosomes and Rh-HDL NP association. Specifically, FIG. 14D shows a TEM of exosomes from cells treated with Rh-HDL NP (49,000×; inset 98,000×). Scale bar: 100 nm.

FIG. 15A shows detection of CWR22Rv1 cell exosomes using flow cytometry. Specifically, FIG. 15A shows quantification of FITC (total exosome) fluorescence using anti-CD81 ExoFlow beads incubated with exosomes from control (center bar) or Rh-HDL NP (right bar) treated cells. *(P<0.001), **(P=0.03). A two-tailed t-test was used to determine significance.

FIG. 15B shows detection of CWR22Rv1 cell exosomes using flow cytometry. Specifically, FIG. 15B shows rhodamine fluorescence was quantified on the same set of beads used in FIG. 15A. * p=0.0182. A two-tailed t-test was used to determine significance.

FIG. 15C shows ExoFITC fluorescence was measured after anti-rhodamine beads were utilized to isolate Rh-HDL NP exosomes. *(P=0.029), (P=0.007), *(P=0.05), ****(P=0.001). A two-tailed t-test was used to determine significance.

FIG. 15D shows the same exosomes as in FIG. 15C analyzed for rhodamine fluorescence. *(P=0.018), (P=0.013), *(P=0.034), ****(P=0.024). A two-tailed t-test was used to determine significance.

FIG. 15E shows direct flow cytometry of filtered PBS.

FIG. 15F shows direct flow cytometry of Rh-HDL NP.

FIG. 15G shows direct flow cytometry of CWR22Rv1-GFP exosomes (upper left box).

FIG. 15H shows direct flow cytometry of Rh-HDL NP exosomes (upper right box).

FIG. 15I shows direct flow cytometry of APC anti-CD81 antibody alone (control)

FIG. 15J shows direct flow cytometry of CD81 antibody and Rh-HDL NP (control).

FIG. 15K shows direct flow cytometry of CD81+/GFP+ exosomes (upper right box).

FIG. 15L shows direct flow cytometry of CD81+/Rh+ exosomes (upper right box).

FIG. 16A shows knockdown of SR-B1 in A375 melanoma cells reduces Rh-HDL NP labeling of exosomes. Specifically, FIG. 16A shows CD81+/Rh+ exosomes (upper right gate) isolated from GFP-SR-B1 A375 conditioned media by ultracentrifugation.

FIG. 16B shows knockdown of SR-B1 in A375 melanoma cells reduces Rh-HDL NP labeling of exosomes. Specifically, FIG. 16B shows CD81+/Rh+ exosomes (upper right gate) in conditioned media from GFP-SR-B1 A375 cells treated with control siRNA.

FIG. 16C shows knockdown of SR-B1 in A375 melanoma cells reduces Rh-HDL NP labeling of exosomes. Specifically, FIG. 16C shows CD81+/Rh+ exosomes (upper right gate) in conditioned media from GFP-SR-B1 A375 cells treated with siRNA to SR-B1.

FIG. 16D shows knockdown of SR-B1 in A375 melanoma cells reduces Rh-HDL NP labeling of exosomes. Specifically, FIG. 16D shows Quantification of CD81+/Rh+ events normalized to total CD81+ events in control and anti-SR-B1 siRNA treated cells (n=4/group). Statistical significance determined using Mann-Whitney U test. *(P=0.0286).

Figure 17A:
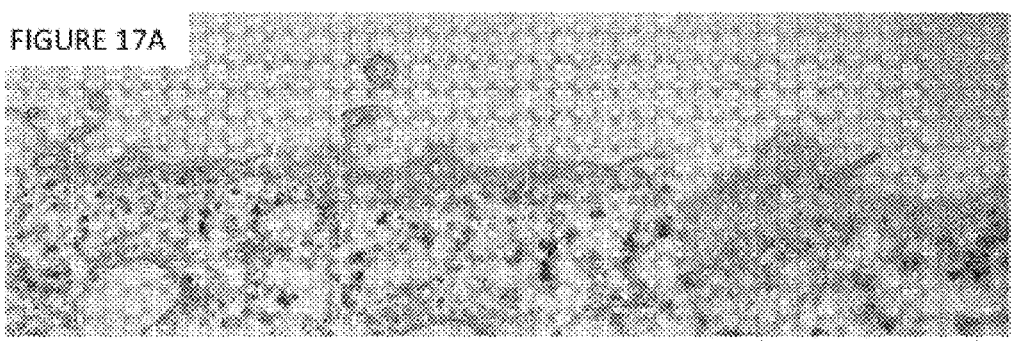

FIG. 17A shows visualization of Rh-HDL NPs after addition to cells by TEM. Specifically, FIG. 17A shows Rh-HDL NP on the cell membrane at 2 hours (red arrows). Left to right: 18,500×, 30,000×, 68,000×.

Figure 17B:
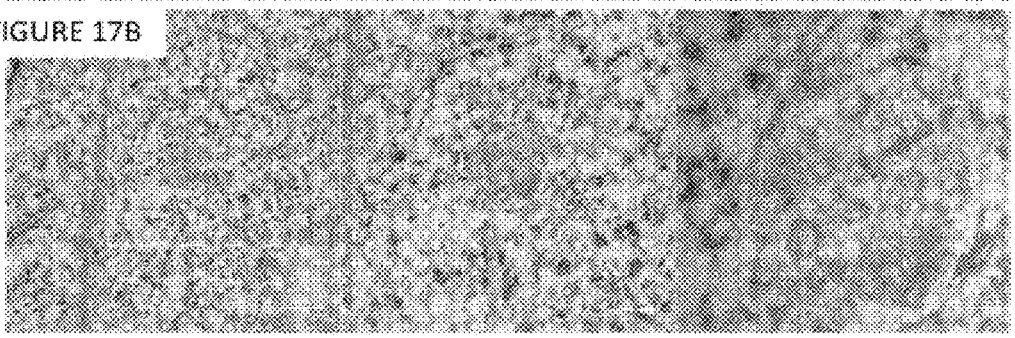

FIG. 17B shows visualization of Rh-HDL NPs after addition to cells by TEM. Specifically, FIG. 17B shows Rh-HDL NP on the inner membrane of an early endosome-like structure. Left to right: 11,000×, 23,000×, 68,000×.

Figure 17C:
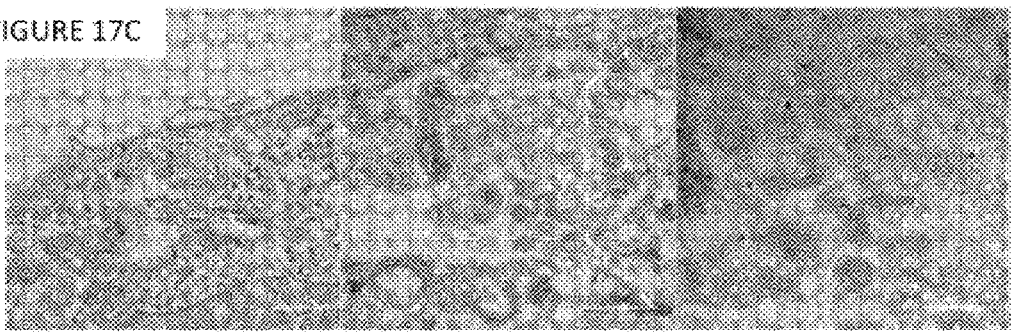

FIG. 17C shows visualization of Rh-HDL NPs after addition to cells by TEM. Specifically, FIG. 17C shows Rh-HDL NP on the outer membrane of microvesicles within a multivesicular body-like structure. Left to right: 13,000×, 23,000×, 49,000×. For each panel, scale bars are 500 nm, 200 nm, and 50 nm from left to right.

Figure 18A:
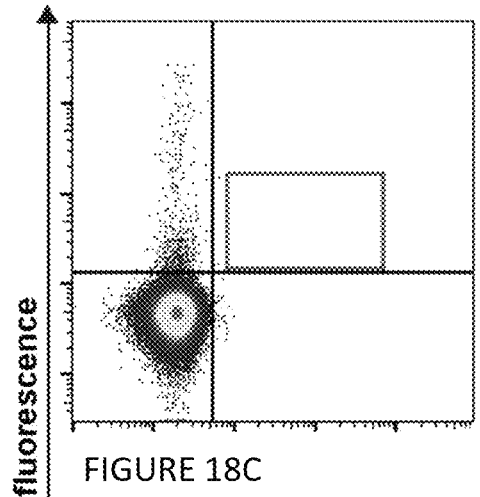

FIG. 18A shows detection of Rh-HDL NP labeled exosomes spiked into human serum. Direct flow cytometry of human serum incubated with anti-CD81 antibody. Specifically, FIG. 18A shows anti-CD81 antibody alone.

Figure 18B:
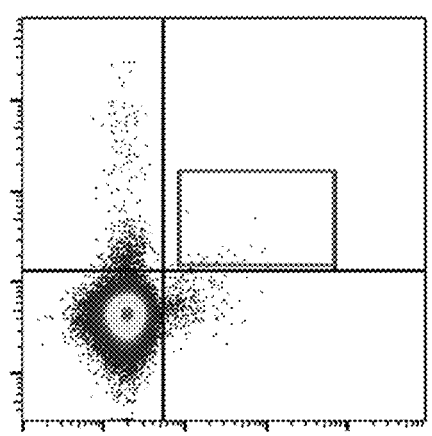

FIG. 18B shows detection of Rh-HDL NP labeled exosomes spiked into human serum. Direct flow cytometry of human serum incubated with anti-CD81 antibody. Specifically, FIG. 18B shows exosomes from A375 cells after Rh-HDL NP treatment at 0.1 ng/μL after a 24-hour incubation.

Figure 18C:
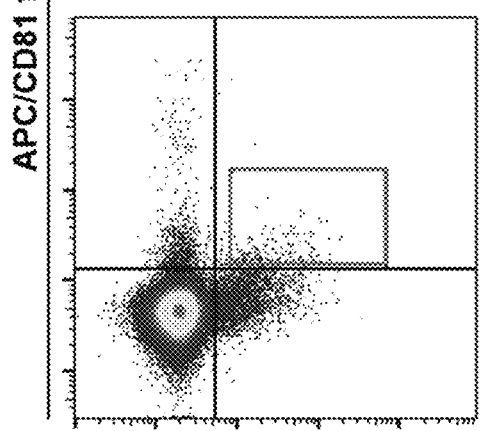

FIG. 18C shows detection of Rh-HDL NP labeled exosomes spiked into human serum. Direct flow cytometry of human serum incubated with anti-CD81 antibody. Specifically, FIG. 18C shows 1 ng/μL after a 24-hour incubation.

Figure 18D:
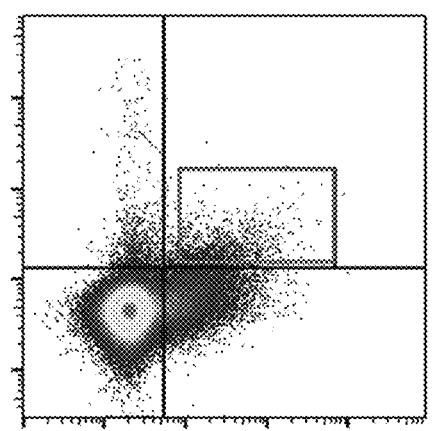

FIG. 18D shows detection of Rh-HDL NP labeled exosomes spiked into human serum. Direct flow cytometry of human serum incubated with anti-CD81 antibody. Specifically, FIG. 18D shows 4 ng/μL after a 24-hour incubation.

Figure 18E:
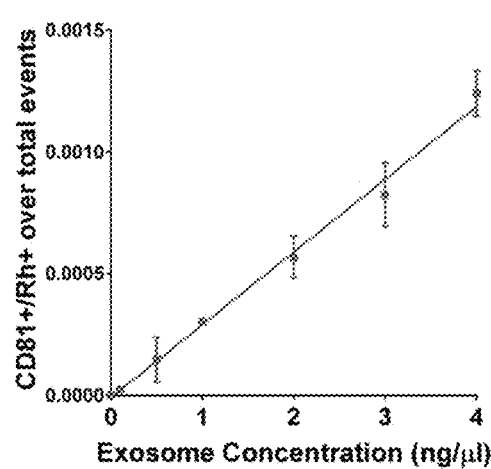

FIG. 18E shows quantification of CD81+/Rh+ events normalized to total events (n=3/point, r2=0.9778).

Figure 18F:
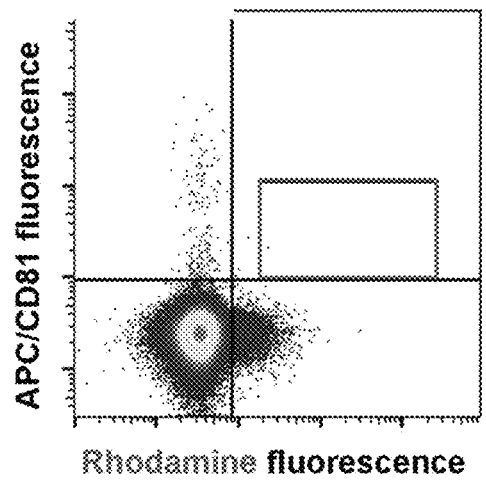

FIG. 18F shows Rh-HDL NPs incubated in serum from a healthy individual and stained with anti-CD81 antibody.

Figure 19A:
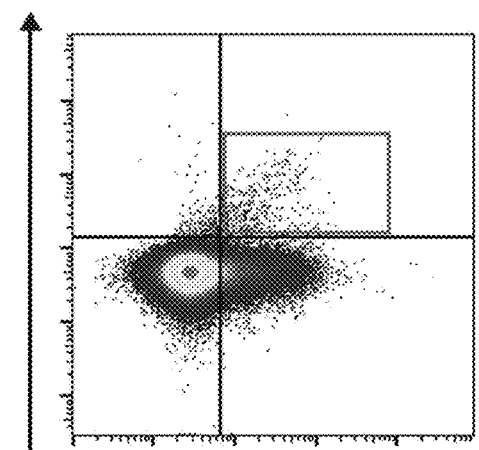

FIG. 19A shows detection of Rh+ exosomes in serum from human patients with melanoma. Specifically, FIG. 19A shows flow cytometry of A375 exosomes isolated from untreated cells then incubated with Rh-HDL NP and stained with APC anti-CD81.

Figure 19B:
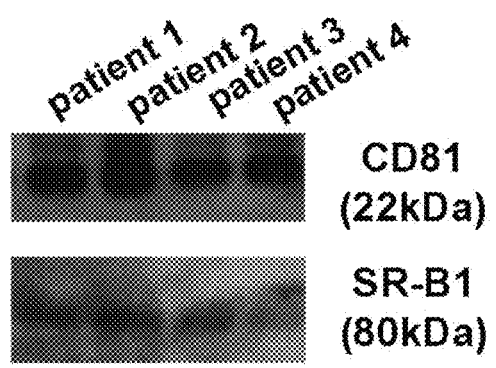

FIG. 19B shows detection of Rh+ exosomes in serum from human patients with melanoma. Specifically, FIG. 19B shows a western blot of isolated serum exosomes from human patients with melanoma.

Figure 19C:
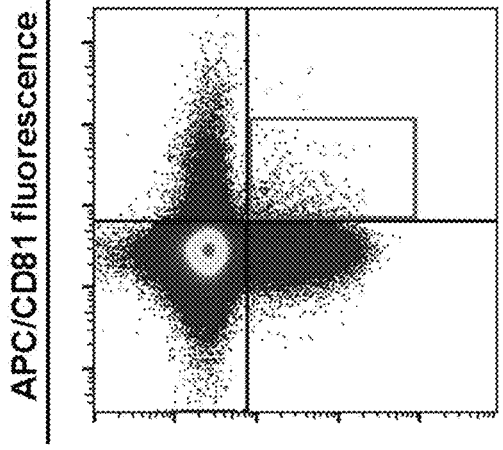

FIG. 19C shows detection of Rh+ exosomes in serum from human patients with melanoma. Specifically, FIG. 19C shows flow cytometry of serum from human melanoma patients incubated with Rh-HDL NP. Plots are in the same order as loaded on the western blots in FIG. 6B and FIG. 6G.

Figure 19D:
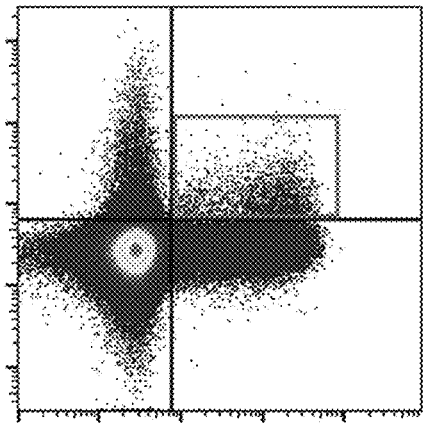

FIG. 19D shows detection of Rh+ exosomes in serum from human patients with melanoma. Specifically, FIG. 19D shows flow cytometry of serum from human melanoma patients incubated with Rh-HDL NP. Plots are in the same order as loaded on the western blots in FIG. 6B and FIG. 6G.

FIG. 19E shows detection of Rh+ exosomes in serum from human patients with melanoma. Specifically, FIG. 19E shows flow cytometry of serum from human melanoma patients incubated with Rh-HDL NP. Plots are in the same order as loaded on the western blots in FIG. 6B and FIG. 6G.

FIG. 19F shows detection of Rh+ exosomes in serum from human patients with melanoma. Specifically, FIG. 19F shows flow cytometry of serum from human melanoma patients incubated with Rh-HDL NP. Plots are in the same order as loaded on the western blots in FIG. 6B and FIG. 6G.

FIG. 19G shows detection of Rh+ exosomes in serum from human patients with melanoma. Specifically, FIG. 19G shows a western analysis of Rh-HDL NPs isolated following incubation with human serum samples.

FIG. 20A shows cellular uptake of Rh-HDL NP labeled exosomes. Specifically, FIG. 20A shows DiO fluorescence of A375 cells after 2 hours of exosome treatment. *($P \leq 0.0427$). Statistical significance was determined by a two-tailed t-test. Error bars are ±standard deviation.

FIG. 20B shows cellular uptake of Rh-HDL NP labeled exosomes. Specifically, FIG. 20B shows rhodamine fluorescence of A375 cells after 2 hours of exosome treatment. *($P=0.0094$). Statistical significance was determined by a two-tailed t-test. Error bars are ±standard deviation.

FIG. 20C shows cellular uptake of Rh-HDL NP labeled exosomes. Specifically, FIG. 20C shows DiO fluorescence of A375 cells after 2 hours of exosome treatment. *($P<0.005$), **($P=0.0161$). Statistical significance was determined by a two-tailed t-test. Error bars are ±standard deviation.

FIG. 20D shows cellular uptake of Rh-HDL NP labeled exosomes. Specifically, FIG. 20D shows rhodamine fluorescence of A375 cells after 2 hours of exosome treatment. *($P=0.002$). n=3 each sample. Statistical significance was determined by a two-tailed t-test. Error bars are ±standard deviation.

Figure 21:
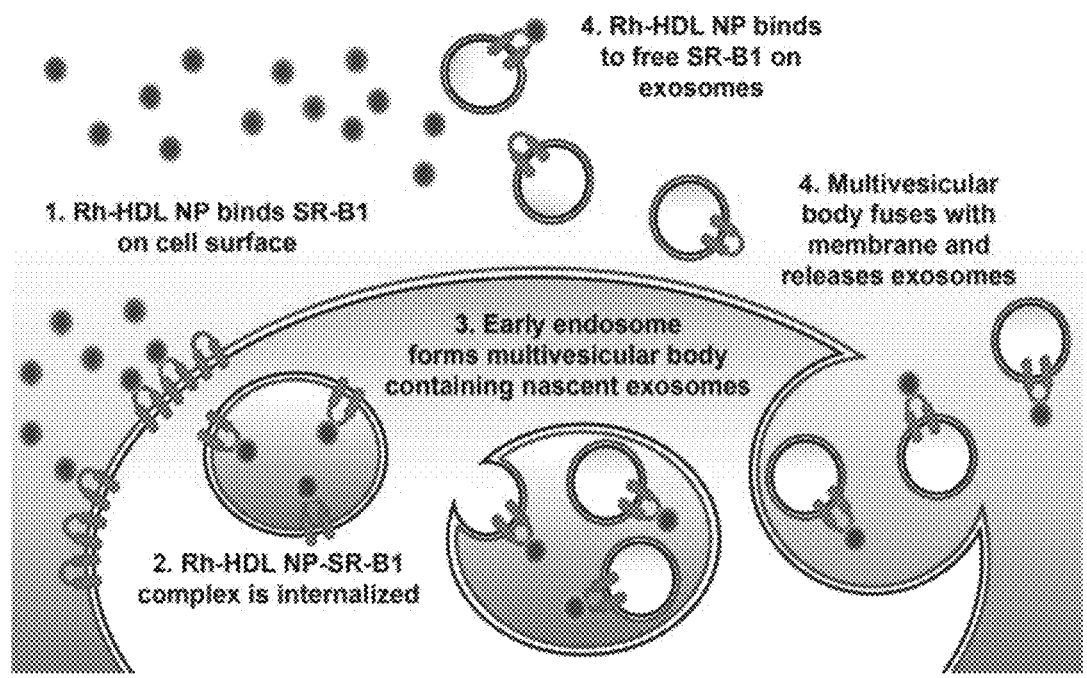

FIG. 21 shows a scheme for Rh-HDL NP binding and exosome labeling. Rh-HDL NPs may label exosomes by two pathways: binding of SR-B1 on the cell surface resulting in internalization and incorporation into exosomes at time of synthesis or binding of SR-B1 in free exosomes after secretion from the parent cell.

Figure 22A:
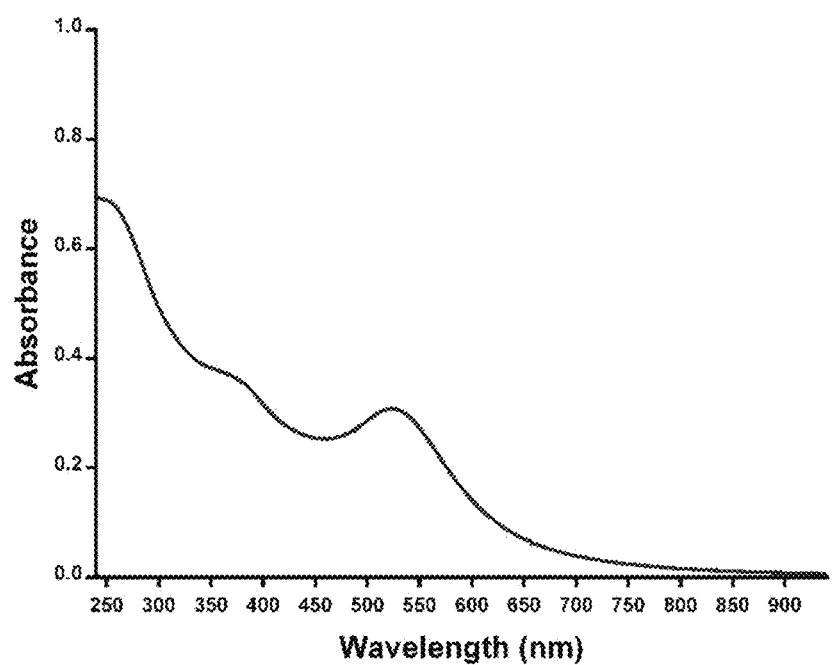

FIG. 22A shows a UV-Vis spectrum of HDL NP showing characteristic surface plasmon for gold nanoparticles at 520 nm.

Figure 22B:
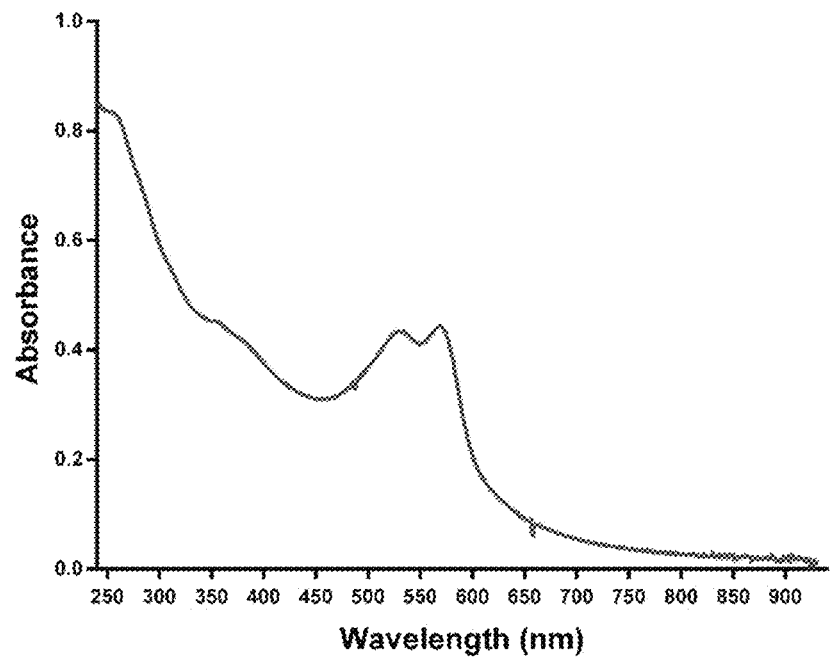

FIG. 22B shows a UV-Vis spectrum of Rh-HDL NP, demonstrating an additional absorbance peak at 560 nm, corresponding to the rhodamine fluorophore.

Figure 23:
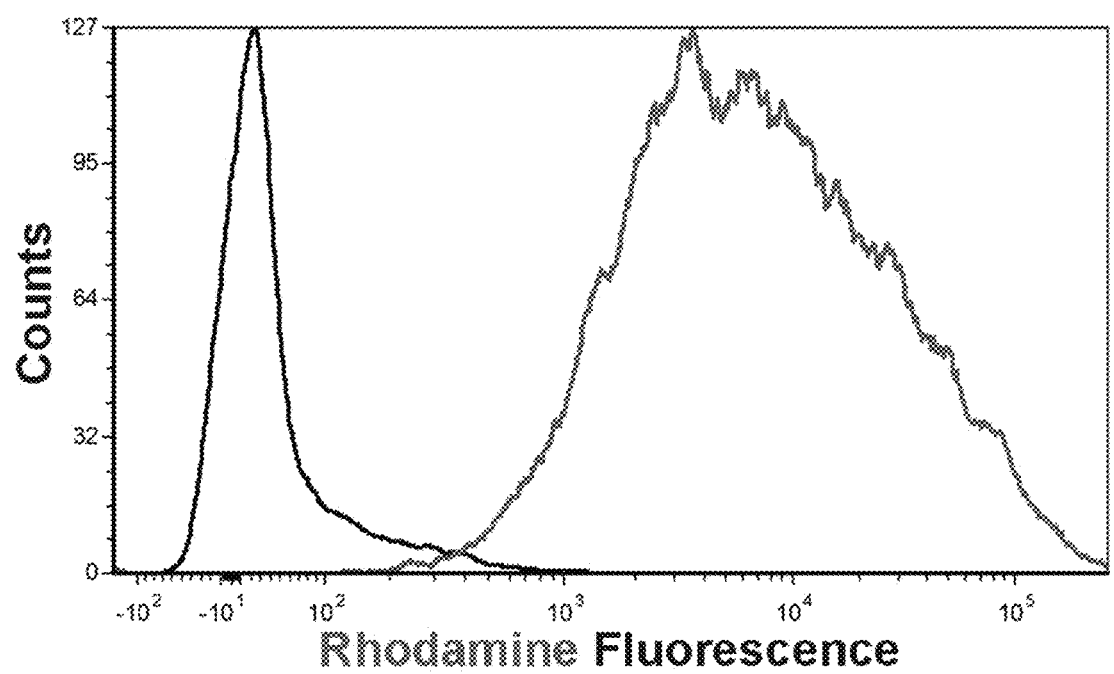

FIG. 23 shows Rh-HDL NP uptake by CWR22Rv1 cells. Histogram of rhodamine fluorescence from untreated cells (left) and cells incubated with 20 nM Rh-HDL NP (right).

Figure 24:
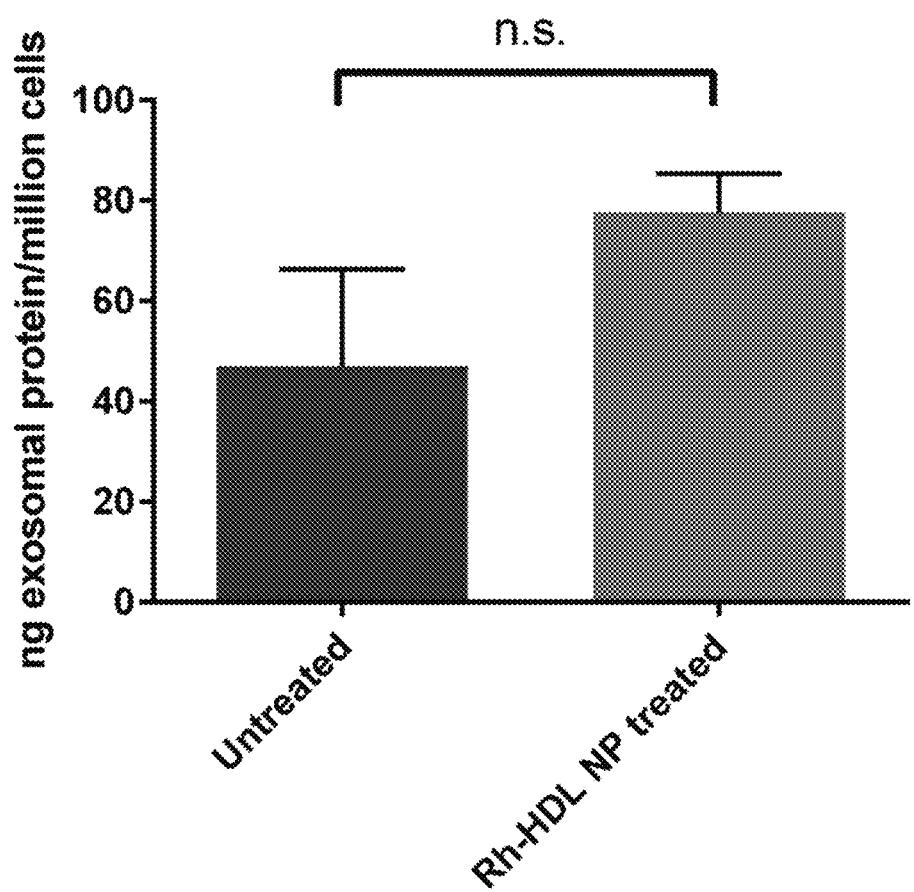

FIG. 24 shows exosome production by CWR22Rv1 cells. Untreated cells and Rh-HDL NP treated cells do not produce statistically different amounts of exosomal protein ($P=0.22$).

Figure 25:
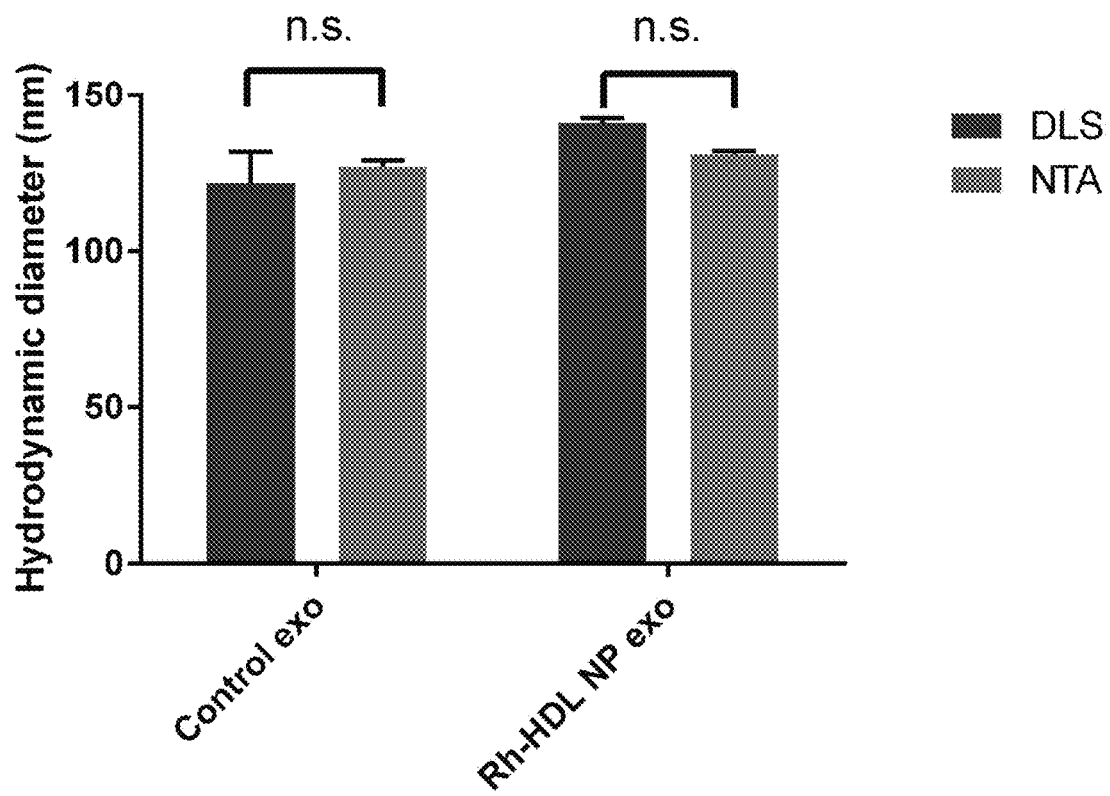

FIG. 25 shows exosome size measured by DLS and NTA. The hydrodynamic diameter of exosomes from untreated control (left) and Rh-HDL NP treated cells (right) was determined by DLS (left bar) and NTA (right bar) and found not to be statistically different ($p>0.9999$).

FIG. 26A shows a gating strategy for analysis of bead-free exosomes. The Megamix+ SSC beads were run on the BD LSRFortessa SORP with low noise VPX electronics. As indicated in Megamix+ SSC protocol the bead system was first analyzed using threshold on FITC, eliminating non-fluorescent background noise.

FIG. 26B shows a gating strategy for analysis of bead-free exosomes. The Megamix+ SSC beads were run on the BD LSRFortessa SORP with low noise VPX electronics. The corresponding events displayed on side scatter height (SSC-H) versus forward scatter photomultiplier height (FSC PMT-H) plot with FITC threshold.

FIG. 26C shows a gating strategy for analysis of bead-free exosomes. The Megamix+ SSC beads were run on the BD LSRFortessa SORP with low noise VPX electronics. The bead system was then analyzed in a second step using SSC as threshold.

FIG. 26D shows a gating strategy for analysis of bead-free exosomes. The Megamix+ SSC beads were run on the BD LSRFortessa SORP with low noise VPX electronics. The corresponding events displayed on SSC-H versus FSC PMT-H plot with SSC threshold for evaluation of SSC resolution and background. A clear separation of the beads (0.16 μm, 0.20 μm, 0.24 μm and 0.50 μm) on SSC are observed with low background and standardized minimum threshold was setup by running ultra-clean water (0.1 μm filtered) as defined in the protocol. The final minimal threshold on scatter was then setup by running ultra-clean water (0.1 μm filtered) and progressively reducing threshold conditions until total events pass over 50% of the maximum speed of analysis authorized for our instrument. We then went back to a slightly higher value of SSC threshold to get back below 50% of the maximum events, thus validating and setting up the instrument for small particle analysis. All events analyzed were in a gate in the region less than 0.20 μm (box).

FIG. 27A shows CWR22Rv1 exosomes can be detected via CD63 stain. Direct flow cytometry of APC anti-CD63 antibody alone (control)

FIG. 27B shows CWR22Rv1 exosomes can be detected via CD63 stain. Direct flow cytometry of CD63 antibody and Rh-HDL NP (control)

FIG. 27C shows CWR22Rv1 exosomes can be detected via CD63 stain. Direct flow cytometry of CD63+/GFP+ exosomes (box), and FIG. 27D shows CWR22Rv1 exosomes can be detected via CD63 stain. Direct flow cytometry of CD63+/Rh+ exosomes (box).

FIG. 28 shows Rh-HDL NP uptake by A375 cells. Histogram of rhodamine fluorescence from untreated cells (left) and cells incubated with 20 nM Rh-HDL NP (right).

FIG. 29A shows GFP-SR-B1 incorporation and Rh-HDL NP labeling of exosomes. Specifically, FIG. 29A shows a western blot expression of SR-B1 and CD81 in wild-type and GFP-SR-B1 A375 melanoma cells and derived exosomes.

FIG. 29B shows GFP-SR-B1 incorporation and Rh-HDL NP labeling of exosomes. Specifically, FIG. 29B shows wild-type A375 exosomes isolated by ultracentrifugation.

FIG. 29C shows GFP-SR-B1 incorporation and Rh-HDL NP labeling of exosomes. Specifically, FIG. 29C shows GFP-SR-B1 A375 exosomes isolated by ultracentrifugation showing GFP expression (green box).

FIG. 29D shows GFP-SR-B1 incorporation and Rh-HDL NP labeling of exosomes. Specifically, FIG. 29D shows GFP+ particles in exosomes from GFP-SR-B1 A375 cells (lower box) stained for CD81 (co-labeling in upper box).

FIG. 29E shows GFP-SR-B1 incorporation and Rh-HDL NP labeling of exosomes. Specifically, FIG. 29E shows GFP+ particles in exosome prep from GFP-SR-B1 A375 cells treated with Rh-HDL NP are Rh+ (upper box).

FIG. 29F shows GFP-SR-B1 incorporation and Rh-HDL NP labeling of exosomes. Specifically, FIG. 29F shows GFP+ particles in exosomes from GFP-SR-B1 A375 cells (lower box) stained for CD63 (co-labeling in upper box).

FIG. 29G shows GFP-SR-B1 incorporation and Rh-HDL NP labeling of exosomes. Specifically, FIG. 29G shows Rh+ particles in exosomes from GFP-SR-B1 A375 cells stained for CD63 (co-labeling in upper box).

Figure 30D:
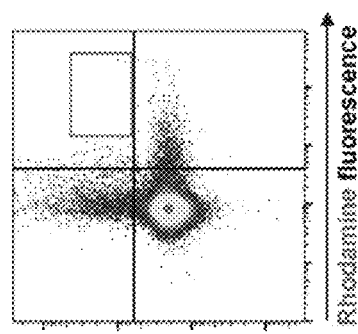
Figure 30C:
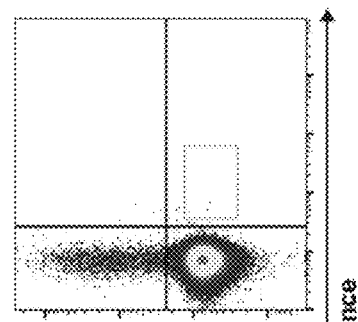
Figure 30B:
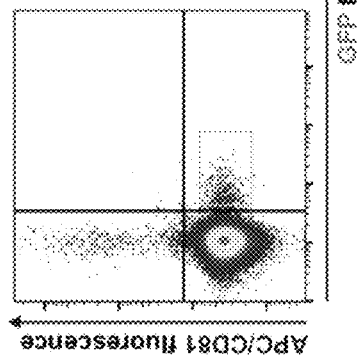
Figure 30A:
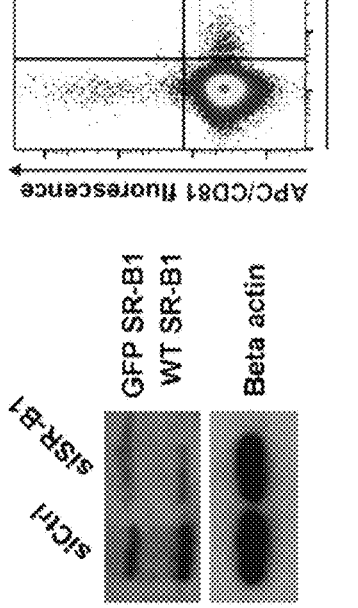

FIG. 30A shows knockdown of SR-B1 by siRNA. Specifically, FIG. 30A shows a western blot of siCtrl (left) and siSR-B1 (right) treated GFP-SR-B1 A375 cells.

FIG. 30B shows knockdown of SR-B1 by siRNA. Specifically, FIG. 30B shows Conditioned media from siCtrl treated GFP-SR-B1 A375 cells.

FIG. 30C shows knockdown of SR-B1 by siRNA. Specifically, FIG. 30C shows A375 cells treated with siSR-B1.

FIG. 30D shows knockdown of SR-B1 by siRNA. Specifically, FIG. 30D shows culture media treated with APC anti-CD81 antibody and Rh-HDL NP.

FIG. 31A shows detection of A375 exosomes labeled with Rh-HDL NP spiked into human blood at T=0. Specifically, FIG. 31A shows serum with APC anti-CD81 and no exosomes.

FIG. 31B shows detection of A375 exosomes labeled with Rh-HDL NP spiked into human blood at T=0. Specifically, FIG. 31B shows serum with APC anti-CD81 and 0.1 ng/µL added exosomes.

FIG. 31C shows detection of A375 exosomes labeled with Rh-HDL NP spiked into human blood at T=0. Specifically, FIG. 31C shows serum with APC anti-CD81 and 1.0 ng/µL added exosomes.

FIG. 31D shows detection of A375 exosomes labeled with Rh-HDL NP spiked into human blood at T=0. Specifically, FIG. 31D shows serum with APC anti-CD81 and 4.0 ng/µL added exosomes.

FIG. 31E shows quantification of gated events normalized to all events plotted against exosome concentration ($r2=0.8144$)

FIG. 32A shows DiO labels CD81 and CD63 exosomes. Specifically, FIG. 32A shows DiO stained exosomes labeled with anti-CD81.

FIG. 32B shows DiO labels CD81 and CD63 exosomes. Specifically, FIG. 32B shows DiO stained exosomes labeled with anti-CD63 antibody.

DETAILED DESCRIPTION

Intercellular communication is cell-to-cell transfer of chemicals and signals that lead to some sort of response by the receiving cell. Vesicles are important to the process as intercellular communication and provide a means to transport those chemicals and signals between cells, often in a targeted manor. Exosomes are one example of vesicles that transport molecular cargo to and from cells as a means of intercellular communication [Valadi et al. 2007; Martins et al. 2013]. Exosomes are nano-sized, and these vesicles contribute to multiple diseases, including cancers [Valadi et al. 2007; Rajendran et al. 2006; Ramakrishnaiah et al. 2013; Jung et al. 2009; Peinado et al. 2012]. In fact, cancer cells enhance their production of exosomes as a means of facilitating disease progression [Yu et al. 2006; Filipazzi et al. 2012]. For example, exosomes produced by melanoma cells have been shown to target endothelial cells to enhance angiogenesis [Ekstrom et al. 2014], as well as macrophages and dendritic cells causing immune suppression [Marton et al. 2012]. In addition, considerable data are accumulating showing that enhanced exosome production by cancer cells facilitates metastasis by conditioning the pre-metastatic niche [Peinado et al. 2011] through the mobilization of bone marrow cells and the delivery of pro-tumorigenic cargo to metastatic sites [Peinado et al. 2012].

Despite the importance of intercellular communication, there are no specific targets for inhibiting exosome uptake. At best, cellular exosome uptake mechanisms are not well defined [Feng et al. 2010]. While non-specific depletion of lipid raft cholesterol reduces cellular exosome uptake [Svensson et al. 2013], no targeted mechanism of inhibiting cellular exosome uptake by modulating cholesterol homeostasis has been reported.

The present disclosure teaches nanostructures and methods for modulating intercellular communication. In certain embodiments, modulation of intercellular communication is the inhibition of intercellular communication and an effective amount of the nanostructure inhibits the interaction between a cell and a vesicle. In certain cases, the interaction may be the uptake of a vesicle by the cell. In other cases, the interaction may be the release of a vesicle by the cell. Further embodiments and illustrations are provided below.

The present disclosure also teaches nanostructures and methods for loading a vesicle with the nanostructure. One aspect of the invention is a synthetic nanostrucuture vesicle complex comprising a vesicle, the vesicle having a surface-bound receptor, and a synthetic nanostructure, wherein the synthetic nanostructure is bound to the surface-bound receptor. In some embodiments, the synthetic nanostructure comprises a nanostructure core, a shell, the shell comprising a lipid layer surrounding and attached to the nanostructure core, and a protein associated with the shell. In certain embodiments, the synthetic nanostructure further comprises a diagnostic agent. In particular embodiments, the diagnostic agent is a tracer lipid. In particular embodiments, the tracer lipid comprises a chromophore, a biotin subunit, or both a chromophore and a biotin subunit. In some embodiments, the synthetic nanostructure further comprises a therapeutic agent. In certain embodiments, the therapeutic agent is a nucleic acid, antiviral agent, antineurological agent, or anti-rheumatologic agent. In some embodiments, the vesicle is an exosome. In some embodiments, the surface-bound receptor is SR-B1. The loaded vesicle can be used in a number of different applications, including but not limited to therapeutic or diagnostic applications. Because vesicles can specifically target, the loaded vesicles can be used to specifically target certain cells to deliver the nanostructure as a payload. The nanostructure payload may be used for therapeutic or diagnostic purposes. In certain cases the nanostructure may further comprises an agent, such as a therapeutic agent or diagnostic agent. Further embodiments and illustrations are provided below.

Another aspect of the invention is a method for preparing the synthetic nanostructure vesicle complex, the method comprising contacting a cell or a vesicle with a synthetic nanostructure to prepare a synthetic nanostructure vesicle complex, the complex comprising a vesicle, the vesicle having a surface-bound receptor, and the synthetic nanostructure, wherein the synthetic nanostructure is bound to the surface-bound receptor. In some embodiments, the cell is contacted with the synthetic nanostructure, the surface-bound receptor is bound on the surface of the cell, the cell synthetic nanostructure is taken up by the cell, and the cell secrets the complex. In other embodiments, the vesicle is contacted with the synthetic nanostructure and the surface-bound receptor is bound on the surface of the vesicle. In some embodiments, the cell or the vesicle is contacted with the synthetic nanostructure ex vivo or in vitro. In other embodiments, the cell or the vesicle is contacted with the synthetic nanostructure in vivo. In some embodiments, the method further comprising administering a therapeutically effective amount of the synthetic nanostructure to a patient having a vesicle-mediated disorder. In certain embodiments, the vesicle-mediate disorder is a cancer, a viral infection, a neurological disorder, or a rheumatic disease. In some embodiments, the synthetic nanostructure comprises a therapeutic agent. In some embodiments, the method further comprising isolating the complex, detecting the complex, or both isolating the complex and detecting the complex. In some embodiments, the complex is isolated by centrifugation at less than 90,000×g. In some embodiments, the synthetic nanostructure comprises a diagnostic agent.

Another aspect the invention is a method for inhibiting intercellular communication, comprising contacting a cell with an effective amount of a synthetic nanostructure. When contacting the cell with the effective amount of synthetic nanostructure inhibition of an interaction between the cell and a vesicle occurs. In certain embodiments, the synthetic nanostructure comprises a nanostructure core, a shell, the shell comprising a lipid layer surrounding and attached to the nanostructure core, and a protein associated with the shell. In certain embodiments, the interaction between the cell and the vesicle results is release of the vesicle by the cell. In other embodiments, the interaction between the cell and the vesicle results is uptake of the vesicle by the cell. The vesicle may be is an exosome. In some embodiments, the cell may cell expresses a receptor and the synthetic nanostructure binds the receptor, and, optionally the receptor is SR-B1. In certain embodiments, contacting the cell with the effective amount of synthetic nanostructure induces a change in the cell membrane, and, in certain cases, the change in the cell membrane may be clustering of lipid rafts in the cell membrane. In other embodiments, the effective amount of synthetic nanostructure is a therapeutically effective amount of synthetic nanostructure to treat a vesicle-mediated disorder. The vesicle-mediated disorder may be an exosome-mediated disorder or may be a cancer, a viral infection, a neurological disorder, or rheumatic disease.

Another aspect of the invention is a method for loading a vesicle, the method comprising contacting a cell with a synthetic nanostructure, wherein the synthetic nanostructure is capable of being taking up by the cell, and wherein the synthetic nanostructure is capable of being secreted in a vesicle comprising the synthetic nanostructure. In certain embodiments, synthetic nanostructure comprises a nanostructure core, a shell, the shell comprising a lipid layer surrounding and attached to the nanostructure core, and a protein associated with the shell. The vesicle may be an exosome. In certain cases, the synthetic nanostructure is taken up by the cell and/or the synthetic nanostructure is secreted in the vesicle comprising the synthetic nanostructure. In certain embodiments, the synthetic nanostructure further comprises an agent. The agent may be a diagnostic agent, a therapeutic agent, or both a diagnostic agent and a therapeutic agent. The diagnostic agent may be a tracer lipid. In certain embodiments, the tracer lipid may be a chromophore, a biotin subunit, or both a chromophore and a biotin subunit. The therapeutic agent may be a nucleic acid, antiviral agent, antineurological agent, antirheumatologic agent. In certain embodiments, the nucleic acid may be siRNA. In certain embodiments, the method further includes collecting the vesicle comprising the synthetic nanostructure and/or isolating the vesicle comprising the synthetic nanostructure. In certain embodiments, the cell may be in culture, the cell may be a cancer cell, the cell may have been removed from a patient, or the cell may be contacted with the synthetic nanostructure ex vivo. In certain embodiments, the method further includes contacting the vesicle comprising the nanostructure with a second cell. The second cell may be in culture or may be in a patient.

One aspect of the invention is a method for the treatment of a vesicle-mediated disorder, the method comprising administering a therapeutically effective amount of synthetic nanostructure to a patient in need thereof. In certain embodiments, the synthetic nanostructure comprises a nanostructure core, a shell, the shell comprising a lipid layer surrounding and attached to the nanostructure core, and a protein associated with the shell. In certain embodiments, the synthetic nanostructure further comprises a therapeutic agent. The therapeutic agent may be a nucleic acid, antiviral agent, antineurological agent, antirheumatologic agent. In certain embodiments, the nucleic acid may be siRNA. In certain embodiments, the administering step comprises contacting a cell with a vesicle comprising the synthetic nanostructure. In certain embodiments, the vesicle comprising the synthetic nanostructure is prepared by contacting a second cell with the synthetic nanostructure.

Another aspect of the invention is a method for cellular analysis, the method comprising contacting a cell with a vesicle comprising a synthetic nanostructure. In certain embodiments, the synthetic nanostructure comprises a nanostructure core, a shell, the shell comprising a lipid layer surrounding and attached to the nanostructure core, and a protein associated with the shell. In certain embodiments, the method further includes detecting the nanostructure. In certain embodiments, the synthetic nanostructure comprises a diagnostic agent. The diagnostic agent may be a tracer lipid. In certain embodiments, the tracer lipid may be a chromophore, a biotin subunit, or both a chromophore and a biotin subunit.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Terminology

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Modulating Intercellular Communication

A number of different types of vesicles play a role in intercellular communication. Exosomes are one example of vesicles that play a role in intercellular communication. Exosomes are 30-100 nm nanovesicles responsible for the transport of a myriad of molecular cargo including protein, lipids, mRNA and miRNA. Exosomes are linked to a number of difference pathologies including cancers, neurological diseases, rheumatic diseases, and viral infections.

Receptors on the cell surface also play a role in intercellular communication, as reception of a target may initiate the intercellular communication. Scavenger receptor type B-1 (SR-B1) is one example of receptor that has a role in intercellular communication, SR-B1 may also specific targets of biological as well as synthetic origin. SR-B1 is found in lipid raft in the cell membrane, and SR-B1 is a high-affinity receptor for cholesterol-rich high-density lipoproteins (HDL). SR-B1 may also bind synthetic nanostructures, like cholesterol-poor biomimetic HDL-like nanoparticles (HDL NPs) as described below. Although it was known that SR-B1 binding of synthetic nanostructures could result in apoptosis of certain cell types, it was not known that SR-B1 binding of an effective amount of synthetic nanostructure for viable cells would exhibit modulated intercellular communication.

Changes in the cell membrane may lead to modulation of intercellular communication. Changes in the cell membrane may be the result of receptors binding the synthetic nanostructure. As mentioned above, SR-B1 may be found in lipid rafts in the cell membrane and SR-B1 binding of synthetic nanoparticle may result in clustering of the lipid rafts. These morphological changes in the cell membrane modulate intercellular communication, as the cluster of the lipid rafts interfere with uptake of exosomes. In certain cases, the interference may result in the inhibition of vesicle uptake. In other cases, the interference may result in the inhibition of the release of a vesicle.

One aspect of the invention is the inhibition of intercellular communication by contacting a cell with an effective amount of a synthetic nanostructure, wherein contacting the cell with the effective amount of synthetic nanostructure inhibits an interaction between the cell and the vesicle.

The synthetic nanoparticle may be any synthetic nanoparticle that may modulate or inhibit intercellular communication when a cell is contacted with an effective amount of synthetic nanostructure. The synthetic nanostructure may comprise a nanostructure core, a shell, the shell comprising a lipid layer surrounding and attached to the nanostructure core, and a protein associate with the shell. Examples of synthetic nanostructures useful for the present purposes are described below. In some embodiments of the invention, the synthetic nanoparticle is a synthetic cholesterol binding nanostructure. The synthetic cholesterol binding nanostructure may be a biomimic of mature, spherical HDL, e.g., in terms of the size, shape, surface chemistry and/or function of the structures. Control of such features may be accomplished at least in part by using a synthetic template for the formation of the nanostructures. For example, high-density lipoprotein synthetic nanoparticles (HDL-NP) may be formed by using a gold nanoparticle (Au-NP) (or other suitable entity or material) as a synthetic template to which other components (e.g., lipids, proteins, etc.) can be added.

In some embodiments, the synthetic nanostructures may have a substantially similar size, shape and/or surface chemistry to that of natural HDL, but may differ in at least one characteristic from that of natural HDL. The at least one characteristic may be, for example, the presence or absence of one or more components in the nanostructure, the positioning of one or more components in or on the nanostructure, the materials used to form the nanostructure, the makeup of the shell of the nanostructure, the makeup of the core of the nanostructure, and combinations thereof. For example, in some embodiments, the synthetic nanostructures can be made substantially free of cholesterol (e.g., in the core, and/or prior to administration of the nanostructures to a subject or sample) as the Au-NP or other suitable entity occupies the real-estate at the core. This configuration differs from that of natural HDLs, which have a core formed of cholesteryl esters and triglycerides. Furthermore, the nanostructures described herein may have certain characteristics and/or functions similar to that of natural HDL (e.g., cholesterol binding constant) but may have other characteristics and/or functions that differ from that of natural HDL (e.g., ability to deliver cholesterol to cells). The differences between the nanostructures described herein and natural HDLs may contribute to the effectiveness of the nanostructures in treating the cells, diseases and conditions described herein.

The interaction between the cell and the vesicle may be any type of interaction associated with intercellular communication. In some embodiments, the interaction between the cell and the vesicles results in the release of the vesicle by the cell. In other embodiments, the interaction between the cell and the vesicle results in the uptake of the vesicles by the cell. In certain other embodiments, the interaction between the cell and the vesicles may result in a signaling event. For example, inhibition of ERK 1/2 signaling was shown to reduce exosome uptake, HDLs induce ERK 1/2 signaling by phosphorylation of ERK 1/2 and AKT. However, HDL NP treatment drastically reduces both ERK 1/2 and AKT phosphorylation.

The vesicle may be any vesicle associated with intercellular communication. In some embodiments the vesicles is an exosome, a virus, an apoptotic body, a synthetic lipid particle (e.g. liposome), a bacteria, or a fungus.

The cell may be any cell capable of intercellular communication. In some embodiments the cell is a cell that expresses a receptor and the receptor may bind the synthetic nanostructure. In certain embodiments, the receptor is a scavenger receptor, a receptor in the tetraspanin family, a receptor known to be a pattern receptor, a receptor known to exist in areas of the cell membrane known to be involved in particle uptake, e.g. caveolin and clathrin. The scavenger receptor may be SR-B1.

In some embodiments, the cell may be in vivo. In certain embodiments the cell may be in an animal, a human, or a patient. The patient may be a patient suffering from a vesicle-mediated or an exosome-mediated disorder. Examples of vesicle-mediate disorders include, but are not limited to, cancers, viral infection, neurological disorders, rheumatic diseases, immunological disorders, inflammation, antigen presentation, blood disorders, bacterial infection.

The other embodiments, the cell may be in vitro or ex vivo. In certain embodiments that cell may be in culture or in a biological sample.

Methods for Loading Vesicles with Nanostructures

Another aspect of the invention is a method for preparing vesicles comprising synthetic nanostructures. The vesicles comprising the synthetic nanostructures may be useful for targeted delivery of the synthetic nanostructures for therapeutic, diagnostic, or research purposes.

The method for vesicle loading comprises contacting a cell or a vesicle with a synthetic nanostructure. A vesicle comprising the synthetic nanostructure may also be referred to as a synthetic nanostrucuture vesicle complex or a loaded vesicle. In some embodiment, the loaded vesicle may be prepared by having the synthetic nanostructure taken up by the cell and by having the cell secret a vesicle comprising the synthetic nanostructure.

The synthetic nanostructure may be any synthetic nanostructure having the property of being able to be taken up by the cell and having the property of being able to be secreted in a vesicle comprising the synthetic nanostructure. The synthetic nanostructure may comprise a nanostructure core, a shell, the shell comprising a lipid layer surrounding and attached to the nanostructure core, and a protein associate with the shell. Examples of synthetic nanostructures useful for the present purposes are described below. In certain embodiments, the synthetic nanostructure may be a synthetic cholesterol binding nanostructure, i.e. a biomimic of mature, spherical HDL, e.g., in terms of the size, shape, surface chemistry and/or function of the structures. Control of such features may be accomplished at least in part by using a synthetic template for the formation of the nanostructures. For example, high-density lipoprotein synthetic nanoparticles (HDL-NP) may be formed by using a gold nanoparticle (Au-NP) (or other suitable entity or material) as a synthetic template to which other components (e.g., lipids, proteins, etc.) can be added.

In certain embodiments that synthetic nanostructure may further include an agent. The agent may be a diagnostic agent (which may also be known as an imaging agent), a therapeutic agent, or both a diagnostic agent and a therapeutic agent. In certain embodiments the diagnostic agent is a tracer lipid. Tracer lipids may comprise a chromophore, a biotin subunit, or both a chromophore and a biotin subunit. In certain embodiments the therapeutic agent may be a nucleic acid, antiviral agent, antineurological agent, antirheumatologic agent. The nucleic acid may be siRNA. Further embodiments of synthetic nanostructures useful for the invention are described below.

The vesicle may be any vesicle associated with intercellular communication such that the vesicle may be secreted by one cell and interact with another. The interaction between the cell and the vesicle comprising the synthetic nanostructure may be any type of interaction associated with intercellular communication. In some embodiments, the interaction between the cell and the vesicles results in the release of the vesicle by the cell. In other embodiments, the interaction between the cell and the vesicle results in the uptake of the vesicles by the cell. In certain other embodiments, the interaction between the cell and the vesicles may result in a signaling event.

The vesicle may be any vesicle associated with intercellular communication. In some embodiments the vesicles is an exosome, a virus, an apoptotic body, a synthetic lipid particle (e.g. liposome), a bacteria, or a fungus.

The cell may be any cell capable of secreting a vesicle for intercellular communication.

In some embodiments, the cell may be in vivo. In certain embodiments the cell may be in an animal, a human, or a patient. The patient may be a patient suffering from a vesicle-mediated or a exosome-mediated disorder. Examples of vesicle-mediate disorders include, but are not limited to, cancers, viral infection, neurological disorders, rheumatic diseases, immunological disorders, inflammation, antigen presentation, blood disorders, bacterial infection.

The other embodiments, the cell may be in vitro or ex vivo. In certain embodiments that cell may be in culture or in a biological sample.

Loaded Vesicles for Therapeutic, Diagnostic, and Research Applications

Another aspect of the invention is using a synthetic nanostrucuture vesicle complex or loaded vesicles for therapeutic, diagnostic, and research applications. In certain embodiments, the vesicle comprising the synthetic nanostructure is collected. In certain embodiments the vesicle comprising the synthetic nanostructure may be isolated.

The vesicle comprising the synthetic nanostructure may be contacted with a second cell. The contacting step may be accomplished by contacting the second cell with a loaded vesicle that has been collected and/or isolate. The contacting step may also be accomplished by having the cell secreting the vesicle comprising the synthetic nanostructure in intercellular communication with the second cell.

In some embodiments, the second cell may be in vivo. In certain embodiments the cell may be in an animal, a human, or a patient. The patient may be a patient suffering from a vesicle-mediated or a exosome-mediated disorder. Examples of vesicle-mediate disorders include, but are not limited to, cancers, viral infection, neurological disorders, rheumatic diseases immunological disorders, inflammation, antigen presentation, blood disorders, bacterial infection.

The other embodiments, the second cell may be in vitro or ex vivo. In certain embodiments that cell may be in culture or in a biological sample.

Therapeutic applications include methods for the treatment of a vesicle-mediated disorder comprising administering a therapeutically effective amount of synthetic nanostructure to a patient in need thereof. In some embodiments, the administering step comprises contacting a cell with a vesicle comprising the synthetic nanostructure. The synthetic nanostructure may comprise a therapeutic agent.

HDL NPs can also be functionalized with other types of cargo such as nucleic acids. This cargo would be loaded into exosomes and specifically delivered to appropriate locations using the intrinsic targeting capabilities of the exosomes. Existing tumors can be injected with the HDL NPs containing anti-cancer therapies, which would then package the particles into exosomes and deliver this cargo to appropriate targets.

Alternatively, cancer cells can be removed from the patient and treated with HDL NPs under laboratory culture. Exosomes can be harvested and returned to the patient, where they will deliver their cargo for use as therapy or for imaging.

Examples of therapeutic applications include, but are not limited to, methods of treating an exosome meditated disorder by administering to a subject having a exosome meditated disorder an effective amount of a synthetic nanostructure for inhibiting cellular uptake of exosomes in order to treat the exosome meditated disorder; methods of treating cancer by administering to a subject having a drug-resistant cancer an effective amount of a synthetic nanostructure for inhibiting cellular uptake of exosomes in order to treat the cancer is also provided; methods of treating a metastatic cancer by administering to a subject having a metastatic cancer an effective amount of a synthetic nanostructure for inhibiting cellular uptake of exosomes in order to treat the metastatic cancer; and methods of treating cancer by administering to a subject having a cancer, wherein the cancer is an ERK1/2 or AKT associated cancer, an effective amount of a synthetic nanostructure for inhibiting cellular uptake of exosomes in order to treat the cancer is provided. In some embodiments the ERK1/2 or AKT associated cancer is lung cancer, colon cancer, breast cancer, or prostate cancer. The lung cancer may be, for instance, NSCLC. In some embodiments the subject has naïve or acquired resistance to EGFR-targeted therapy.

Methods of treating intracellular viral infection are also provided. The method involves administering to a subject infected with an intracellular virus an effective amount of a synthetic nanostructure for inhibiting cellular uptake of virally infected exosomes in order to treat the infection.

Methods for treating a neurological disorder are also provided. The method involves administering to a subject having a neurological disorder an effective amount of a synthetic nanostructure for inhibiting cellular uptake of exosomes in order to treat the neurological disorder. In some embodiments the neurological disorder is selected from the group consisting or Alzheimer's, Parkinson's, or prion related disease.

Methods for treating a rheumatic disease by administering to a subject having a rheumatic disease an effective amount of a synthetic nanostructure for inhibiting cellular uptake of exosomes in order to treat the rheumatic disease.

Targeted delivery of cancer therapies remains a significant challenge and an area of much research. This technology would exploit the intrinsic ability of cancer cell exosomes to specifically target tissues and cells required for progression, and deliver anti-cancer therapies directly to those populations to interfere with tumor growth and metastasis. Loading exosomes using a cell-based assay is a significant improvement over current strategies such as electroporation, which are time-consuming and expensive.

There are currently no means by which artificial nanoparticles can transfer their components over to natural nanoparticles in a cell-based system. Current methodologies use cell-free methods, isolating the exosomes first and then staining them or their components outside of cells. This involves time-consuming ultracentrifugation steps that cause sample loss and/or expensive reagents. In contrast the methods of the invention would label the exosomes when they are created in the cell and functionalize them at time of synthesis, without any extra steps required. The methods of the invention also allow for simultaneous isolation and tracking of exosomes, particularly in complex mixtures such as blood, where there are many types of exosomes from many different cell types present. Flow cytometry, column-based and immunomagnetic-based separation methodologies can be employed to specifically isolate an exosome population of interest for study as biomarkers or other uses.

Diagnostic or research applications include method for cellular analysis comprising contacting a cell with a vesicle comprising a synthetic nanostructure. The invention in other aspects relates to methods and products associated with the loading of vesicles with a synthetic nanostructure using a cell-based technology. The vesicles contain the synthetic nanostructure and their components, which allows for tracking of the exosomes, isolation and quantification from mixed populations of exosomes, and packaging of synthetic nanostructures for specific delivery to cells and tissues targeted by the exosomes. In some embodiments, the synthetic nanostructure is detected. In other embodiments the synthetic nanostructure further comprises a diagnostic agent, and the diagnostic agent is detected.

Synthetic nanostructures can be used for research, diagnostic and/or therapeutic indications, where it is beneficial to label, track and/or isolate exosomes. For instance, cells in culture can be treated with HDL NPs containing a tracer lipid (fluorophore, biotin). Exosomes from these cells are now labeled and can be tracked when given to other cells in culture or injected into animal models or humans. HDL NPs with tracer can be injected into cancerous tissue. Exosomes produced by the cancerous tissue can be isolated from blood samples using the tracer for further molecular analysis. Whole-body imaging techniques could also be used to determine what tissues are targeted by the exosomes by looking for signal from the gold particle as well as any tracer molecules functionalized to it. The above properties can also be used to isolate exosomes originating from a single source from complex mixtures. Blood and other body fluids contain many types of exosomes from multiple sources. Flow cytometry and immune-based separation methods could be utilized to separate exosomes tagged with a tracer from these complex mixtures in vitro and in vivo, including human samples. This allows for the study of a particular population of exosomes originating from a certain group of cells.

Quantification of exosomes from cancer cells may also be useful as a biomarker to measure disease progression. Studies suggest increased exosome production is linked with increased tumor activity. The ability to measure levels of tumor-derived exosomes over time may help inform treatment strategies.

The synthetic nanostructures described above may be detected or may further include diagnostic agents that may be detected. Imaging agents and diagnostic agents may be used interchangeably. In certain embodiments, the synthetic nanostructure having a nanostructure core that comprises a material suitable for use as an imaging agent (e.g., gold, iron oxide, a quantum dot, radionuclide, etc.). In other embodiments, the synthetic nanostructure having a shell comprises an imaging agent. For instance, a nanoparticle or other suitable contrast agent may be embedded within the lipid bilayer of the shell, or associated with an inner or outer surface of the shell. The imaging agents may be used to enhance various imaging methods known to those in the art such as MRI, X-ray, PET, CT, etc.

Isolating Vesicles

Because of their architecture, the synthetic nanostructures may facilitate the isolation of vesicles from a variety of biological samples or tissue culture media. This may be accomplished by preparing a preparing a synthetic nanostrucuture vesicle complex and precipitating the complexes from a variety of biological samples or tissue culture media. For example, HDL NPs synthetic nanostructures can be used to precipitate exosomes from a variety of biological samples or tissue culture media. Because the HDL NPs are selective for SR-B1, only the SR-B1 positive exosomes will be isolated. As a result, the technology may be useful for any cell type positive for SR-B1, including, but not limited to, cancer cells or dendritic cells.

HDL NPs can also be labeled with a diagnostic agent, for example a fluorophore, allowing for detection and quantification of exosome populations via flow cytometry and FACS isolation. The fluorophore may be any suitable fluorophore, including, but not limited to, rhodamine-labeled phospholipids.

Isolated exosomes can then be further studied via proteomics, sequencing, etc. or used for in vitro or in vivo experiments, as their morphology remains intact.

The synthetic nanostructures, for example HDL NP, allow for isolation of exosomes by centrifugation without costly instrumentation. Exosomes require high-speed isolation at speeds of 100,000×g, requiring a specialized ultracentrifuge. The HDL NPs (and anything associated with them) pellet at speeds of 16,000×g, within the range of most standard laboratory centrifuges. As a result, exosomes may be isolated by centrifugation at speeds less than 90,000×g, less than 80,000×g, less than 70,000×g, less than 60,000×g, less than 50,000×g, less than 40,000×g, less than 30,000×g, less than 20,000×g, less than 19,000×g, less than 18,000×g, less than 17,000×, or less than 16,000×g.

The synthetic nanostrucutres also allow for the specific isolation of exosomes which express SR-B1 and may be of most interest for cancer biology. Current isolation methodologies either do not allow for specific isolation of certain exosome populations (ultracentrifugation, ExoQuick, spin columns) or involve multiple processing steps which may impact exosome morphology (bead-based isolation methods).

The synthetic nanostructures do not require a pre-enrichment of exosome populations to be effective, thus this method is much more rapid than other means (~2 hours versus 4 hours-2 days for other methods). Furthermore, bead-based kits typically require an initial isolation step from biofluids or tissue culture media.

Conjugation of a diagnostic agent to the synthetic nanostructures will allow for direct sorting of vesicles having a surface bound receptor. For example, one may conjugate a fluorophore to HDL NPs to allow for direct sorting of SR-B1 positive exosomes via FACS. Exosomes can be specifically quantified, analyzed, and isolated based on the diagnostic agent in combination with staining by antibodies for other targets, allowing for fine-tuned control over the retrieved population.

SR-B1 appears to be found in higher abundance in exosomes from patients with cancer versus healthy controls. Thus, use of the particle to quantify SR-B1 containing exosomes may be useful for diagnostic applications.

Fast and specific isolation of exosomes would allow for more extensive research to be performed, particularly with regard to clinical samples. Exosomes may contain a wealth of information, including biomarkers, which may provide better diagnostic opportunities or inform treatment. Obtaining this information on a patient to patient basis is labor intensive and cost prohibitive. This technology could remove those limitations and give clinicians more detailed information to more effectively treat their patient. On a more basic level, the presence or absence of SR-B1 positive exosomes may be useful to diagnose conditions or determine if treatments are effective.

Synthetic Nanostructures

Examples of synthetic nanostructures that can be used in the methods are described herein are now described. The structure (e.g., a synthetic structure or synthetic nanostructure) has a core and a shell surrounding the core. In embodiments in which the core is a nanostructure, the core includes a surface to which one or more components can be optionally attached. For instance, in some cases, core is a nanostructure surrounded by shell, which includes an inner surface and an outer surface. The shell may be formed, at least in part, of one or more components, such as a plurality of lipids, which may optionally associate with one another and/or with surface of the core. For example, components may be associated with the core by being covalently attached to the core, physisorbed, chemisorbed, or attached to the core through ionic interactions, hydrophobic and/or hydrophilic interactions, electrostatic interactions, van der Waals interactions, or combinations thereof. In one particular embodiment, the core includes a gold nanostructure and the shell is attached to the core through a gold-thiol bond.

Optionally, components can be crosslinked to one another. Crosslinking of components of a shell can, for example, allow the control of transport of species into the shell, or between an area exterior to the shell and an area interior of the shell. For example, relatively high amounts of crosslinking may allow certain small, but not large, molecules to pass into or through the shell, whereas relatively low or no crosslinking can allow larger molecules to pass into or through the shell. Additionally, the components forming the shell may be in the form of a monolayer or a multilayer, which can also facilitate or impede the transport or sequestering of molecules. In one exemplary embodiment, shell includes a lipid bilayer that is arranged to sequester cholesterol and/or control cholesterol efflux out of cells, as described herein.

It should be understood that a shell that surrounds a core need not completely surround the core, although such embodiments may be possible. For example, the shell may surround at least 50%, at least 60%, at least 70%, at least 80%, at least 90%, or at least 99% of the surface area of a core. In some cases, the shell substantially surrounds a core. In other cases, the shell completely surrounds a core. The components of the shell may be distributed evenly across a surface of the core in some cases, and unevenly in other cases. For example, the shell may include portions (e.g., holes) that do not include any material in some cases. If desired, the shell may be designed to allow penetration and/or transport of certain molecules and components into or out of the shell, but may prevent penetration and/or transport of other molecules and components into or out of the shell. The ability of certain molecules to penetrate and/or be transported into and/or across a shell may depend on, for example, the packing density of the components forming the shell and the chemical and physical properties of the components forming the shell. As described herein, the shell may include one layer of material, or multilayers of materials in some embodiments.

The structure (e.g., a synthetic structure or synthetic nanostructure) may also include one or more agents, such as a therapeutic or diagnostic agent. One or more agents may be associated with the core, the shell, or both; e.g., they may be associated with surface of the core, inner surface of the shell, outer surface of the shell, and/or embedded in the shell. For example, one or more agents may be associated with the core, the shell, or both through covalent bonds, physisorption, chemisorption, or attached through ionic interactions, hydrophobic and/or hydrophilic interactions, electrostatic interactions, van der Waals interactions, or combinations thereof.

In some cases, the synthetic nanostructure is a synthetic cholesterol binding nanostructure having a binding constant for cholesterol, $K_d$. In some embodiments, $K_d$ is less than or equal to about 100 μM, less than or equal to about 10 μM, less than or equal to about 1 μM, less than or equal to about 0.1 μM, less than or equal to about 10 nM, less than or equal to about 7 nM, less than or equal to about 5 nM, less than or equal to about 2 nM, less than or equal to about 1 nM, less than or equal to about 0.1 nM, less than or equal to about 10 pM, less than or equal to about 1 pM, less than or equal to about 0.1 pM, less than or equal to about 10 fM, or less than or equal to about 1 fM. Methods for determining the amount of cholesterol sequestered and binding constants are known in the art.

The core of the nanostructure whether being a nanostructure core or a hollow core, may have any suitable shape and/or size. For instance, the core may be substantially spherical, non-spherical, oval, rod-shaped, pyramidal, cube-like, disk-shaped, wire-like, or irregularly shaped. The core (e.g., a nanostructure core or a hollow core) may have a largest cross-sectional dimension (or, sometimes, a smallest cross-section dimension) of, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core has an aspect ratio of greater than about 1:1, greater than 3:1, or greater than 5:1. As used herein, "aspect ratio" refers to the ratio of a length to a width, where length and width measured perpendicular to one another, and the length refers to the longest linearly measured dimension.

In embodiments in which core includes a nanostructure core, the nanostructure core may be formed from any suitable material. In some embodiments, the core is formed of a synthetic material (e.g., a material that is not naturally occurring, or naturally present in the body). In one embodiment, a nanostructure core comprises or is formed of an inorganic material. The inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least 1 wt %, 5 wt %, 10 wt %, 25 wt %, 50 wt %, 75 wt %, 90 wt %, or 99 wt %. In one embodiment, the core is formed of 100 wt % inorganic material. The nanostructure core may, in some cases, be in the form of a quantum dot, a carbon nanotube, a carbon nanowire, or a carbon nanorod. In some cases, the nanostructure core comprises, or is formed of, a material that is not of biological origin. In some embodiments, a nanostructure includes or may be formed of one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen.

Furthermore, a shell of a structure can have any suitable thickness. For example, the thickness of a shell may be at least 10 Angstroms, at least 0.1 nm, at least 1 nm, at least 2 nm, at least 5 nm, at least 7 nm, at least 10 nm, at least 15 nm, at least 20 nm, at least 30 nm, at least 50 nm, at least 100 nm, or at least 200 nm (e.g., from the inner surface to the outer surface of the shell). In some cases, the thickness of a shell is less than 200 nm, less than 100 nm, less than 50 nm, less than 30 nm, less than 20 nm, less than 15 nm, less than 10 nm, less than 7 nm, less than 5 nm, less than 3 nm, less than 2 nm, or less than 1 nm (e.g., from the inner surface to the outer surface of the shell). Such thicknesses may be determined prior to or after sequestration of molecules as described herein.

Those of ordinary skill in the art are familiar with techniques to determine sizes of structures and particles. Examples of suitable techniques include dynamic light scattering (DLS) (e.g., using a Malvern Zetasizer instrument), transmission electron microscopy, scanning electron microscopy, electroresistance counting and laser diffraction. Other suitable techniques are known to those or ordinary skill in the art. Although many methods for determining sizes of nanostructures are known, the sizes described herein (e.g., largest or smallest cross-sectional dimensions, thicknesses) refer to ones measured by dynamic light scattering.

The shell of a structure described herein may comprise any suitable material, such as a hydrophobic material, a hydrophilic material, and/or an amphiphilic material. Although the shell may include one or more inorganic materials such as those listed above for the nanostructure core, in many embodiments the shell includes an organic material such as a lipid or certain polymers. The components of the shell may be chosen, in some embodiments, to facilitate the sequestering of cholesterol or other molecules. For instance, cholesterol (or other sequestered molecules) may bind or otherwise associate with a surface of the shell, or the shell may include components that allow the cholesterol to be internalized by the structure. Cholesterol (or other sequestered molecules) may also be embedded in a shell, within a layer or between two layers forming the shell.

The components of a shell may be charged, e.g., to impart a charge on the surface of the structure, or uncharged. In some embodiments, the surface of the shell may have a zeta potential of greater than or equal to about −75 mV, greater than or equal to about −60 mV, greater than or equal to about −50 mV, greater than or equal to about −40 mV, greater than or equal to about −30 mV, greater than or equal to about −20 mV, greater than or equal to about −10 mV, greater than or equal to about 0 mV, greater than or equal to about 10 mV, greater than or equal to about 20 mV, greater than or equal to about 30 mV, greater than or equal to about 40 mV, greater than or equal to about 50 mV, greater than or equal to about 60 mV, or greater than or equal to about 75 mV. The surface of the shell may have a zeta potential of less than or equal to about 75 mV, less than or equal to about 60 mV, less than or equal to about 50 mV, less than or equal to about 40 mV, less than or equal to about 30 mV, less than or equal to about 20 mV, less than or equal to about 10 mV, less than or equal to about 0 mV, less than or equal to about −10 mV, less than or equal to about −20 mV, less than or equal to about −30 mV, less than or equal to about −40 mV, less than or equal to about −50 mV, less than or equal to about −60 mV, or less than or equal to about −75 mV. Other ranges are also possible. Combinations of the above-referenced ranges are also possible (e.g., greater than or equal to about −60 mV and less than or equal to about −20 mV). As described herein, the surface charge of the shell may be tailored by varying the surface chemistry and components of the shell.

In one set of embodiments, a structure described herein or a portion thereof, such as a shell of a structure, includes one or more natural or synthetic lipids or lipid analogs (i.e., lipophilic molecules). One or more lipids and/or lipid analogues may form a single layer or a multi-layer (e.g., a bilayer) of a structure. In some instances where multi-layers are formed, the natural or synthetic lipids or lipid analogs interdigitate (e.g., between different layers). Non-limiting examples of natural or synthetic lipids or lipid analogs include fatty acyls, glycerolipids, glycerophospholipids, sphingolipids, saccharolipids and polyketides (derived from condensation of ketoacyl subunits), and sterol lipids and prenol lipids (derived from condensation of isoprene subunits).

In one particular set of embodiments, a structure described herein includes one or more phospholipids. The one or more phospholipids may include, for example, phosphatidylcholine, phosphatidylglycerol, lecithin, β, γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphothioethanol, and combinations thereof. In some cases, a shell (e.g., a bilayer) of a structure includes 50-200 natural or synthetic lipids or lipid analogs (e.g., phospholipids). For example, the shell may include less than about 500, less than about 400, less than about 300, less than about 200, or less than about 100 natural or synthetic lipids or lipid analogs (e.g., phospholipids), e.g., depending on the size of the structure.

Non-phosphorus containing lipids may also be used such as stearylamine, docecylamine, acetyl palmitate, and fatty acid amides. In other embodiments, other lipids such as fats, oils, waxes, cholesterol, sterols, fat-soluble vitamins (e.g., vitamins A, D, E and K), glycerides (e.g., monoglycerides, diglycerides, triglycerides) can be used to form portions of a structure described herein.

A portion of a structure described herein such as a shell or a surface of a nanostructure may optionally include one or more alkyl groups, e.g., an alkane-, alkene-, or alkyne-containing species that optionally imparts hydrophobicity to the structure. An "alkyl" group refers to a saturated aliphatic group, including a straight-chain alkyl group, branched-chain alkyl group, cycloalkyl (alicyclic) group, alkyl substituted cycloalkyl group, and cycloalkyl substituted alkyl group. The alkyl group may have various carbon numbers, e.g., between $C_2$ and $C_{40}$, and in some embodiments may be greater than $C_5$, $C_{10}$, $C_{15}$, $C_{20}$, $C_{25}$, $C_{30}$, or $C_{35}$. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The alkyl group may include any suitable end group, e.g., a thiol group, an amino group (e.g., an unsubstituted or substituted amine), an amide group, an imine group, a carboxyl group, or a sulfate group, which may, for example, allow attachment of a ligand to a nanostructure core directly or via a linker. For example, where inert metals are used to form a nanostructure core, the alkyl species may include a thiol group to form a metal-thiol bond. In some instances, the alkyl species includes at least a second end group. For example, the species may be bound to a hydrophilic moiety such as polyethylene glycol. In other embodiments, the second end group may be a reactive group that can covalently attach to another functional group. In some instances, the second end group can participate in a ligand/receptor interaction (e.g., biotin/streptavidin).

In some embodiments, the shell includes a polymer. For example, an amphiphilic polymer may be used. The polymer may be a diblock copolymer, a triblock copolymer, etc., e.g., where one block is a hydrophobic polymer and another block is a hydrophilic polymer. For example, the polymer may be a copolymer of an α-hydroxy acid (e.g., lactic acid) and polyethylene glycol. In some cases, a shell includes a hydrophobic polymer, such as polymers that may include certain acrylics, amides and imides, carbonates, dienes, esters, ethers, fluorocarbons, olefins, sytrenes, vinyl acetals, vinyl and vinylidene chlorides, vinyl esters, vinyl ethers and ketones, and vinylpyridine and vinylpyrrolidones polymers. In other cases, a shell includes a hydrophilic polymer, such as polymers including certain acrylics, amines, ethers, styrenes, vinyl acids, and vinyl alcohols. The polymer may be charged or uncharged. As noted herein, the particular components of the shell can be chosen so as to impart certain functionality to the structures.

Where a shell includes an amphiphilic material, the material can be arranged in any suitable manner with respect to the nanostructure core and/or with each other. For instance, the amphiphilic material may include a hydrophilic group that points towards the core and a hydrophobic group that extends away from the core, or, the amphiphilic material may include a hydrophobic group that points towards the core and a hydrophilic group that extends away from the core. Bilayers of each configuration can also be formed.

The structures described herein may also include one or more proteins, polypeptides and/or peptides (e.g., synthetic peptides, amphiphilic peptides). In one set of embodiments, the structures include proteins, polypeptides and/or peptides that can increase the rate of cholesterol transfer or the cholesterol-carrying capacity of the structures. The one or more proteins or peptides may be associated with the core (e.g., a surface of the core or embedded in the core), the shell (e.g., an inner and/or outer surface of the shell, and/or embedded in the shell), or both. Associations may include covalent or non-covalent interactions (e.g., hydrophobic and/or hydrophilic interactions, electrostatic interactions, van der Waals interactions).

An example of a suitable protein that may associate with a structure described herein is an apolipoprotein, such as apolipoprotein A (e.g., apo A-I, apo A-II, apo A-IV, and apo A-V), apolipoprotein B (e.g., apo B48 and apo B100), apolipoprotein C (e.g., apo C-I, apo C-II, apo C-III, and apo C-IV), and apolipoproteins D, E, and H. Specifically, apo $A_1$, apo $A_2$, and apo E promote transfer of cholesterol and cholesteryl esters to the liver for metabolism and may be useful to include in structures described herein. Additionally or alternatively, a structure described herein may include one or more peptide analogues of an apolipoprotein, such as one described above. A structure may include any suitable number of, e.g., at least 1, 2, 3, 4, 5, 6, or 10, apolipoproteins or analogues thereof. In certain embodiments, a structure includes 1-6 apolipoproteins, similar to a naturally occurring HDL particle. Of course, other proteins (e.g., non-apolipoproteins) can also be included in structures described herein.

Optionally, one or more enzymes may also be associated with a structure described herein. For example, lecithin-cholesterol acyltransferase is an enzyme that converts free cholesterol into cholesteryl ester (a more hydrophobic form of cholesterol). In naturally-occurring lipoproteins (e.g., HDL and LDL), cholesteryl ester is sequestered into the core of the lipoprotein, and causes the lipoprotein to change from a disk shape to a spherical shape. Thus, structures described herein may include lecithin-cholesterol acyltransferase to mimic HDL and LDL structures. Other enzymes such as cholesteryl ester transfer protein (CETP) which transfers esterified cholesterol from HDL to LDL species may also be included.

It should be understood that the components described herein, such as the lipids, phospholipids, alkyl groups, polymers, proteins, polypeptides, peptides, enzymes, bioactive agents, nucleic acids, and species for targeting described above (which may be optional), may be associated with a structure in any suitable manner and with any suitable portion of the structure, e.g., the core, the shell, or both. For example, one or more such components may be associated with a surface of a core, an interior of a core, an inner surface of a shell, an outer surface of a shell, and/or embedded in a shell. Furthermore, such components can be used, in some embodiments, to facilitate the sequestration, exchange and/or transport of materials (e.g., proteins, peptides, polypeptides, nucleic acids, nutrients) from one or more components of a subject (e.g., cells, tissues, organs, particles, fluids (e.g., blood), and portions thereof) to a structure described herein, and/or from the structure to the one or more components of the subject. In some cases, the components have chemical and/or physical properties that allow favorable interaction (e.g., binding, adsorption, transport) with the one or more materials from the subject.

Additionally, the components described herein, such as the lipids, phospholipids, alkyl groups, polymers, proteins, polypeptides, peptides, enzymes, bioactive agents, nucleic acids, and species for targeting described above, may be associated with a structure described herein prior to administration to a subject or biological sample and/or after administration to a subject or biological sample. For example, in some cases a structure described herein includes a core and a shell that is administered in vivo or in vitro, and the structure has a greater therapeutic effect after sequestering one or more components (e.g., an apolipoprotein) from a subject or biological sample. That is, the structure may use natural components from the subject or biological sample to increase efficacy of the structure after it has been administered.

A variety of methods can be used to fabricate the nanostructures described herein. Examples of methods are provided in International Patent Publication No. WO/2009/131704, filed Apr. 24, 2009 and entitled, "Nanostructures Suitable for Sequestering Cholesterol and Other Molecules", which is incorporated herein by reference in its entirety for all purposes.

As described herein, the synthetic nanostructures may be used in "pharmaceutical compositions" or "pharmaceutically acceptable" compositions, which comprise a therapeutically effective amount of one or more of the structures described herein, formulated together with one or more pharmaceutically acceptable carriers, additives, and/or diluents. The pharmaceutical compositions described herein may be useful for treating cancer or other conditions. It should be understood that any suitable structures described herein can be used in such pharmaceutical compositions, including those described in connection with the figures. In some cases, the structures in a pharmaceutical composition have a nanostructure core comprising an inorganic material and a shell substantially surrounding and attached to the nanostructure core.

The pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The structures described herein may be orally administered, parenterally administered, subcutaneously administered, and/or intravenously administered. In certain embodiments, a structure or pharmaceutical preparation is administered orally. In other embodiments, the structure or pharmaceutical preparation is administered intravenously. Alternative routes of administration include sublingual, intramuscular, and transdermal administrations.

Pharmaceutical compositions described herein include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, and the particular mode of administration. The amount of active ingredient that can be combined with a carrier material to produce a single dosage form will generally be that amount of the compound that produces a therapeutic effect. Generally, this amount will range from about 1% to about 99% of active ingredient, from about 5% to about 70%, or from about 10% to about 30%.

The inventive compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a structure described herein as an active ingredient. An inventive structure may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered structure is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the structures described herein include pharmaceutically acceptable emulsions, microemulsions, solutions, dispersions, suspensions, syrups and elixirs. In addition to the inventive structures, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein (e.g., for rectal or vaginal administration) may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the body and release the structures.

Dosage forms for the topical or transdermal administration of a structure described herein include powders, sprays, ointments, pastes, foams, creams, lotions, gels, solutions, patches and inhalants. The active compound may be mixed under sterile conditions with a pharmaceutically-acceptable carrier, and with any preservatives, buffers, or propellants, which may be required.

The ointments, pastes, creams and gels may contain, in addition to the inventive structures, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the structures described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a structure described herein to the body. Dissolving or dispersing the structure in the proper medium can make such dosage forms. Absorption enhancers can also be used to increase the flux of the structure across the skin. Either providing a rate controlling membrane or dispersing the structure in a polymer matrix or gel can control the rate of such flux.

Ophthalmic formulations, eye ointments, powders, solutions and the like, are also contemplated as being within the scope of this invention.

Pharmaceutical compositions described herein suitable for parenteral administration comprise one or more inventive structures in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the inventive structures may be facilitated by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Delivery systems suitable for use with structures and compositions described herein include time-release, delayed release, sustained release, or controlled release delivery systems, as described herein. Such systems may avoid repeated administrations of the structures in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The compositions may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiments. The structures and compositions described herein can also be combined (e.g., contained) with delivery devices such as syringes, pads, patches, tubes, films, MEMS-based devices, and implantable devices.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

Injectable depot forms can be made by forming microencapsule matrices of the structures described herein in biodegradable polymers such as polylactide-polyglycolide. Depending on the ratio of structure to polymer, and the nature of the particular polymer employed, the rate of release of the structure can be controlled. Examples of other biodegradable polymers include poly(orthoesters) and poly(anhydrides).

When the structures described herein are administered as pharmaceuticals, to humans and animals, they can be given per se or as a pharmaceutical composition containing, for example, about 0.1% to about 99.5%, about 0.5% to about 90%, or the like, of structures in combination with a pharmaceutically acceptable carrier.

The administration may be localized (e.g., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the structures described herein, which may be used in a suitable hydrated form, and/or the inventive pharmaceutical compositions, are formulated into pharmaceutically-acceptable dosage forms by conventional methods known to those of skill in the art.

The compositions described herein may be given in dosages, e.g., at the maximum amount while avoiding or minimizing any potentially detrimental side effects. The compositions can be administered in effective amounts, alone or in a combinations with other compounds. For example, when treating cancer, a composition may include the structures described herein and a cocktail of other compounds that can be used to treat cancer. When treating conditions associated with abnormal lipid levels, a composition may include the structures described herein and other compounds that can be used to reduce lipid levels (e.g., cholesterol lowering agents).

The phrase "therapeutically effective amount" as used herein means that amount of a material or composition comprising an inventive structure that is effective for producing some desired therapeutic effect in a subject at a reasonable benefit/risk ratio applicable to any medical treatment. Accordingly, a therapeutically effective amount may, for example, prevent, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more structures described herein may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more structure described herein in an amount effective to treat one or more diseases or bodily conditions described herein.

An effective amount may depend on the particular condition to be treated. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular inventive structure employed, the route of administration, the time of administration, the rate of excretion or metabolism of the particular structure being employed, the duration of the treatment, other drugs, compounds and/or materials used in combination with the particular structure employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the structures described herein employed in the pharmaceutical composition at levels lower than that required to achieve the desired therapeutic effect and then gradually increasing the dosage until the desired effect is achieved.

In some embodiments, a structure or pharmaceutical composition described herein is provided to a subject chronically. Chronic treatments include any form of repeated administration for an extended period of time, such as repeated administrations for one or more months, between a month and a year, one or more years, or longer. In many embodiments, a chronic treatment involves administering a structure or pharmaceutical composition repeatedly over the life of the subject. For example, chronic treatments may involve regular administrations, for example one or more times a day, one or more times a week, or one or more times a month. In general, a suitable dose such as a daily dose of a structure described herein will be that amount of the structure that is the lowest dose effective to produce a therapeutic effect. Such an effective dose will generally depend upon the factors described above. Generally doses of the structures described herein for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms. For example, instructions and methods may include dosing regimens wherein specific doses of compositions, especially those including structures described herein having a particular size range, are administered at specific time intervals and specific doses to achieve reduction of cholesterol (or other lipids) and/or treatment of disease while reducing or avoiding adverse effects or unwanted effects.

While it is possible for a structure described herein to be administered alone, it may be administered as a pharmaceutical composition as described above. The present invention also provides any of the above-mentioned compositions useful for diagnosing, preventing, treating, or managing a disease or bodily condition packaged in kits, optionally including instructions for use of the composition. That is, the kit can include a description of use of the composition for participation in any disease or bodily condition, including those associated with abnormal lipid levels. The kits can further include a description of use of the compositions as discussed herein. The kit also can include instructions for use of a combination of two or more compositions described herein. Instructions also may be provided for administering the composition by any suitable technique, such as orally, intravenously, or via another known route of drug delivery.

The kits described herein may also contain one or more containers, which can contain components such as the structures, signaling entities, and/or biomolecules as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the particular inventive structure and the mode of use or administration. Suitable solvents for compositions are well known and are available in the literature.

The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human), for example, a mammal that may be susceptible to a disease or bodily condition such as a disease or bodily condition associated with abnormal lipid levels. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition. In some embodiments, a subject may be diagnosed with, or otherwise known to have, a disease or bodily condition associated with abnormal lipid levels, as described herein. In certain embodiments, a subject may be selected for treatment on the basis of a known disease or bodily condition in the subject. In some embodiments, a subject may be selected for treatment on the basis of a suspected disease or bodily condition in the subject. In some embodiments, the composition may be administered to prevent the development of a disease or bodily condition. However, in some embodiments, the presence of an existing disease or bodily condition may be suspected, but not yet identified, and a composition of the invention may be administered to diagnose or prevent further development of the disease or bodily condition.

A "biological sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

EXAMPLES

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

Example 1

The present example demonstrates the inhibition of intercellular communication by contacting cells with synthetic nanostructure. As further described below, HDL NPs target SR-B1, manipulate cellular cholesterol homeostasis, and modulate the uptake of exosomes by disrupting lipid rafts.

HDL NP Synthesis:

Biomimetic high-density lipoprotein-like nanoparticles (HDL NPs) were synthesized and characterized as previously described [Yang et al. 2013; Luthi et al. 2012; Thaxton et al. 2009]. Briefly, citrate stabilized 5 nm diameter gold nanoparticles (AuNP, Ted Pella) were used as a template for surface chemical modification. Purified human apolipoprotein AI (apoA-I) was incubated with a solution of AuNPs (80 nM) at 5-fold molar excess (400 nM, final) for 1 hour at room temperature (RT) with gentle stirring. Next, the phospholipids, 1-2-dipalmitoyl-sn-glycero-3-phosphocholine and 1,2-dipalmitoyl-sn-glycero-3-phosphoethanolamine-N-[3-(2-pyridyldithio)propionate] were added at 250 molar excess relative to [AuNP] in a mixture of ethanol and water (1:4), and allowed to incubate at RT for 4 hours with gentle stirring. The HDL NPs were then purified and concentrated using tangential flow filtration. The HDL NP concentration and final conjugate size were determined using UV-Vis spectrophotometry ($\varepsilon_{AuNP}$=9.696×10$^6$ M$^{-1}$ cm$^{-1}$ at $\lambda_{max}$=520 nm) and dynamic light scattering (DLS, Malvern Zetasizer), respectively.

Cell Culture:

A375 melanoma cells (ATCC) and RAW 264.7 macrophages (ATCC) were cultured in Dulbecco's Modified Eagle Medium (DMEM) containing 10% fetal bovine serum and 1% penicillin/streptomycin. Human dermal microvascular endothelial cells (HMVECs) and endothelial cell growth medium were from Promocell. Cells were incubated at 37° C. and in a humidified 5% CO$_2$ environment. The GFP-SR-B1 plasmid [Neculai et al. 2013] was stably transfected in the A375 cells using Lipofectamine 2000 (Life Technologies) and transfectants were selected using Geneticin (Life Technologies) followed by fluorescent associated cell sorting (FACS).

Exosome Isolation and Labeling:

A375 melanoma exosomes were isolated from conditioned media using differential ultracentrifugation [Thery et al. 2006]. In brief, cells were cultured in exosome deficient media for 72 hours at which point the cell culture media was collected and centrifuged at 2000×g to remove dead cells and debris. Next, larger vesicles and cell debris were removed by centrifugation at 10,000×g for 30 minutes. Exosomes were then pelleted by centrifugation at 100,000×g for 70 minutes, and subsequently washed in PBS by another 100,000×g centrifugation step for 70 minutes. Exosomes were re-suspended in PBS. Protein concentration of exosomes was analyzed by BCA Protein assay (Thermo Scientific). Exosome size and morphology was characterized using DLS and transmission electron microscopy (FEI Spirit G2 TEM). In the experiments utilizing fluorescently labeled exosomes, the lipophilic dye, DiI (Life Technologies), was added to the exosome preparation at a concentration of 2.5 µM after the first 100,000×g ultracentrifugation step. The DiI-labeled exosomes were then washed twice in PBS by pelleting the exosomes and discarding the supernatant. Notably, gold nanoparticles demonstrate distance-dependent fluorescence quenching [Nerambourg et al. 2007]. In order to test if HDL NPs quenched exosome fluorescence, we incubated HDL NPs with fluorescently labeled exosomes for 4 hours and then measured the fluorescent signal. Data demonstrate no reduction in fluorescence indicating that this is not a mechanism of reduced fluorescence in our measurements.

Cell Treatments with hHDL and HDL NP:

For cholesterol determination assays, efflux assays, and cell treatments we used equimolar amounts of hHDL and HDL NPs based upon apo A-I concentration. The molar concentration of HDL NP was determined as discussed above, and each HDL NP has approximately three copies of apo A-I [Luthi et al. 2012]. Therefore, the molar concentration of apo A-I is easily calculated for the HDL NPs. Human HDL was purchased from Calbiochem. The protein concentration of purchased hHDL was provided. From this value, the amount of apo A-I was calculated for hHDL assuming that 70% of the total protein is apo A-I [Rader et al. 2009]. Thus, for each treatment the amount of apo A-I is equivalent for hHDL and HDL NP and, because each hHDL and HDL NP has approximately three copies of apo A-I [Huang et al. 2011], the dose of particles is assumed equivalent.

Exosome Uptake Assays:

The cellular uptake of exosomes was measured by fluorescence microscopy and flow cytometry after cell treatments. A375 cells, HMVECs and RAW 264.7 macrophages were treated with fluorescent exosomes at a concentration of 1 µg/ml (exosomal protein). For fluorescence microscopy experiments, cells were plated on coverslips coated with 0.1% gelatin. Exosome uptake was measured over the course of 24 hours using a BD LSR Fortessa flow cytometer (Robert H. Lurie Comprehensive Cancer Center Flow Cytometry Core) or a Nikon A1R fluorescence microscope (Northwestern University Nikon Imaging Facility).

Cholesterol and Cholesterol Ester Quantification:

The total cholesterol and cholesteryl ester content of hHDLs and HDL NPs was measured using an Amplex Red cholesterol detection assay (Life Technologies). The free cholesterol content of each sample was measured in the absence and presence of cholesterol esterase to determine the free cholesterol and total cholesterol, respectively. Cholesteryl ester amount was determined by subtracting the free cholesterol from total cholesterol measurement. To determine the free and esterified cholesterol content of hHDL and HDL NPs before cell incubation we followed the protocol supplied by the manufacturer. The free and esterified cholesterol content of the hHDL and HDL NP acceptors was measured after incubating with cultured A375 melanoma cells in serum free media and HDL NP (50 nM, final) or hHDL (50 nM, final) for 24 hours. After the treatment interval, the culture media was collected and centrifuged to rid the media of cells and cell debris. The total cholesterol and free cholesterol was then determined from conditioned media samples using the Amplex Red assay.

Cholesterol Efflux Assay:

A375 cells were cultured in DMEM containing 1 µCi/mL [1,2,-$^3$H] cholesterol (Perkin-Elmer) overnight to label the cellular cholesterol pool. Cells were then washed in PBS and resuspended in serum free media. Human HDL or HDL NPs were added to the culture media and allowed to incubate for 6 hours. Cell culture media was then collected and subjected to liquid scintillation counting. The percentage of cholesterol efflux was determined by using the formula counts media/(counts cells+counts media)×100. Efflux of cholesterol in the absence of an acceptor was also measured and interpreted along with other results.

Computer Vision Analysis of GFP-SR-B1 Domains, Intensity, and Dynamics:

A semi-automated approach using ImageJ software was employed to identify the areas of GFP-SR-B1 in the images. After background subtraction, an unsharp mask filter with a large radius was applied to locally enhance contrast. Manual thresholding of filtered images was then used to generate a segment mask, which could be overlaid on the original, background subtracted image to facilitate measurement of domain parameters such as area and mean intensity.

To test differences in the dynamics properties of the GFP-SR-B1 domains, we identified in automated fashion the center of mass of the spots using a wavelet-based segmentation approach [Olivo-Marin et al. 2002] and tracked their displacement [Svensson et al. 2013]. The method used solves a global combinatorial optimization problem whose solution identifies the overall most likely links of particle trajectories throughout a movie. It allows the tracking of the heterogeneous domain motion both during phases of diffusive and linear motion. During the linking part of the algorithm, we allowed speeds of up to 42 microns/min, as we observed some very rapid motion. We did not use the gap closing option of the algorithm, as the fluorescent labeling was consistently bright and the GFP-SR-B1 motion did not result in occlusion. We included in our dynamics analysis tracks with a lifetime of over four frames.

Figure 3:
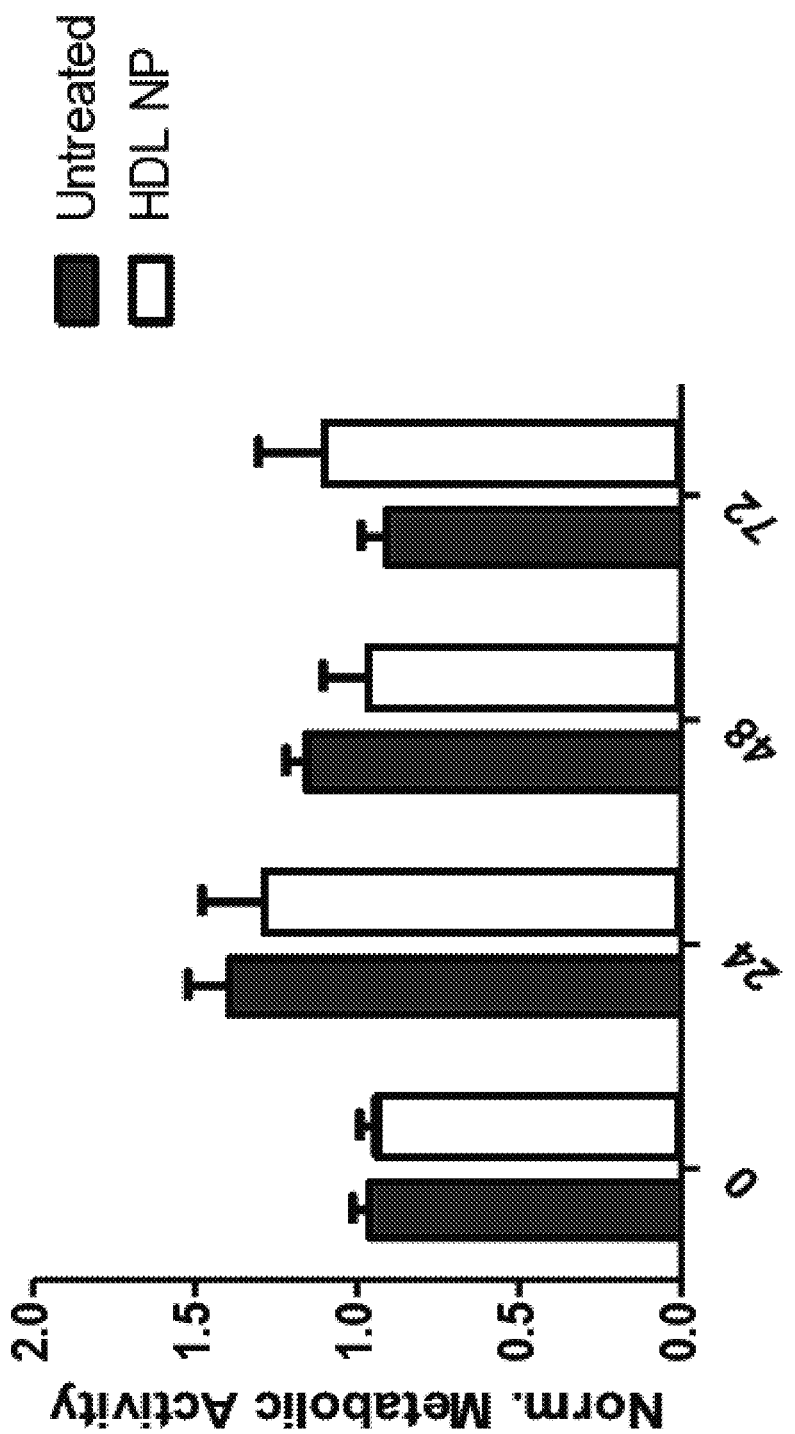
FIG. 3 shows HDL NPs have no effect on cellular viability. A375 melanoma cells were treated with 50 nM HDL NP and the cytotoxicity was measured using 3-(4,5- dimethylthiazol-2-yl)-5-(3-carboxymethoxyphenyl)-2-(4-sulfophenyl)-2H-tetrazolium (MTS) assay at T=0, 24, 48, and 72 hours after HDL NP treatment.

To calculate the linearity of the motion, we introduced a parameter rho (FIG. 3C), which is calculated as the ratio between the head-to-tail (first point to the end point) trajectory distance divided by the total distance traveled by fluorescent domains. This way, a trajectory with rho close to 1 signifies a linearly moving spot and a trajectory with rho close to 0 signifies randomly moving spots. For this analysis, we excluded all stationary areas by considering spots that moved a pixel per frame one average or more.

Western Blotting:

For Western blot, 20 µg of total protein extract or 10 µg of exosomal protein were resolved on Tris/Glycine/SDS pre-cast polyacrylamide gels (a 4-20% gradient, Bio-Rad, 30 minutes at 200 volts). Proteins were transferred onto polyvinylidene fluoride (PVDF) membranes. The membranes were blocked in 5% milk in Tris-buffered saline containing 0.1% Tween 20 (TBST). The membranes were incubated with d primary antibodies (diluted in blocking solution) overnight at 4° C., was washed 3 times in 0.1% TBST (10 minutes/wash) and incubated with the appropriate HRP-conjugated secondary antibody in blocking buffer for 1 hour at room temperature. The membranes were then washed in 0.1% TBST (3×10 min) and developed with ECL kit (GE Healthcare).

Antibodies: CD81 and GM130 (Santa Cruz Biotechnology), SR-B1 (Abcam), β-Actin (Cell Signaling Technology)

Lipid Raft Labeling:

A375 lipid rafts were labeled using cholera toxin subunit b (CTx-B) conjugates with Alexafluor 488 or Alexafluor 647 to (Life Technologies) at a final concentration 1 µg/ml, for 30 minutes at 37° C. [Svensson et al. 2013]. The cells were then washed in PBS. And visualized using fluorescence microscopy.

Fluorescence Microscopy:

Fluorescence microscopy was performed using an A1R confocal microscope with assistance from the Northwestern University Center for Advanced Microscopy. Images were analyzed using NIS Elements (Nikon) and ImageJ (NIH) software. Live cell confocal fluorescence microscopy to assess lipid raft dynamics was performed with a Nikon Eclipse T1 microscope equipped with an Andor iXon Ultra 897 camera and analyzed using Metamorph software (Molecular Devices).

Statistical Analysis:

Data was expressed using ±standard deviation of triplicate experiments. The unpaired two tailed student's t-test from GraphPad Prism software was used to analyze data. Statistical significance was considered for significant for P≤0.05. * Denotes P≤0.05,  P≤0.01, and * P≤0.001. FCS Express was used to analyze flow cytometry. Statistical analysis between the conditions (before and after HDL NP treatment) of GFP-SR-B1, integrated normalized intensity, and motion was performed using a permutation test [Svensson et al. 2013] for means, which does not assume normality of the underlying distributions.

Figure 1B:
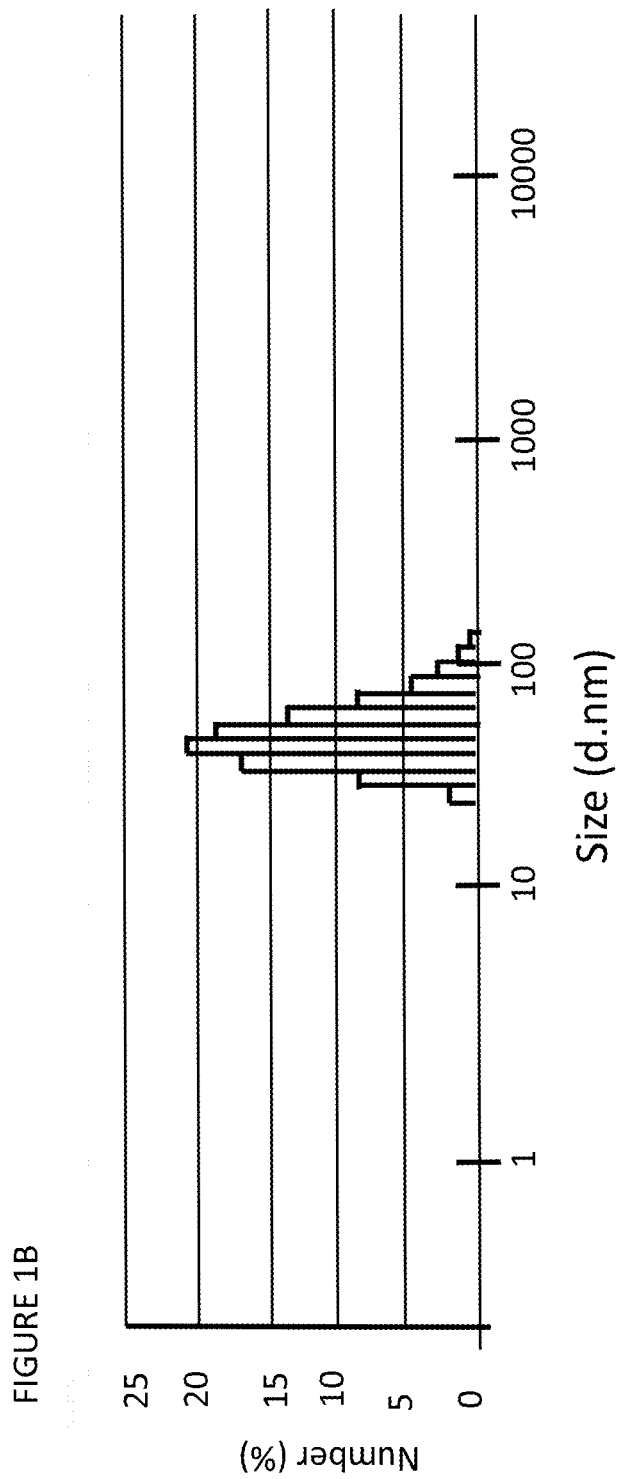
FIG. 1B shows characterization of A375 melanoma exosomes: size, morphology and molecular markers. Specifically.

Results and Discussion:

We cultured A375 melanoma cells and isolated released exosomes from conditioned media using differential ultracentrifugation [Thery et al. 2006] Transmission electron microscopy (TEM) and dynamic light scattering (DLS) measurements demonstrate the expected morphology and size (30-100 nm) for exosomes, respectively (FIGS. 1A and 1B). Exosome-specific protein cargo was identified by western blot to molecularly confirm the identity of isolated exosomes (FIG. 1C). Our data show that A375 cells express SR-B1 and exosomes from this cell line are also enriched for this receptor (FIG. 1C). Thus, our results demonstrate the ability to isolate melanoma exosomes for experiments, and that A375 melanoma cells and exosomes contain SR-B1, a receptor intimately linked with HDL binding and cholesterol transport.

Figure 2A:
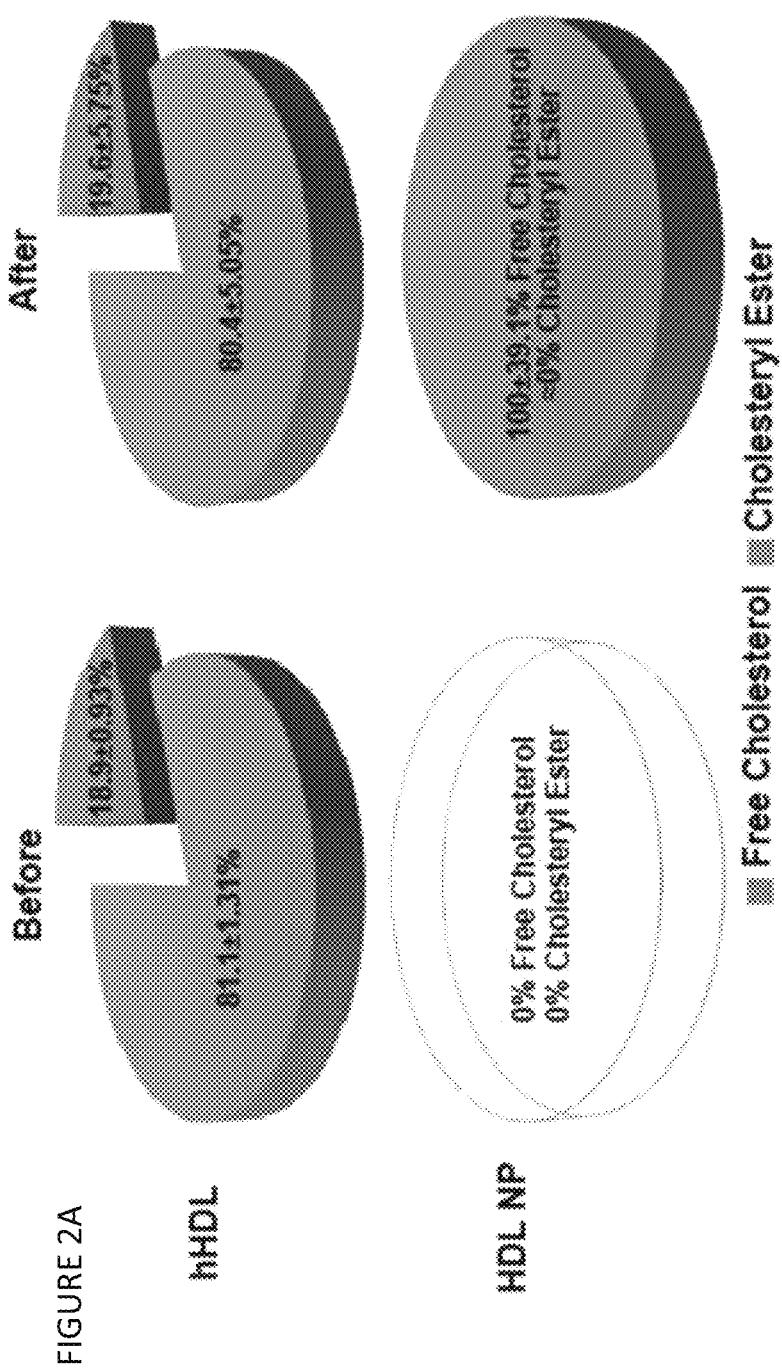
FIG. 2A shows free and esterified cholesterol content of hHDL and HDL NP, cholesterol efflux, and specific targeting of SR-B1 in lipid rafts. Specifically.
Figure 2C:
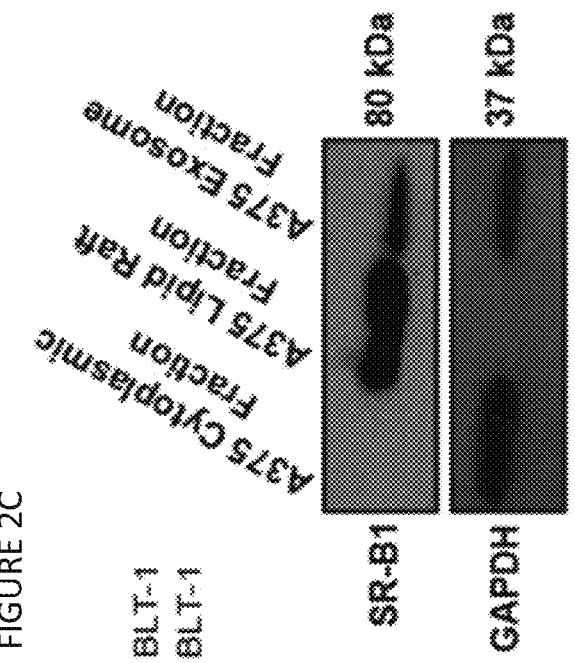
FIG. 2C shows free and esterified cholesterol content of hHDL and HDL NP, cholesterol efflux, and specific targeting of SR-B1 in lipid rafts. Specifically.
Figure 2B:
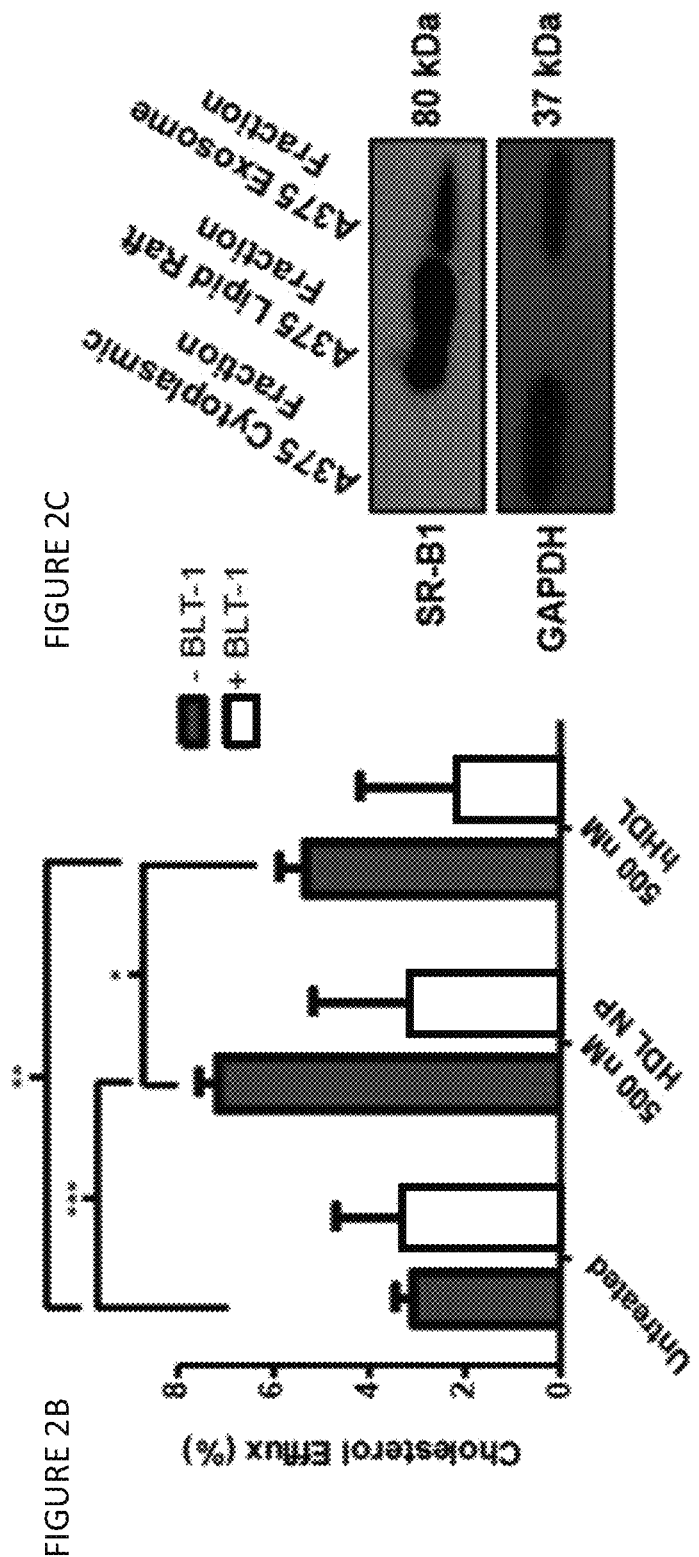
FIG. 2B shows free and esterified cholesterol content of hHDL and HDL NP, cholesterol efflux, and specific targeting of SR-B1 in lipid rafts. Specifically.

High-density lipoproteins are dynamic natural nanostructures that function to sequester, transport, and deliver cholesterol [McMahon et al. 2011]. High-density lipoprotein-like nanoparticles are synthesized as described above. Comparison of HDL NPs to certain spherical hHDL species reveals similarities with regard to size, shape, surface chemistry, and negative surface charge [Luthi et al. 2012; McMahon & Thaxton 2014; Luthi et al. 2015]. Functionally, hHDLs bind SR-B1, which mediates the bi-directional flux of free cholesterol and the influx of esterified cholesterol to cells [Luthi et al. 2012; Van Eck et al. 2005; Luthi et al. 2015]. An important distinction between hHDLs and HDL NPs is that, while HDL NPs have been shown to mediate bi-directional free cholesterol flux through SR-B1 [Yang et al. 2013; Luthi et al. 2012; Thaxton et al. 2009], the gold nanoparticle core of HDL NPs occupies the same physical space as esterified cholesterol and triglycerides in spherical hHDL. Occupying this space renders HDL NPs incapable of delivering to cells a payload of cholesteryl ester [Yang et al. 2013]. To clearly demonstrate this, we measured free and esterified cholesterol in hHDL, used in the experiments for this study, and HDL NPs. Data reveal a lack of either free or esterified cholesterol in freshly synthesized HDL NPs (FIG. 2A), as expected, while hHDLs have ~19% free and ~81% esterified cholesterol (percent of total measured cholesterol), respectively (FIG. 2A). To interrogate the differences in cellular cholesterol flux between hHDLs and HDL NPs in the A375 melanoma cell line, we labeled the cellular cholesterol pool using 3H-cholesterol, and then performed efflux assays to measure the removal of 3H-cholesterol from these cells. Data show that HDL NPs induce cholesterol efflux from melanoma cells at levels that exceed those observed for hHDL (FIG. 2B). Cholesterol efflux is at least in part mediated by specific targeting of the SR-B1 receptor by hHDLs and HDL NPs, as treatment with Blocks Lipid Transport 1 (BLT-1), an inhibitor of SR-B1-mediated cholesterol flux [Nieland et al. 2002], resulted in reduced efflux to both hHDLs and HDL NPs (FIG. 2B). After the efflux assay, hHDLs and HDL NPs have increased free cholesterol (percent of total measured cholesterol); however, there is no measurable esterified cholesterol in HDL NPs versus hHDLs (FIG. 2A). Finally, we performed cell viability assays to ascertain whether treatment by HDL NPs reduced A375 cell viability. Data demonstrate that HDL NP treatment does not result in reduced viability (FIG. 3) even at doses above those that inhibit cellular exosome uptake (vide infra) at time points up to 72 hours. Thus, cholesterol and cholesteryl ester-poor HDL NPs are not inherently toxic to A375 melanoma cells, target SR-B1, and differentially modulate cholesterol flux through this receptor.

Figures 2D, 2E, 2F:
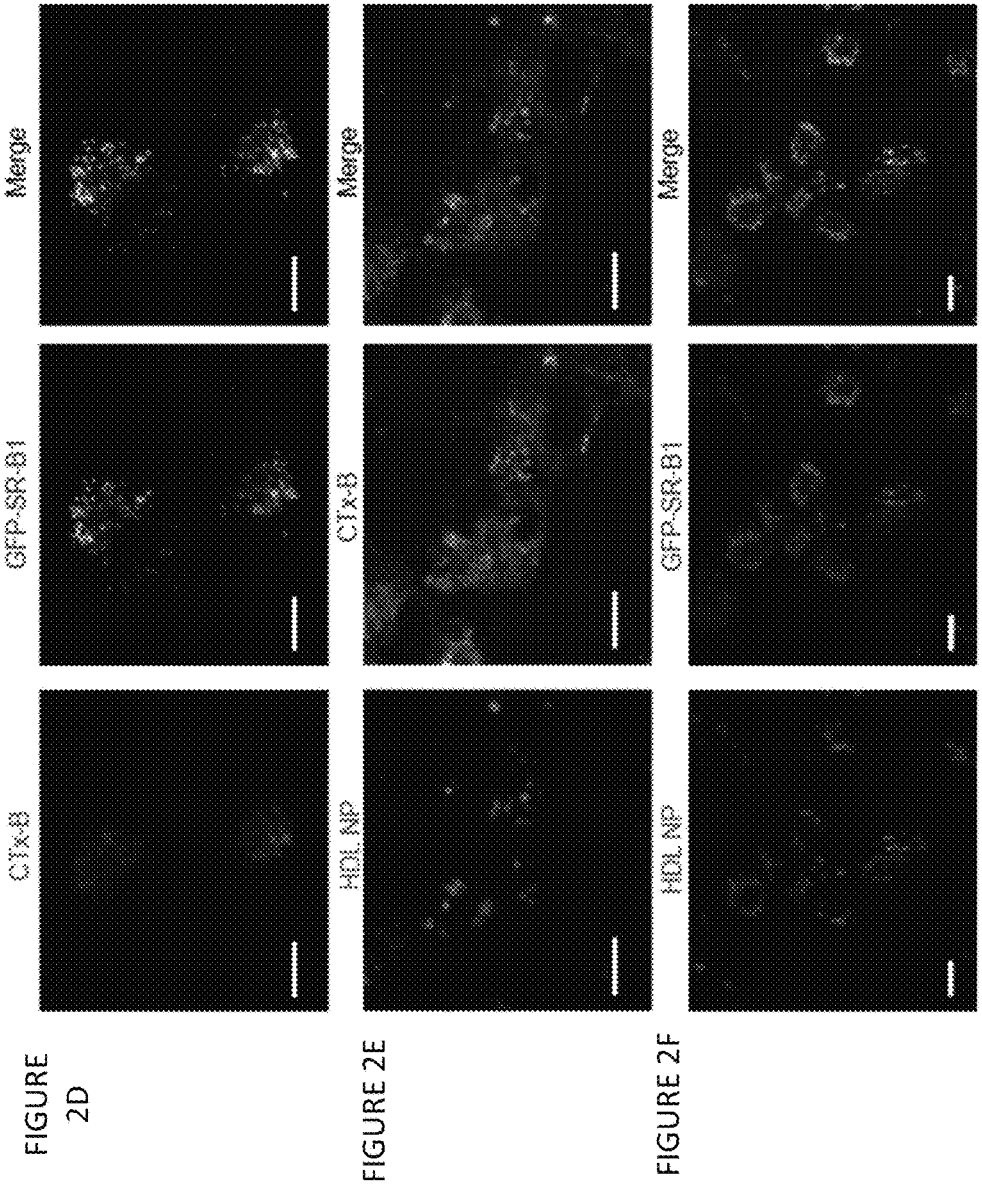
FIG. 2D shows confocal fluorescence microscopy of A375 melanoma cells (live) to assess co-localization of lipid rafts, HDL NPs, and GFP-SR-B1. (Scale bar=10 µm). Specifically.
FIG. 2E shows confocal fluorescence microscopy of A375 melanoma cells (live) to assess co-localization of lipid rafts, HDL NPs, and GFP-SR-B1. (Scale bar=10 µm). Specifically.
FIG. 2F shows confocal fluorescence microscopy of A375 melanoma cells (live) to assess co-localization of lipid rafts, HDL NPs, and GFP-SR-B1. (Scale bar=10 µm). Specifically.

We tested whether HDL NP treatment of melanoma cells disrupts exosome uptake, and, furthermore, whether such effects were mediated by targeting SR-B1 in lipid rafts. First, western blot analysis of lipid raft associated proteins confirmed that SR-B1 localizes to lipid rafts in A375 melanoma cells, and that SR-B1 is enriched in the insoluble lipid raft membrane fraction as compared to the cytoplasmic fraction (FIG. 2C). In complementary experiments, fluorescence confocal microscopy was used to visualize lipid rafts in A375 melanoma cells by labeling the rafts with cholera toxin subunit b (CTx-B) conjugated to Alexafluor-647. In addition, we visualized SR-B1 by stably expressing a green fluorescent protein-SR-B1 (GFP-SR-B1) fusion protein in the A375 cells.35 Cellular expression of the fusion protein by A375 melanoma cells was confirmed by western blotting (FIG. 4). Imaging revealed co-localization of lipid rafts with GFP-SR-B1 (FIG. 2D). These data establish that lipid rafts in our model melanoma cell line are enriched in SR-B1. To determine whether HDL NPs are targeted to lipid rafts and SR-B1, we treated cells with HDL NPs labeled with a lipophilic fluorescent dye, DID, and imaged cells to determine co-localization with lipid rafts and SR-B1. Data demonstrate that HDL NPs co-localize with lipid raft CTx-B labeled with Alexafluor-488 (FIG. 2E) and GFP-SR-B1 (FIG. 2F).

During the co-localization experiments, we imaged cells treated with HDL NPs at different time points. Intriguingly, images collected at 24 hours revealed a physical clustering of GFP-SR-B1 (FIG. 5A) and movies revealed an apparent reduction in movement and displacement of the receptor upon the addition of HDL NPs. To quantify these observations, we used automated image analysis [Olivio-Marin 2002; Jaqaman et al. 2008]. Data confirm an increase in the size and intensity of GFP-SR-B1 clusters, and a reduction in the number of labeled areas per cell after HDL NP treatment (FIGS. 5A-D). Also, we observed that GFP-SR-B1 clusters tended to remain at the cell membrane versus GFP-SR-B1 that was not clustered. This prompted us to perform tracking analysis to measure GFP-SR-B1 displacement (FIG. 6A). Data revealed a significant quantitative reduction in the velocity (FIG. 6B) and in the ratio of the final displacement relative to the total displacement length (rho) of GFP-SR-B1 clusters (FIG. 6C). Collectively, these data demonstrate that HDL NPs bind SR-B1, a receptor that localizes to A375 cell lipid rafts, leading to clustering and arrest of GFP-SR-B1.

The cellular uptake of exosomes is dependent on lipid raft-mediated endocytosis [Svensson et al. 2013]. As HDL NPs differentially modulate cellular cholesterol homeostasis and physically modulate SR-B1 localized to lipid rafts, we tested the hypothesis that HDL NPs interfere with cellular exosome uptake. Toward this end, we isolated exosomes from A375 melanoma cells and fluorescently labeled them with DiI. We then treated the A375 cells with labeled exosomes in the presence or absence of HDL NPs and measured cell uptake. Confocal fluorescent microscopy revealed that HDL NP treatment decreased exosome uptake as compared to untreated control cells at 16 hours (FIG. 7A). In order to quantify exosome uptake in large numbers of cells, we employed flow cytometry. Data demonstrated a dose-dependent decrease in exosome uptake after HDL NP treatment (FIGS. 7B, 7C). At the 50 nM dose, approximately 75% of exosome uptake by the A375 cells was blocked. Notably, the uptake of exosomes was similar in wild-type and GFP-SR-B1 A375 cells and similar reductions in exosome uptake after HDL NP treatment were observed in both lines (FIG. 8). Additionally, as a control, we treated GFP-SR-B1 A375 cells with exosomes to determine if GFP-SR-B1 clustering was observed. Data reveal that exosome treatment alone did not result in the clustering of GFP-SR-B1.

To test if HDL NPs interact with exosome or A375 cell-associated SR-B1, cells were pre-treated with HDL NPs for 12 hours, washed free of unbound HDL NP, and then treated with DiI labeled exosomes. Reduced exosome uptake (FIGS. 9A, 9B) following HDL NP pre-treatment suggests that decreased uptake is not due to extracellular interaction of exosomes and HDL NPs. As shown above in cholesterol flux experiments, HDL NP and hHDL both bind to SR-B1 and efflux cholesterol through this receptor. Accordingly, we determined whether hHDL had the same effect as HDL NP on inhibiting the cellular uptake of labeled exosomes using flow cytometry. Intriguingly, data show that hHDL does not drastically inhibit cellular exosome uptake (FIG. 10). As both hHDL and HDL NPs target SR-B1, but only HDL NPs inhibit exosome uptake, this provided an opportunity to demonstrate that hHDL and HDL NPs compete for the same cell surface receptors involved in exosome uptake. Co-treatment of cells with HDL NP and increasing concentrations of hHDL resulted in a partial recovery in exosome uptake (FIGS. 7D, 7E) suggesting competition for cell surface receptors, like SR-B1. Because we observed only partial recovery of exosome uptake, we reasoned that hHDL also reduces cellular exosome uptake. To test this, A375 cells were co-treated with fluorescently labeled exosomes and hHDL at 5, 50 or 500 nM concentrations and exosome uptake was measured using flow cytometry. Even at the 500 nM dose, which is 10-times the HDL NP concentration required for inhibition of exosome uptake, hHDL is unable to potently block the uptake of exosomes (FIG. 10). Lastly, to further confirm that HDL NPs engage SR-B1 to inhibit cellular exosome uptake, we employed a blocking antibody (Ab) to SR-B1 previously shown to inhibit HDL binding to this receptor [Gantman et al. 2010]. Data show that addition of the SR-B1 blocking Ab significantly reduces the ability of HDL NPs to inhibit exosome uptake (FIGS. 7F, 7G). Thus, HDL NPs specifically block exosome uptake in melanoma cells by binding SR-B1. Also, the high concentration of hHDL needed to significantly reduce HDL NP-mediated inhibition of exosome uptake suggest that HDL NPs have a higher binding affinity to cell-surface receptors, like SR-B1. These data also demonstrate that other receptors for HDL, not just SR-B1, participate in exosome uptake by melanoma cells. Intriguingly, due to the differential ability of HDL NP to inhibit exosome uptake in comparison to hHDL, the data suggested that both the binding of SR-B1 and differential modulation of cholesterol flux are mechanistically important in inhibiting exosome uptake.

SR-B1 clustering and the inhibition of cellular exosome uptake specifically induced by HDL NP encouraged us to further dissect the mechanism(s) by which HDL NPs reduce cellular exosome uptake (FIGS. 11A-M). Structurally, HDL NPs comprise a 5 nm diameter gold core and have the size, shape, and surface chemistry consistent with some hHDL species [Luthi et al. 2012]. Functionally, these particles are capable of binding SR-B1, resulting in the efflux of free cholesterol from cells, yet are unable to deliver esterified cholesterol. Therefore, we measured exosome uptake and SR-B1 clustering after treating A375 cells with: agents having an identical gold nanoparticle core, but with passive surface chemistry (polyethylene glycol nanoparticles, PEG NPs); the blocking Ab targeting SR-B1 [Gantman et al. 2010]; the small molecule inhibitor of free and esterified cholesterol flux through SR-B1, BLT-1 [Nieland et al. 2002]; and siRNA targeting melanoma cell SR-B1 expression. As measured with flow cytometry, HDL NPs are the only targeted single-entity agent that leads to clustering of GFP-SR-B1 and potent inhibition of cellular exosome uptake. Treatment of the cells with the PEG nanoparticle; hHDL; SR-B1 blocking antibody; siRNA that reduces SR-B1 expression; or BLT-1 did not result in the inhibition of exosome uptake or clustering of the receptor (FIGS. 11A-L). Comparing the data obtained with the other agents to that for HDL NP alone demonstrates that occupying SR-B1 and modulating free and esterified cholesterol flux by the HDL NP particle functions to cluster SR-B1 and disrupt cellular exosome uptake. To more conclusively support this mechanism of action, we co-treated A375 melanoma cells with hHDL and BLT-1 to occupy SR-B1 and block cholesterol flux through the receptor, respectively. Data show that this combination of agents significantly inhibits exosome uptake (FIGS. 11M, 11N) and there is a trend toward the clustering of GFP-SR-B1 (FIG. 5O) recapitulating what is observed for single agent, HDL NP. Finally, and as discussed above with regard to hHDL competition experiments, these data show that the cellular uptake of exosomes does not require SR-B1 (FIGS. 11I, 11J); however, specific binding of this receptor in lipid rafts by HDL NPs is a potent, targeted mechanism to inhibit cellular exosome uptake.

Data collected using melanoma cells are intriguing, but as proof-of-concept we were curious if inhibition of exosome uptake by HDL NPs was unique to the A375 melanoma cells or was more general. As mentioned, melanoma exosomes are known to target endothelial and macrophage cells leading to activation of an angiogenic response [Hood et al. 2009], and modulation of the immune system [Filipazzi et al. 2012]. Therefore, we chose an endothelial cell line, human dermal microvascular endothelial cells (HMVECs), as a proof-of-concept system to assess SR-B1 expression and exosome uptake. Like A375 cells, HMVECs express SR-B1 (FIG. 4). Human dermal microvascular endothelial cells (HMVECs) were treated with DiI labeled A375 exosomes and analyzed using fluorescence microscopy with and without HDL NP treatment. Data demonstrate a decrease in cellular fluorescence suggesting that exosome uptake is blocked in HDL NP-treated HMVECs. Treatment with hHDL had minimal effect at decreasing exosome uptake. RAW 264.7 macrophages also express SR-B1 [Matveev et al. 1999], so we analyzed exosome uptake in these cells after HDL NP treatment. As was observed with HMVECs, HDL NPs decreased the uptake of exosomes in RAW 264.7 macrophages as demonstrated by fluorescence microscopy. These ex vivo proof-of-concept experiments not only demonstrate that HDL NPs block exosome uptake in cell types shown to be important for melanoma progression, but also suggest that HDL NP may therapeutically modulate intercellular communication events that are critical for melanoma progression.

In conclusion, our data demonstrate that HDL NPs are a targeted and functional nanoconjugate that inhibit cellular vesicle uptake. HDL NPs tightly bind to SR-B1 localized to lipid rafts and modulate free and esterified cholesterol flux through this receptor and the HDL NPs are responsible for clustering and stagnating SR-B1 at the cell membrane and dramatically reducing cellular exosome uptake. As such, and in contrast to non-specific methods of disrupting lipid raft cholesterol balance and cellular exosome uptake, HDL NPs are a targeted nanoparticle that may inhibit intercellular communication.

Example 2

The present example demonstrates the preparation of synthetic nanostructures with an agent and without an agent and the loading of vesicles with these nanostructures.

Synthesis of HDL NPs with and without Agents:

HDL NPs were synthesized using 5 nm citrate stabilized colloidal gold nanoparticles (BBI Solutions) incubated with five-fold molar excess human apolipoprotein AI (Meridian Life Sciences) for one hour with shaking. The phospholipid 1,2-dipalmitoyl-sn-glycero-3-phosphoethanolamine-N-[3-(2-pyridyldithio)propionate] (DPPTE, Avanti Polar Lipids) was dissolved in ethanol and added in 250-fold molar excess to gold. Other lipids varied depending on the type of particle.

For particles without tracer, 250-fold molar excess to gold 1,2-dipalmitoyl-sn-glycero-3-phosphocholine (DPPC, Avanti) dissolved in ethanol was added and allowed to incubate overnight with shaking.

For particles with a rhodamine tracer, 200-fold molar excess to gold DPPC dissolved in ethanol was added, followed by 50-fold excess 1,2-dioleoyl-sn-glycero-3-phosphoethanolamine-N-(lissamine rhodamine B sulfonyl) (Avanti) in ethanol and allowed to incubate overnight with shaking.

For particles with a biotin tracer, 125-fold molar excess to gold DPPC in ethanol was added to 16:0 Biotinyl PE 1,2-dipalmitoyl-sn-glycero-3-phosphoethanolamine-N-(biotinyl) lipid (Avanti) in ethanol and allowed to incubate overnight with shaking.

All nanoparticles were purified by tangential flow filtration using a Kros Flo II tangential flow filtration system and then filtered using a 0.22 micron filter (VWR). Particle concentration was measured by ultraviolet-visible (UV-vis) spectroscopy.

Loading of Exosomes:

CWR 22Rv1 prostate cancer cells were cultured to 70% confluency and treated with HDL NPs at day 0 and day 1 to a final concentration of 20 nM in 15 ml of RPMI media (Corning) supplemented with 10% exosome-free fetal bovine serum and 1% penicillin/streptomycin. On day 2, conditioned media was collected and exosomes isolated using ExoQuick-TC (System Biosciences). Exosome protein concentration was measured by BCA assay, exosome size measured by dynamic light scattering, and exosome gold content was measured by UV-vis spectroscopy. Western blot was used to confirm that exosomal proteins (CD81, prostate specific membrane antigen) were present in exosomes from cells treated with HDL NPs. Flow cytometry using the ExoFlow kit (System Biosciences) was used to confirm fluorescence from exosomes containing rhodamine HDL NPs (FIG. 12). No exosomes are beads untreated with exosomes, control exosomes are from prostate cancer cells without HDL NP treatment, HDL NP exosomes are from prostate cancer cells treated with HDL NP, no tracer, and Rhodamine HDL NP exosomes are from prostate cancer cells treated with HDL NP with rhodamine tracer. FIG. 12A shows Rhodamine fluorescence from all groups; rhodamine fluorescence plotted on x-axis. Only exosomes from cells treated with the rhodamine HDL NPs display high rhodamine fluorescence (fourth panel). FIG. 12B shows Exo-FITC stains all exosomes present on the beads. Fluorescence is present for all groups treated with exosomes but not beads with no exosomes, confirming that exosomes were present in all samples yet only the rhodamine exosomes contain the rhodamine tracer.

Exosomes with biotin HDL NPs were incubated with a Cy5-streptavidin antibody and analyzed by flow cytometry using the ExoFlow kit to confirm presence of biotin on the exterior of the exosome (FIG. 13). Streptavidin beads coated with biotinylated CD81 antibody were incubated with control exosomes (top row), HDL NP exosomes (middle row), and biotinylated HDL NP exosomes (bottom row). All beads were incubated with each type of exosome individually, then washed and incubated with a Cy5-streptavadin antibody. Beads were washed again and analyzed via flow cytometry. The beads naturally have a high affinity for streptavidin, and all groups were highly fluorescent for Cy5 (right group in scatter plot), with a small proportion with lower fluorescence, containing less non-specific interactions (left group). However, the non-specific interactions in this particular group of beads were lower when treated with biotinylated HDL NP exosomes due to biotinylated exosomes removing the excess Cy5-streptavadin from the system, preventing the nonspecific interactions.

Example 3

The present example demonstrates that identifying and targeting a natural cellular pathway of exosome production provides a new mechanism for efficient and stable manipulation of exosomes that may enable in vivo, ex vivo, or in vitro applications.

Synthesis of Rh-HDL NPs:

We synthesized HDL NPs with rhodamine-labeled fluorescent phospholipids (Rh-HDL NP, see below). Data demonstrate that there are ~17 fluorescent phospholipids on each Rh-HDL NP (Table 1). Also, incorporation of the rhodamine fluorophore was evident by a noticeable absorption peak at 560 nm (FIG. 22). The Rh-HDL NPs have physical properties similar to those of HDL NPs that lack the labeled phospholipid (Table 1).

TABLE 1

Physical characterization data for Rh-HDL NPs.

| | HDL NP | Rh-HDL NP |
|---|---|---|
| Size (nm) | 13.64 ± 1.23 | 12.85 ± 0.44 |
| UV-Vis $\lambda^{max}$ (nM) | 519 | 517 |
| Zeta Potential (mV) | −41.6 ± 0.71 | −37.9 ± 2.12 |
| Rhodamine lipids/particle | 0 | 17 |

Characterization of Rh-HDL NP Containing Exosomes:

We initiated our studies with CWR22Rv1 prostate cancer cells. Cells were treated for 96 hours with Rh-HDL NPs (20 nM) or left untreated (control). Uptake of Rh-HDL NPs by CWR22Rv1 cells was confirmed by flow cytometry (FIG. 23). Exosomes were then isolated from conditioned media by ultracentrifugation (FIG. 14A). The exosomes from Rh-HDL NP-treated cells contained gold nanoparticles, as indicated by the darkened exosome pellet (FIG. 14B). Western blotting confirmed SR-B1 expression by the cells and their exosomes (FIG. 14C). Tetraspanins, such as cluster of differentiation 63 (CD63) and 81 (CD81), are proteins enriched in exosomes [Perez-Hernandez et al 2013; Rana & Zoller 2011; Thery et al. 2006] and are commonly used as exosome markers [Thery et al. 2006]. We used each of these as positive control markers for exosomes (FIG. 14C). The addition of Rh-HDL NPs did not change SR-B1 expression (FIG. 14C) or exosome production by the parent cells (FIG. 25). In order to ascertain the association between the Rh-HDL NPs and exosomes obtained by ultracentrifugation, the pellet was re-suspended and then spun at a lower speed capable of pelleting the Rh-HDL NPs, and therefore Rh-HDL NP-associated exosomes, but not exosomes free of the Rh-HDL NPs (FIG. 14A). Western blot analysis was then performed on the pellet and supernatant. Data show that CD81 and CD63 are enriched in both the pellet and the supernatant (FIG. 14C) suggesting that Rh-HDL NP associated with a sub-population of exosomes. Interestingly, SR-B1 was only found in the pellet fraction suggesting that the Rh-HDL NPs are selectively sorted to SR-B1 positive exosomes (FIG. 14C). Of note, prostate specific membrane antigen (PSMA), a common cell surface marker with specificity to prostate cancer cells, was only detectable in cell lysates regardless of Rh-HDL NP treatment (FIG. 14C) and was not detected in exosomes pellet or supernatant (FIG. 14C). The lack of beta actin confirmed that exosome preparations were free from cellular debris (FIG. 14C). To further characterize the association between Rh-HDL NPs and exosomes, we performed transmission electron microscopy (TEM), dynamic light scattering (DLS), and nano-tracking analysis (NTA) on isolated exosomes. TEM imaging revealed HDL NPs associated with the bilayer of exosomes (FIG. 14D). The measured size of isolated exosomes was not significantly changed by Rh-HDL NP treatment via DLS and NTA (FIG. 25). Taken together, these data demonstrate that Rh-HDL NPs are incorporated in SR-B1-positive exosomes produced by CWR22Rv1 cells.

Having determined that the Rh-HDL NPs associate with exosomes, we next investigated whether the exosomes isolated from conditioned media of CWR22Rv1 cells exhibited rhodamine fluorescence. Initially, we utilized conventional flow cytometry techniques by employing the commercially available ExoFlow kit. The kit contains magnetic beads coated with antibodies against CD81, capable of binding free exosomes. Exosomes isolated by ultracentrifugation were incubated with the beads, and the captured exosomes were stained with an exosome-specific fluorescein isothiocyanate (FITC) dye, included with the kit. The fluorescent signal from the beads was analyzed using flow cytometry. Based upon the FITC signal, exosomes were detected from both control and Rh-HDL NP treated cells (FIG. 15A). Using the same sets of beads, rhodamine (Rh) fluorescence was analyzed, and data show a nearly 15-fold increase in Rh fluorescence from Rh-HDL NP exosomes as compared to the untreated controls (FIG. 15B), demonstrating effective incorporation of the rhodamine-labeled phospholipid into the exosomes. We then utilized beads coated with an anti-rhodamine antibody. We observed similar fluorescent recovery from Rh-HDL NP exosomes as measured either by FITC (FIG. 15C) or Rh (FIG. 15D). Importantly, these data also demonstrate that the rhodamine phospholipid was available for antibody binding on the surface of the exosomes, which provides data consistent with the expected orientation of the exosome membrane with reference to Rh-HDL NP binding SR-B1 on the cell membrane (FIG. 14D and vide infra). As a negative control, anti-PSMA beads were minimally effective in retrieving Rh-HDL NP exosomes as measured by FITC (FIG. 15C) and Rh (FIG. 15D). These data demonstrate specific retrieval of fluorescent exosomes using either exosome (CD81) or Rh-HDL NP (rhodamine) specific markers.

Direct Flow Cytometry of Rh-HDL NP Containing Exosomes:

While bead-based flow cytometry analysis is a common tool for exosome characterization, direct measurement of exosomes using flow cytometry is an emerging technique [Nolan 2015] that enables rapid exosome profiling with minimal processing. Toward this end, we custom-calibrated an LSRFortessa analyzer with low noise electronics to detect particles in the exosome size range (FIG. 26, <200 nm). Using this setup we compared exosomes isolated by ultra-centrifugation from green fluorescent protein (GFP) expressing CWR22Rv1 cells with or without Rh-HDL NP treatment. The incorporation of GFP into the exosomes provides a control for exosome detection. Phosphate buffered saline (PBS) (FIG. 15E) and Rh-HDL NPs (FIG. 15F) were used as negative and rhodamine positive (Rh$^+$) controls, respectively. Flow cytometry demonstrated a pronounced GFP-positive (GFP$^+$) population in the untreated exosome sample without detectable Rh$^+$ fluorescence (FIG. 15G, green box). Rh-HDL NP treated cells resulted in a GFP$^+$/Rh$^+$ population (FIG. 15H, box). To further demonstrate the identity of the labeled structures as exosomes, the same samples were analyzed for the presence of CD81 using an allophycocyanin (APC)-tagged anti-CD81 antibody (CD81$^+$). Signal from the CD81 antibody can be detected (FIG. 15I), and data show the CD81 antibody did not label the Rh-HDL NP (FIG. 15J). Adding the CD81 antibody to GFP$^+$ exosomes reveals a CD81$^+$/GFP$^+$ population (FIG. 15K, box). Exosomes from Rh-HDL NP treated cells are shown to be CD81$^+$/Rh$^+$ (FIG. 15L, box). For further confirmation, we repeated these experiments using an APC-tagged anti-CD63 antibody. Similar results were obtained (FIG. 27). These data confirm the GFP$^+$/Rh$^+$ population is exosomes, and that direct flow cytometry can be used for detection.

SR-B1 is Required for Rh-HDL NP Loading of Exosomes:

To confirm that SR-B1 is required for Rh-HDL NP binding to exosomes, and to demonstrate the broader applicability of the technology, we used the SR-B1 positive melanoma cell line, A375, which are clearly engaged by Rh-HDL NP (FIG. 28). These cells were transfected with a plasmid encoding GFP-tagged SR-B1 (GFP-SR-B1). Expression of wild type and GFP-SR-B1 in cells and exosomes was not altered by Rh-HDL NP treatment (FIG. 29). Exosomes isolated by ultracentrifugation were analyzed by direct flow cytometry. Exosomes from wild type SR-B1 expressing cells were not GFP$^+$ as compared to those from A375 cells expressing GFP-SR-B1 (FIG. 29). We next utilized the CD81 antibody to detect CD81$^+$ exosomes from GFP-SR-B1 cells treated with Rh-HDL NPs. Flow cytometry revealed a clear CD81$^+$/Rh$^+$ population (FIG. 16A, pink gate) demonstrating labeling of melanoma exosomes by Rh-HDL NPs. Surprisingly, there is a minimal CD81$^+$/GFP$^+$ population despite the presence of a GFP$^+$/Rh$^+$ population (FIG. 29). Together, these data suggest that CD81$^+$/Rh$^+$ exosomes result from Rh-HDL NP association with wild-type SR-B1. To further explore the identity of the GFP$^+$/Rh$^+$ population of exosomes, we employed the CD63 antibody to stain isolated exosomes. Data reveal populations that are CD63$^+$/GFP$^+$ and CD63$^+$/Rh$^+$ (FIG. 29), and likely representing exosomes. These data highlight uncertainties of efficient and exclusive exosome loading of modified proteins using plasmid or viral vectors and the heterogeneity of exosome populations. Next, to implicate SR-B1, we performed SR-B1 knockdown experiments using a targeted siRNA and confirmed target knockdown by western blot and flow cytometry (see FIG. 30) For these experiments, conditioned media from treated cells was subject to direct flow cytometry to demonstrate that exosome isolation by ultracentrifugation was not necessary. Of note, direct flow cytometry results (FIG. 16B) are qualitatively similar to those obtained after exosome purification via ultracentrifugation (FIG. 16A). SR-B1 specific siRNA caused a significant reduction in the CD81$^+$/Rh$^+$ population (FIG. 16C, pink gate) as compared to cells treated with non-silencing control siRNA (FIG. 16, pink gate), and quantification of the ratio between CD81$^+$/Rh$^+$ to total CD81$^+$ events is shown in FIG. 16D. Adding the Rh-HDL NP to growth medium alone does not result in CD81$^+$/Rh$^+$ events (FIG. 30). Overall, results show that Rh-HDL NPs are incorporated into exosomes in an SR-B1 dependent manner.

Internalization of Rh-HDL NP by Target Cells:

Data showing that knockdown of SR-B1 reduced Rh$^+$ exosomes suggests that one possibility for labeling exosomes requires binding of SR-B1 on the cell membrane and incorporation of the receptor ligand complex into exosomes through an intracellular pathway. The presence of the gold nanoparticle at the Rh-HDL NP core provided a unique opportunity to visualize the nanoparticles using TEM and corresponding sub-cellular anatomy. To this end, we treated A375 melanoma cells with Rh-HDL NPs and examined them at 2, 6, and 16 hours following treatment. Strikingly, images reveal clear binding to the cell membrane (FIG. 17A) and internalization into early endosomes (FIG. 17B) and structures that resemble the multivesicular body (MVB) (FIG. 17C). The MVBs have vesicles that resemble exosomes, some of which have gold nanoparticles associated with their membrane. Also, exosomes found outside of the cells are clearly associated with gold nanoparticles (FIG. 17D). Consistent with our model (vide infra), gold nanoparticles are near exclusively located to the inner membrane of early endosomes or the outer membrane of exosomes. Ultimately, these data provide direct evidence of an intracellular thoroughfare where Rh-HDL NPs engage cell surface SR-B1. Both the Rh-HDL NP and SR-B1 are transported through the cell for eventual release on exosomes.

Rh-HDL NP Containing Exosomes are Stable in Human Serum:

To establish the potential implications for this technology for in vivo applications, we determined the stability of Rh-HDL NP labeled exosomes in human serum. We obtained blood samples from healthy volunteers, added Rh-HDL NP labeled A375 exosomes in increasing concentrations, isolated the serum component, stained for CD81, and then analyzed the samples via flow cytometry immediately and 24 hours following exosome addition. Serum alone was not Rh$^+$ (FIG. 31, 0 hrs, and FIG. 18A, 24 hrs). Increasing concentrations of CD81$^+$/Rh$^+$ exosomes were detected at the immediate time point (FIG. 31) and at 24 hours (FIGS. 18B-18D). The number of CD81$^+$/Rh$^+$ events linearly correlated with exosome concentration at the immediate (FIG. 31) and 24 hour time points (FIG. 18E). Thus, tailored exosomes maintain stability in serum and can be detected via Rh$^+$ fluorescence. Furthermore, Rh-HDL NPs added to human serum reveal that there is not significant background due to binding of native exosomes after the 24-hour incubation period (FIG. 18F). Collectively, these data show that Rh-HDL NP labeled exosomes are stable in serum for prolonged periods and can be detected using direct flow cytometry.

Rh-HDL NP Detection and Isolation of Free Exosomes that Express SR-B1:

To this point, data have been collected after treating cultured cells with Rh-HDL NPs and subsequently isolating exosomes. As exosomes contain SR-B1, we hypothesized that HDL NPs could bind free exosomes. Toward this end, we added Rh-HDL NPs to purified A375 exosomes and performed flow cytometry staining for CD81. Data revealed a CD81$^+$/Rh$^+$ population of exosomes confirming that the Rh-HDL NPs can bind SR-B1 on free exosomes (FIG. 19A). In proof-of-concept studies to demonstrate potential diagnostic utility of SR-B1 expression and HDL NPs, we measured CD81 and SR-B1 in exosomes isolated from the serum of patients diagnosed with melanoma. Our (FIG. 29) and published data [Lazar et al. 2015] show that SR-B1 is found in exosomes isolated from cultured melanoma cells. We isolated exosomes from serum samples and performed Western blot for CD81 and SR-B1. Data show that CD81 and SR-B1 (FIG. 19B) are present in exosomes from patients diagnosed with melanoma. Further, serum from each patient was incubated with Rh-HDL NPs and stained with CD81 antibody and then subjected to direct flow cytometry. Data reveal populations that are CD81$^+$/Rh$^+$ (FIGS. 19C-19F). Finally, serum samples incubated with Rh-HDL NPs were subjected to standard centrifugation (15,800×g) to pellet the gold nanoparticles, presumably, along with the bound exosomes. Western blot of the resulting pellet showed the presence of CD81 (FIG. 19G). Ultimately, Rh-HDL NPs may be useful for binding, detecting, and isolating SR-B1 exosomes present in human serum.

Cellular Uptake of Exosome and HDL NP Lipid Cargo:

Prior work from our group demonstrates that HDL NPs bind cellular SR-B1 and modulate the cellular uptake of exosomes [Plebanek et al. 2015]. Thus, we investigated if Rh-HDL NPs bound to free exosomes prevented exosome uptake. Free A375 exosomes were labeled with a lipophilic intercalating dye (DiO), washed, and then treated with Rh-HDL NPs. We confirmed the identity of DiO-labeled exosomes by both CD81 and CD63 staining (FIG. 32). Untreated A375 cells were exposed to DiO-labeled exosomes or DiO-labeled exosomes treated with Rh-HDL NPs. Flow cytometry data collected after incubating for two or twenty-four hours revealed clear uptake of DiO labeled exosomes and Rh-HDL NP treated DiO exosomes (FIG. 20). Of note, the slight reduction in exosome uptake observed in the Rh-HDL NP cases likely resulted from the small amount of residual free Rh-HDL NPs and is consistent with our previous findings.

Discussion:

Identifying and targeting a natural cellular pathway of exosome production provides a new mechanism for efficient and stable manipulation of exosomes that may enable in vivo applications. Rh-HDL NPs bind SR-B1 on parent cells and then become incorporated into newly formed exosomes. This synthetic ligand/receptor pair takes advantage of an inherent thoroughfare between the parent cell membrane and exosomes, with SR-B1 playing a crucial role. Our data support a model (FIG. 21) whereby HDL NPs bind to cell surface SR-B1, which remain associated through subsequent exosome formation. As exosomes maintain the same membrane polarity as parent cells [Vlassov et al. 2012], it is unlikely labeling takes place via other uptake methods since the surface of the developing exosomes does not contact the cytoplasm. The exosome TEM data (FIGS. 18A-18D) and capture of intact exosomes by anti-rhodamine antibody (FIGS. 15C, 15D) support this model. In addition, Rh-HDL NPs can bind SR-B1 in free exosomes, which may provide subsequent opportunities for exosome detection and enrichment.

Interestingly, SR-B1 has been shown to associate with CD81 [Lavie et al. 2014; Rocha-Perugini et al. 2009]. The detection of $GFP^+/Rh^+$ and $CD63^+/GFP^+$ events in A375 melanoma cells expressing GFP-SR-B1, but not $CD81^+/GFP^+$ events, suggests that GFP modification of SR-B1 may prevent GFP-SR-B1 sorting to $CD81^+$ exosomes.

Finally, we developed novel parameters for exosome characterization by flow cytometry which require minimal processing, and is time and cost efficient. Direct analysis of microvesicles by flow cytometry is an emerging field, and there is still much work required to develop instrumentation capable of microparticle sorting and standard techniques for routine use [Nolan 2015]. However, our data presented here shows much promise for rapid analysis of exosomes by flow cytometry. Further study of a greater number of patients with SR-B1-expressing tumors is required to determine if SR-B1 is a useful biomarker.

Rhodamine HDL NP (Rh-HDL NP) Synthesis:

Synthesis of Rh-HDL NPs was performed as previously described [Luthi et al. 2010; McMahon et al. 2011]. Citrate-stabilized 5 nm gold particles (Ted Pella, 15702-5) were incubated with a 5-fold excess of purified human apolipoprotein AI (Apo AI, Meridian Life Sciences, A01236H) at room temperature with gentle shaking for one hour. Ethanol was added to the synthesis at a final volume of 20%. Ethanol contributed from lipids was considered in the 20%. All lipids were re-suspended to 1 mM concentration in ethanol. Lipids were added in excess to gold concentration for a final of 250-fold for 1,2-dipalmitoyl-sn-glycero-3-phosphoethanolamine-N-[3-(2-pyridyldithio)propionate](Avanti Polar Lipids, 870205P), and 250-fold for 1,2-dipalmitoyl-sn-glycero-3-phosphocholine (DPPC, Avanti Polar Lipids, 850355P). For particles containing the rhodamine labeled phospholipid, DPPC was reduced to 200-fold, and a 50-fold excess of 1,2-dioleoyl-sn-glycero-3-phosphoethanolamine-N-(lissamine rhodamine B sulfonyl) (Avanti Polar Lipids, 810157P) was added. Solutions were allowed to incubate overnight at room temperature with gentle shaking.

Nanoparticles were then purified using tangential flow filtration (Spectrum Laboratories) using a mPES MidiKros 50 kD filter module (Spectrum Laboratories, D02-E050-05-N). Nanoparticles were sterile-filtered via passage through a 0.2 μm filter (VWR, 28145-501) and then quantified via UV-Vis spectroscopy by measuring the peak absorbance ($\lambda_{max}$) at ~520 nm (ε for 5 nm diameter AuNPs=$9.696 \times 10^6$ units). The size of the resultant conjugates was measured using dynamic light scattering (DLS, Zetasizer Nano ZS, Malvern). Particles were stored at 4° C. and protected from light. The number of rhodamine-labeled phospholipids per HDL NP was calculated by measuring the fluorescence liberated from Rh-HDL NPs at 1 nM (as measured by Au concentration), 10 minutes after addition of potassium cyanide (KCN) to 1 nM. Rhodamine phospholipids at known concentration were also treated with KCN and fluorescence analyzed to generate a standard curve in order to quantify molar concentration of rhodamine lipid in the 1 nM particle sample (thus number of rhodamine lipids per particle of Au).

Cell Culture:

CWR22Rv1 prostate cancer cells (a generous gift from D. Vander Griend Lab) were maintained in RPMI-1640 media (Corning, 10-041-CV) and A375 melanoma cells (CRL-1619, ATCC) were maintained in Dulbecco's Modification of Eagle's Medium (DMEM, Corning, 10-013-CV). Both media types were supplemented with 10% FBS (Atlanta Biologicals, S11150H) and 1% penicillin/streptomycin (GE Healthcare Life Sciences, SV30010). Both cells were cultured in 10% $CO_2$ at 37° C. in a humidified incubator.

The GFP-SR-B1 plasmid (pEGFP-N1, a generous gift from the Dhe-Paganon Lab) was stably transfected into the A375 melanoma cells using Lipofectamine 2000 (Life Technologies, 11668027). Transfected cells were selected using 500 μg/mL Geneticin (Life Technologies, 10131-027) followed by sorting on a FACSAria cell sorter (BD Biosciences) at the Robert H. Lurie Cancer Center Flow Cytometry Core Facility.

For exosome production, cells were cultured to approximately 70% confluency in five 152 $cm^2$ tissue culture plates (Corning, 353025), washed twice with 0.1 μm filtered phosphate buffered saline (PBS), and the media replaced with 20 mL of media containing 10% exosome depleted FBS and 1% penicillin/streptomycin. Exosomes were depleted from FBS via ultracentrifugation in a Beckman Coulter ultracentrifuge at 110,000×g for 18 h. Media was also filtered using a 0.1 μm filter unit (VWR, 89220-696).

In a typical experiment for Rh-HDL NP addition, the particles were added on day 1 to media at a concentration of 10 nM total. 48 hours later, additional Rh-HDL NPs were added to a final concentration of 20 nM. 96 hours after initial treatment, the media was pooled from the tissue culture plates and centrifuged at 3000×g for 15 minutes to remove cell debris. Cells were removed from flasks using TrypLE Express (Thermo Fisher, 12604013), counted using a Countess automated cell counter (Life Technologies), and frozen for protein analysis or washed and re-suspended in fresh media for flow cytometry analysis on an LSRFortessa cell analyzer (BD Biosciences).

Exosome Isolation:

For electron microscopy, exosomes were isolated using ExoQuick TC (System Biosciences, EXOTC10A-1) according to manufacturer's instructions. This was in order to provide a matrix so the exosomes could be embedded for sectioning. For all other assays including size analysis, western blot, and flow cytometry, exosomes were isolated from tissue culture media using ultracentrifugation in a Beckman Coulter ultracentrifuge using a Ti 45 rotor according to the protocol in Thery et al[24]. Briefly, conditioned media was separated into 50 mL aliquots, spun for 30 minutes at 10,000×g, supernatant removed, and supernatant was then spun at 100,000×g for 75 minutes. The pellet was then re-suspended in 100-200 μL 1×PBS filtered through a 0.1 μm filter (VWR). Exosomes from cells treated with Rh-HDL NPs were centrifuged again at 15,800×g in order to pellet the gold nanoparticles and separated into a supernatant and pellet fraction for further analysis. The pellet was re-suspended in 100-200 μL filtered 1×PBS.

Exosome Characterization:

Exosome size was determined using DLS on the Zetasizer Nano ZS (Malvern) using the number function. Nano tracking analysis (NTA) was performed using the NanoSight LM10-HS (Malvern) at the Northwestern University Keck Biophysics Facility. Exosomal protein concentration was determined via BCA Protein Assay (Thermo Scientific, 23227). Gold and rhodamine content was observed using UV-Vis spectroscopy and absorbance readings at 520 nm and 560 nm, respectively.

Western Blot:

Cells were lysed using M-Per Mammalian Protein Extraction Reagent (Thermo Scientific, 78501) and protein concentration determined using BCA assay, as above. 20 µg total cell lysate or exosomes were mixed with 4× Laemmli sample buffer (Bio-Rad, #1610747) containing no reducing agent (CD81 and CD63 only) [Thery et al. 2006] or 2-mercaptoethanol (SR-B1, PSMA, and beta actin). Samples were incubated at 95° C. for 5 minutes before being loaded onto a 4-20% glycine polyacrylamide mini gel (Bio-Rad, #4561093S) and electrophoresed for 32 minutes at 200V. Gels were transferred to a polyvinylidene fluoride membrane (Bio-Rad, #1620175) at 60V for 90 minutes then blocked with 5% milk in Tris-buffered saline containing 0.1% Tween-20 (TBS-Tween) for 1 hour. Membranes were then incubated overnight at 4° C. with antibodies listed in Table 2, all diluted in 5% milk in TBS-Tween. The following day, membranes were washed with TBS-Tween and then incubated for one hour with secondary antibodies as listed in Table 2, all diluted in 5% milk in TBS-Tween. Membranes were then washed with TBS-Tween and developed using the Amersham ECL Western Blotting Detection Reagent (GE Healthcare Life Sciences, RPN2106) and developed on Hyperfilm ECL (GE Healthcare Life Sciences, 28906839) according to the manufacturer's instructions.

TABLE 2

Primary and secondary antibodies and concentrations used for immunoblotting.

| Primary Antibody | Dilution | Secondary Antibody | Dilution |
| --- | --- | --- | --- |
| CD81 (Santa Cruz, sc-23962) | 1:250 | Goat anti-mouse (Bio-Rad, 170-6516) | 1:2000 |
| CD63 (Novus, NB100-77913) | 1:1000 | Goat anti-mouse (Bio-Rad, 170-6516) | 1:2000 |
| SR-B1 (Abcam, ab52629) | 1:1000 | Goat anti-rabbit (Bio-Rad, 170-6515) | 1:2000 |
| Beta actin (Cell Signaling, 4970C) | 1:1000 | Goat anti-rabbit (Bio-Rad, 170-6515) | 1:2000 |
| Y-PSMA (Abcam, ab19071) | 1:1000 | Goat anti-mouse (Bio-Rad, 170-6516) | 1:2000 |

Electron Microscopy:

Exosome pellets obtained from ExoQuick TC precipitation were embedded in agarose for processing and sectioning. Samples were sectioned to a thickness of 50 µm and imaged on a FEI Tecnai Spirit G2 transmission electron microscope at the Northwestern University Center for Advanced Microscopy operating at 120 kV.

Bead-Associated Flow Cytometry:

Bead-assisted flow cytometry was performed using the ExoFlow kit (System Biosciences, EXOFLOW400A-1). Beads were conjugated to biotinylated anti-CD81 (provided with kit), biotinylated anti-rhodamine (Vector Labs, BA-0605), or biotinylated anti-PSMA (BioLegend, 342510). 100 µg of exosomes were added to each reaction and carried out according to manufacturer's instructions. Flow cytometry was performed on a LSRFortessa Special Order Research Product (SORP) Cell Analyzer custom fitted with low noise Versa Module Europa Peripheral Component Connect Extents (VPX) electronics (BD Biosciences) at the Robert H. Lurie Cancer Center Flow Cytometry Core Facility using the gating strategy recommended in the documentation included with the ExoFlow kit.

Bead-Free Flow Cytometry from Ultracentrifugation Exosome Isolates:

A BD LSRFortessa SORP Cell Analyzer custom fitted with low noise VPX electronics (BD Biosciences) was calibrated for detection of nanoparticles in the <200 nm size range using Megamix-Plus SSC beads (Biocytex, 7803) and methodology defined by the manufacturer (see FIG. 26 for detailed gating strategy). 50 µl of exosomes (concentration: 8 ng/µL) from cells treated with Rh-HDL NPs were stained with 2.5 µL APC anti-CD81 antibody (BioLegend, 349510) or 2.5 µL APC anti-CD63 antibody (BioLegend, 353008) for 30 minutes at room temperature. Stained exosomes were diluted to a concentration of 1 ng/µL in 1×PBS before data was acquired on the calibrated analyzer. Data was acquired for 10 minutes at low setting for all samples.

For experiments where pre-isolated exosomes were labeled by Rh-HDL NPs, 50 µl of exosomes (concentration: 8 ng/µL) isolated from untreated A375 cells were incubated with 20 nM Rh-HDL NP for 1 hour at room temperature. Samples were then stained with APC anti-CD81 or APC anti-CD63 as above, and analyzed on the calibrated analyzer as above.

SR-B1 Knockdown Experiments:

GFP-SR-B1 A375 cells were plated in a 24-well plate at a concentration of 5,000 cells per well (a low cell number was used due to the fast growth rate of this line) and allowed to adhere overnight. The second day, 20 pmol control silencer RNA (Life Technologies, AM4611) or siSR-B1 (Wako Chemicals, 299-75001) was transfected to cells in appropriate wells using Lipofectamine RNAiMAX (Life Technologies, 13778030) according to manufacturer's instructions. 24 hours later, media was removed, cells washed, and media replaced with fresh 0.1 µm filtered DMEM. For experiments testing SR-B1 involvement in cellular processing of Rh-HDL NP into forming exosomes, Rh-HDL NP was added to appropriate wells to a concentration of 20 nM. For experiments testing SR-B1 involvement in labeling of excreted exosomes, no Rh-HDL NP was added at this time. 18 hours later, media was collected, filtered through a 0.2 µm filter to remove dead cells, and a 50 µL aliquot was stained with 2.5 µL APC anti-CD81 antibody for 30 minutes at room temperature. The sample was then diluted 1:30 in filtered PBS and analyzed on a LSRFortessa SORP analyzer calibrated for microparticle analysis as above.

Exosome Identification in Human Serum by Direct Flow Cytometry:

Fresh whole blood was obtained from a healthy adult volunteer. Rh-HDL NP A375 exosomes were added to 100 µL whole blood at varying concentrations including 0, 0.1, 0.5, 1.0, 2.0, 3.0, and 4.0 ng/µL. Additionally, Rh-HDL NP was added to blood in an equivalent concentration (based on gold concentration) as found in the 4.0 ng/µL exosome group. The sample was diluted 1:2 using 1×PBS and depleted of erythrocytes using Histopaque-1077 (Sigma-Aldrich, 10771) according to manufacturer's instructions. The serum component was centrifuged at 3000×g for 15 minutes to remove any remaining cells. A 50 µL aliquot of supernatant was stained with 2.5 µL of APC anti-CD81 antibody for 30 minutes at room temperature and then diluted 1:400 before being analyzed on a LSRFortessa SORP analyzer calibrated as described in the previous section. Data was acquired for 3 minutes at low setting for all samples. Remaining serum was incubated at 37° C. in a tissue culture incubator and an aliquot was analyzed as above 24 hours later.

Analysis of Human Serum Exosomes:

Human melanoma patient serum was isolated from whole blood obtained from the Interdisciplinary Melanoma Cooperative Group at NYU's Perlmutter Cancer Center, frozen at −80° C., and shipped overnight on dry ice to Northwestern University. For western analysis, samples were defrosted and exosomes isolated using ExoQuick (System Biosciences, EXOQ5A-1) according to the manufacturer's instructions. Isolated exosomes were stored at −80° C. until time of analysis. Exosome concentration was determined via BCA protein assay as above.

For flow analysis, 50 µl of serum was incubated with 20 nM Rh-HDL NP for 1 hour at room temperature. Samples were then stained with APC anti-CD81, diluted 1:500, and data collected for 10 minutes on a calibrated LSRFortessa cell analyzer as described above. Remaining sample was then spun at 15,800×g for 50 minutes, supernatant removed, and pellet resuspended in 10 µL molecular-biology grade water for western analysis as described above.

Exosome Uptake Experiments:

Wild-type A375 melanoma cells were grown in exosome-free media as detailed above. Conditioned media was collected and treated with Vybrant DiO Cell-Labeling Solution (Thermo Fisher, V-22886) according to manufacturer's instructions. Exosomes were isolated and washed and a portion incubated with 20 nM of Rh-HDL NP for 1 hour at room temperature. An aliquot was then stained with APC anti-CD81 or APC anti-CD63 for 30 minutes, diluted 1:400, and analyzed on the calibrated LSRFortessa cell analyzer as above. Upon verification of exosome presence, 100 µg of exosomes from each group (untreated and Rh-HDL NP treated) were incubated with A375 cells seeded in a 12-well plate at a density of 500,000 cells per well. Cells from individual wells were collected at 2 hours and 24 hours. Cells were washed twice with 1×PBS, removed using TrypLE Express, and re-suspended in 400 µL fresh media for flow cytometry using an LSRFortessa cell analyzer.

Data Analysis:

Data analysis of flow cytometry files was performed using FCS Express Version 4 (De Novo Software) and FlowJo Version 4X (FlowJo, LLC). Statistical analysis was performed using Prism software (GraphPad Software). Statistical tests used are indicated in figure legends. All error bars represent standard deviation of the sample.

REFERENCES

Acton, S. et al. Identification of scavenger receptor SR-BI as a high density lipoprotein receptor. *Science* 271, 518-520 (1996).

Anastasiadou, E. & Slack, F. J. Cancer. Malicious exosomes. *Science* 346, 1459-1460 (2014). Feng, D., et al. Cellular internalization of exosomes occurs through phagocytosis. *Traffic* 11, 675-687 (2010).

Atshaves, B. P. et al. SCP-2/SCP-x gene ablation alters lipid raft domains in primary cultured mouse hepatocytes. *J Lipid Res* 48, 2193-2211 (2007).

Challagundla, K. B. et al. Exosome-mediated transfer of microRNAs within the tumor microenvironment and neuroblastoma resistance to chemotherapy. *J. Natl. Cancer I.* 107 (2015).

Damiano, M. G. et al. Templated high density lipoprotein nanoparticles as potential therapies and for molecular delivery. *Adv. Drug Deliver. Rev.* 65, 649-662 (2013).

Ekstrom, E. J. et al. WNT5A induces release of exosomes containing pro-angiogenic and immunosuppressive factors from malignant melanoma cells. *Molecular cancer* 13, 88 (2014).

Filipazzi, P. et al. Recent advances on the role of tumor exosomes in immunosuppression and disease progression. *Seminars in cancer biology* 22, 342-349 (2012).

Gantman, A. et al. High glucose stimulates macrophage SR-BI expression and induces a switch in its activity from cholesterol efflux to cholesterol influx. *Biochemical and biophysical research communications* 391, 523-528 (2010).

Hood, J. L. et al. Paracrine induction of endothelium by tumor exosomes. *Laboratory investigation; a journal of technical methods and pathology* 89, 1317-1328 (2009).

Hood, J. L. et al. Exosomes released by melanoma cells prepare sentinel lymph nodes for tumor metastasis. *Cancer research* 71, 3792-3801 (2011).

Huang, R. et al. *Nature structural & molecular biology* 2011, 18, (4), 416-22.

Jaqaman, K. et al. Robust single-particle tracking in live-cell time-lapse sequences. *Nat Methods* 5, 695-702 (2008).

Johnsen, K. B. et al. A comprehensive overview of exosomes as drug delivery vehicles—endogenous nanocarriers for targeted cancer therapy. *Biochim. Biophys. Acta* 1846, 75-87 (2014).

Jung, T. et al. CD44v6 dependence of premetastatic niche preparation by exosomes. *Neoplasia* 11, 1093-1105 (2009).

Katakowski, M. et al. Exosomes from marrow stromal cells expressing miR-146b inhibit glioma growth. *Cancer Lett.* 335, 201-204 (2013).

Kharaziha, P. et al. Molecular profiling of prostate cancer derived exosomes may reveal a predictive signature for response to docetaxel. *Oncotarget* 6, 21740-21754 (2015).

Lingwood, D. & Simons, K. Lipid Rafts As a Membrane-Organizing Principle. *Science* 327, 46-50 (2010).

Lavie, M. et al. Identification of conserved residues in hepatitis C virus envelope glycoprotein E2 that modulate virus dependence on CD81 and SRB1 entry factors. *J. Virol.* 88, 10584-10597 (2014).

Lazar, I. et al. Proteome characterization of melanoma exosomes reveals a specific signature for metastatic cell lines. *Pigment Cell Melanoma Res.* 28, 464-475 (2015).

Luthi, A. J. et al. Nanotechnology for synthetic high-density lipoproteins. *Trends Mol. Med.* 16, 553-560 (2010).

Luthi, A. J. et al. Tailoring of biomimetic high-density lipoprotein nanostructures changes cholesterol binding and efflux. *ACS nano* 6, 276-285 (2012).

Luthi, A. J. et al. Robust passive and active efflux of cellular cholesterol to a designer functional mimic of high-density lipoprotein. *J Lipid Res* (2015).

Lydic, T. A. et al. Rapid and comprehensive 'shotgun' lipidome profiling of colorectal cancer cell derived exosomes. *Methods*, doi:10.1016/j.ymeth.2015.04.014 (2015).

Martins, V. R. et al. Tumor-cell-derived microvesicles as carriers of molecular information in cancer. *Curr Opin Oncol* 25, 66-75 (2013).

Marton, A. et al. Melanoma cell-derived exosomes alter macrophage and dendritic cell functions in vitro. *Immunol Lett* 148, 34-38 (2012).

Matveev, S. et al. Co-expression of scavenger receptor-BI and caveolin-1 is associated with enhanced selective cholesteryl ester uptake in THP-1 macrophages. *J Lipid Res* 40, 1647-1654 (1999).

McMahon, K. M. et al. Biomimetic high density lipoprotein nanoparticles for nucleic acid delivery. *Nano letters* 11, 1208-1214 (2011).

McMahon, K. M. & Thaxton, C. S. High-density lipoproteins for the systemic delivery of short interfering RNA. *Expert opinion on drug delivery* 11, 231-247 (2014).

Melo, S. A. et al. Glypican-1 identifies cancer exosomes and detects early pancreatic cancer. *Nature* 523, 177-182 (2015).

Neculai, D. et al. Structure of LIMP-2 provides functional insights with implications for SR-BI and CD36. *Nature* 504, 172-176 (2013).

Nerambourg, N. et al. *Langmuir* 2007, 23, (10), 5563-5570.

Nieland, T. J. et al. Discovery of chemical inhibitors of the selective transfer of lipids mediated by the HDL receptor SR-BI. *Proceedings of the National Academy of Sciences of the United States of America* 99, 15422-15427 (2002).

Nieland, T. J. F. et al. Negatively Cooperative Binding of High-Density Lipoprotein to the HDL Receptor SR-BI. *Biochemistry-Us* 50, 1818-1830 (2011).

Nolan, J. P. Flow Cytometry of Extracellular Vesicles: Potential, Pitfalls, and Prospects. *Curr. Protoc. Cytom.* 73, 13.14.1-13.14.16 (2015).

Olivo-Marin, J. C. Extraction of spots in biological images using multiscale products. *Pattern Recogn* 35, 1989-1996 (2002).

Peinado, H. et al. The secreted factors responsible for pre-metastatic niche formation: old sayings and new thoughts. *Seminars in cancer biology* 21, 139-146 (2011).

Peinado, H. et al. Melanoma exosomes educate bone marrow progenitor cells toward a pro-metastatic phenotype through MET. *Nature medicine* 18, 883-891 (2012).

Perez-Hernandez, D. et al. The intracellular interactome of tetraspanin-enriched microdomains reveals their function as sorting machineries toward exosomes. *J. Biol. Chem.* 288, 11649-11661 (2013).

Plebanek, M. P. et al. Nanoparticle Targeting and Cholesterol Flux Through Scavenger Receptor Type B-1 Inhibits Cellular Exosome Uptake. *Sci. Rep.* 5, 15724, (2015).

Putz, U. et al. The Tumor Suppressor PTEN Is Exported in Exosomes and Has Phosphatase Activity in Recipient Cells. *Sci Signal* 5(2012).

Rader, D. J. et al. The role of reverse cholesterol transport in animals and humans and relationship to atherosclerosis. *J Lipid Res* 2009, 50 Suppl, S189-94.

Rajendran, L. et al. Alzheimer's disease beta-amyloid peptides are released in association with exosomes. *Proceedings of the National Academy of Sciences of the United States of America* 103, 11172-11177 (2006).

Ramakrishnaiah, V. et al. Exosome-mediated transmission of hepatitis C virus between human hepatoma Huh7.5 cells. *Proceedings of the National Academy of Sciences of the United States of America* 110, 13109-13113 (2013).

Rana, S. & Zoller, M. Exosome target cell selection and the importance of exosomal tetraspanins: a hypothesis. *Biochem. Soc. T.* 39, 559-562 (2011).

Rana, S. et al., M. Toward tailored exosomes: the exosomal tetraspanin web contributes to target cell selection. *Int. J. Biochem. Cell B.* 44, 1574-1584 (2012).

Rocha-Perugini, V. et al. The association of CD81 with tetraspanin-enriched microdomains is not essential for Hepatitis C virus entry. *BMC Microbiol.* 9, 111 (2009).

Simons, K. & Gerl, M. J. Revitalizing membrane rafts: new tools and insights. *Nat Rev Mol Cell Bio* 11, 688-699 (2010).

Svensson, K. J. et al. Exosome uptake depends on ERK1/2-heat shock protein 27 signaling and lipid Raft-mediated endocytosis negatively regulated by caveolin-1. *The Journal of biological chemistry* 288, 17713-17724 (2013).

Thaxton, C. S. et al. Templated spherical high density lipoprotein nanoparticles. *Journal of the American Chemical Society* 131, 1384-1385 (2009).

Thery, C. et al. Isolation and characterization of exosomes from cell culture supernatants and biological fluids. *Current protocols in cell biology/editorial board, Juan S. Bonifacino et al.* Chapter 3, Unit 3 22 (2006).

Tripathy, S. et al. High Density Lipoprotein Nanoparticles Deliver RNAi to Endothelial Cells to Inhibit Angiogenesis. *Part. Syst. Char.* 31, 1141-1150 (2014).

Umemoto, T. et al. Apolipoprotein AI and high-density lipoprotein have anti-inflammatory effects on adipocytes via cholesterol transporters: ATP-binding cassette A-1, ATP-binding cassette G-1, and scavenger receptor B-1. *Circulation research* 112, 1345-1354 (2013).

Urban, S. et al. Scavenger receptor BI transfers major lipoprotein-associated phospholipids into the cells. *J. Biol. Chem.* 275, 33409-33415 (2000).

Valadi, H. et al. Exosome-mediated transfer of mRNAs and microRNAs is a novel mechanism of genetic exchange between cells. *Nat Cell Biol* 9, 654-U672 (2007).

Van Eck, M. et al. Scavenger receptor BI and ATP-binding cassette transporter A1 in reverse cholesterol transport and atherosclerosis. *Curr Opin Lipidol* 16, 307-315 (2005).

Vlassov, A. V., et al. Exosomes: current knowledge of their composition, biological functions, and diagnostic and therapeutic potentials. *Biochim. Biophys. Acta* 1820, 940-948 (2012).

Xiang, X. et al. Induction of myeloid-derived suppressor cells by tumor exosomes. *International journal of cancer. Journal international du cancer* 124, 2621-2633 (2009).

Yang, S. O. et al. Biomimetic, synthetic HDL nanostructures for lymphoma. *Proceedings of the National Academy of Sciences of the United States of America* 110, 2511-2516 (2013).

Yu, X. et al. The regulation of exosome secretion: a novel function of the p53 protein. *Cancer research* 66, 4795-4801 (2006).

Yu, S. et al. Tumor-derived exosomes in cancer progression and treatment failure. *Oncotarget* (2015).

Zhang, J. et al. Lipoprotein binding preference of CD36 is altered by filipin treatment. *Lipids in health and disease* 7, 23 (2008).

Zitvogel, L. et al. Eradication of established murine tumors using a novel cell-free vaccine: dendritic cell-derived exosomes. *Nat. Med.* 4, 594-600 (1998).

Zoller, M. Tetraspanins: push and pull in suppressing and promoting metastasis. *Nature reviews. Cancer* 9, 40-55 (2009).

All references, including publications, patent applications, and patents, cited herein are hereby incorporated by reference to the same extent as if each reference were individually and specifically indicated to be incorporated by reference and were set forth in its entirety herein.

What is claimed:

1. A synthetic nanostructure vesicle complex isolated from a biological sample or a tissue culture medium comprising
   a vesicle, the vesicle having a surface-bound receptor, wherein the vesicle is an exosome, and wherein the surface-bound receptor is SR-B1, and
   a synthetic nanostructure,
   wherein the synthetic nanostructure is bound to the surface-bound receptor.

2. The complex of claim 1, wherein the synthetic nanostructure comprises a nanostructure core,
a shell, the shell comprising a lipid layer surrounding and attached to the nanostructure core, and
a protein associated with the shell.

3. The complex of claim 1, wherein the synthetic nanostructure further comprises a diagnostic agent.

4. The complex of claim 3, wherein the diagnostic agent is a tracer lipid.

5. The complex of claim 4, wherein the tracer lipid comprises a chromophore, a biotin subunit, or both a chromophore and a biotin subunit.

6. The complex of claim 1, wherein the synthetic nanostructure further comprises a therapeutic agent.

7. The complex of claim 6, wherein the therapeutic agent is a nucleic acid, antiviral agent, antineurological agent, or antirheumatologic agent.

* * * * *